(12) United States Patent
Chedid et al.

(10) Patent No.: US 9,624,218 B2
(45) Date of Patent: Apr. 18, 2017

(54) PYRIDO[2,3-D]PYRIMIDIN-4-ONE COMPOUNDS AS TANKYRASE INHIBITORS

(71) Applicant: Eli Lilly and Company, Indianapolis, IN (US)

(72) Inventors: Marcio Chedid, Fishers, IN (US); Hisham Omer Eissa, Indianapolis, IN (US); Thomas Albert Engler, Indianapolis, IN (US); Kelly Wayne Furness, Avon, IN (US); Kenneth B. Rank, Zionsville, IN (US); Timothy Andrew Woods, Edinburgh, IN (US); Aaron D. Wrobleski, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/027,301

(22) PCT Filed: Oct. 29, 2014

(86) PCT No.: PCT/US2014/062832
§ 371 (c)(1),
(2) Date: Apr. 5, 2016

(87) PCT Pub. No.: WO2015/069512
PCT Pub. Date: May 14, 2015

(65) Prior Publication Data
US 2016/0251348 A1    Sep. 1, 2016

(51) Int. Cl.
C07D 471/04    (2006.01)
A61K 31/519    (2006.01)
C07D 487/04    (2006.01)
A61P 35/02    (2006.01)
A61P 35/04    (2006.01)

(52) U.S. Cl.
CPC ................ C07D 471/04 (2013.01)

(58) Field of Classification Search
CPC ................ C07D 471/04; A61K 31/519
See application file for complete search history.

(56) References Cited

FOREIGN PATENT DOCUMENTS

WO    2013/012723 A1    1/2013
WO    2013/117288 A1    8/2013

OTHER PUBLICATIONS

Papeo, G. et al., "PARP inhibitors in cancer therapy: an update," Expert Opinion; 23(17) (Apr. 1, 2013).
Huang, S-M. et al., "Tankyrase inhibition stabilizes axin and antagonizes Wnt signalling," Nature; 461 (Oct. 1, 2009) p. 614-620.
Waaler, J. et al., "A Novel Tankyrase Inhibitor Decreases Canonical Wnt Signaling in Colon Carcinoma Cells and Reduces Tumor Growth in Conditional APC Mutant Mice," Cancer Research; 72(11) (2012) p. 2822-2832.
Lau, T. et al., "A Novel Tankyrase Small-Molecule Inhibitor Suppresses APC Mutation-Driven Colorectal Tumor Growth," Cancer Research; 73(10) (2013) p. 3132-3144.
Shultz, M. et al., "Identification of NVP-TNKS656: The Use of Structure-Efficiency Relationships to Generate a Highly Potent, Selective, and Orally Active Tankyrase Inhibitor," Journal of Medicinal Chemistry (Jul. 11, 2013).
Miyaki, M. et al., "Characteristics of Somatic Mutation of the Adenomatous Polyposis Coll Gene in Colorectoral Tumors," Cancer Research; 54 (Jun. 1, 1994) p. 3011-3020.
Miyoshi, Y. et al., "Somatic mutations of the APC gene in colorectal tumors: mutation cluster region in the APC gene," Human Molecular Genetics; 1(4) (1992) p. 229-233.
Powell, S. et al., "APC mutations occur early during colorectal tumorigenesis," Letters to Nature; 359 (1992) p. 235-237.
Taniguchi, K. et al., "Mutational spectrum of b-catenin, AXIN1, and AXIN2 in hepatocellular carcinomas and hepatoblastomas," Oncogene; 21(2002) p. 4863-4871.
Liu, W. et al., "Mutations in AXIN2 cause colorectal cancer with defective mismatch repair by activating beta-catenin/TCF signaling," Nature genetics; 26 (Oct. 2000) p. 146-147.
Lammi, L. et al., "Mutations in AXIN2 Cause Familial Tooth Agenesis and Predispose to Colorectal Cancer," Am. J. Hum. Genet.; 74 (2004) p. 1043-1050.
Busch, A. et al., "Evidence for tankyrases as antineoplastic targets in lunch cancer," BMC Cancer; 13(211) (2013).
Yang, L. et al., "FZD7 has a critical role in cell proliferations in triple negative breast cancer," Oncogene; 30 (2011) p. 4437-4446.
De Robertis, A. et al., "Identification and Characterization of a Small-Molecule Inhibitor of Wnt Signaling in Glioblastoma Cells," Molecular Cancer Therapeutics; 12(7) (Jul. 2013) p. 1180-1189.
Polakis, P, "The many ways of Wnt in cancer," Current Opin. Genet. Dev.; 17 (2007) p. 45-51.
Barker, N. et al., "Mining the Wnt pathway for cancer therapeutics," Review; 5 (Dec. 2006) p. 997-1014.

(Continued)

Primary Examiner — Susanna Moore
(74) Attorney, Agent, or Firm — John C. Demeter

(57) ABSTRACT

Pyrido[2,3-d]pyrimidin-4-one compounds, formulations containing those compounds, and their use as tankyrase 1 and 2 inhibitors Formula (I).

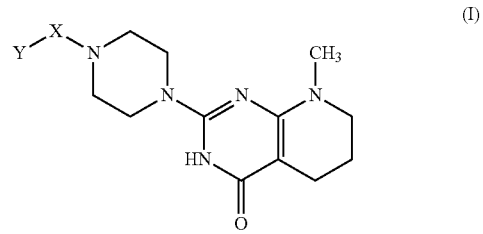

9 Claims, 1 Drawing Sheet

(56) References Cited

OTHER PUBLICATIONS

Qiang, Y. et al., "Wnt signaling in B-cell neoplasia," Oncogene; 22(2003) p. 1536-1545.
Groen, R. et al., "Illegitimate WNT Pathway Activation by beta-Catenin Mutation or Autocrine Stimulation in T-Cell Malignancies," Cancer Res; 68(17) (2008) p. 6959-6977.
Chim, C. et al., "Epigenetic dysregulation of Wnt signaling pathway in multiple myeloma," Leukemia; 21(2007) p. 2527-2536.
Gelebart, P. et al., "Constitutive activation of the Wnt canonical pathway in mantle cell lymphoma," Blood; 112 (Dec. 15, 2008) p. 5171-5179.
Heidel, F. et al., "Genetic and Pharmacologic Inhibition of beta-Catenin Targets lmatinib-Resistant Leukemia Stem Cells in CML," Cell Stem; 10(4) (2012) p. 412-424.
Ysebaert, L. et al., "Expression of beta-catenin by acute myeloid leukemia cells predicts enhanced clonogenic capacities and poor prognosis," Leukemia; 20 (2006) p. 1211-1216.
Schoumacher, M. et al., "Inhibiting Tankyrases sensitizes KRAS mutant cancer cells to MEK inhibitors via FGFR2 feedback signaling," Cancer Research (Apr. 18, 2014).

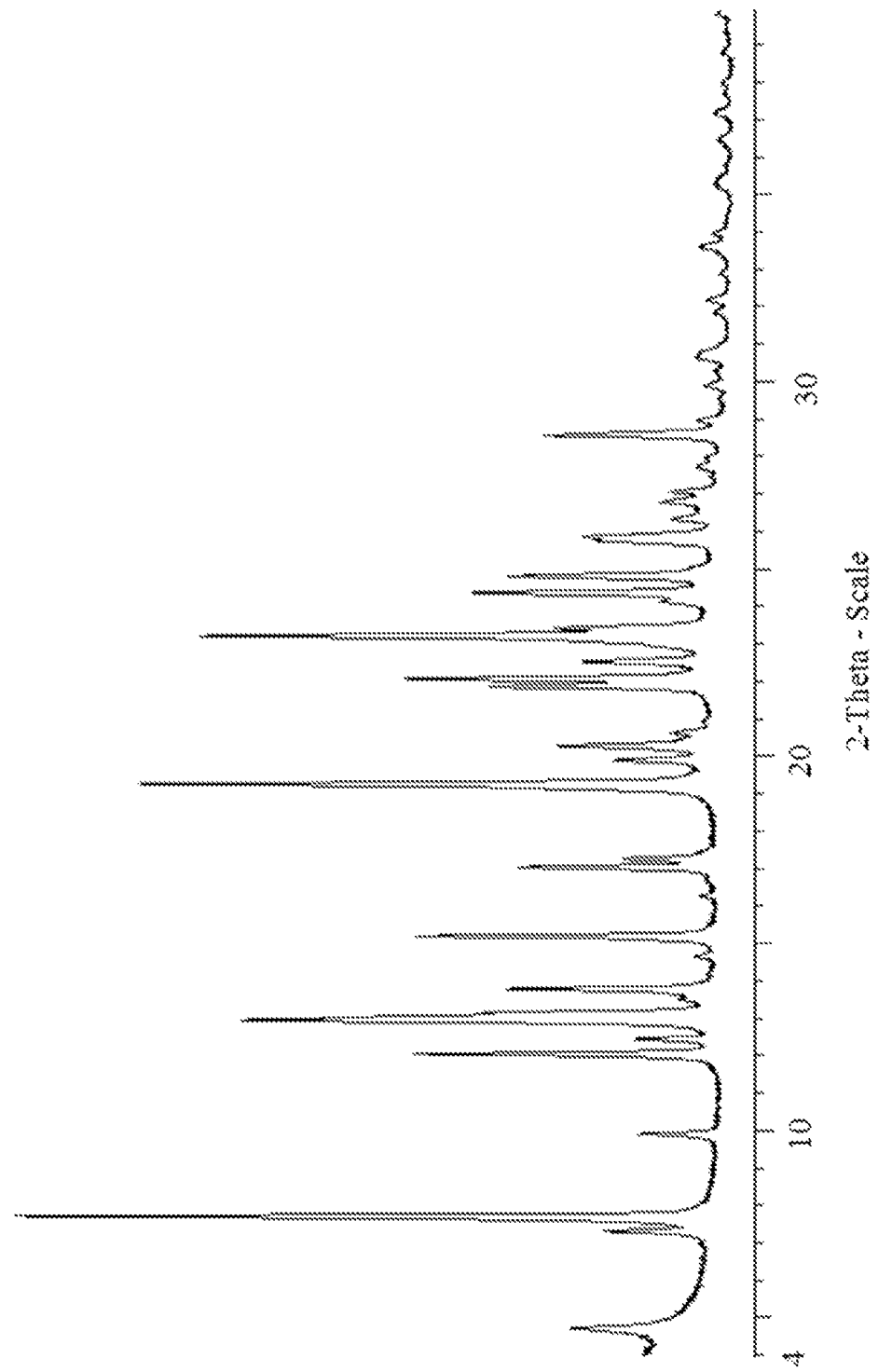

PYRIDO[2,3-D]PYRIMIDIN-4-ONE COMPOUNDS AS TANKYRASE INHIBITORS

Wnt signaling triggers three intracellular signaling cascades which include the β-catenin-mediated canonical pathway, the non-canonical planar cell polarity and the Wnt/calcium pathway. The evolutionarily conserved canonical Wnt signaling pathway regulates many cellular processes including cell proliferation, differentiation, adhesion and maintenance. The canonical pathway, which regulates β-catenin protein levels within cells, is initiated when Wnt ligands bind to cell surface Frizzled and lipoprotein receptor-related protein (LRP)5/6 co-receptors, which in turn promote the displacement of the kinase GSK3 from the APC/Axin/GSK-3 (adenomatous polyposis coli (APC), Axin, glycogen synthase kinase 3α/β (GSK3)) destruction complex. In the presence of Wnt binding (On-state), Dishevelled (a protein in the Wnt pathway) is activated which, in turn, recruits GSK3 away from the destruction complex leading to the accumulation of cytosolic β-catenin, translocation of β-catenin to the nucleus, interaction with T-cell factor/lymphoid enhancer factor (TCF/LEF) family transcription factors and transcription of canonical Wnt pathway responsive genes. In the absence of Wnt ligands (Off-state), cytosolic β-catenin is constitutively phosphorylated and targeted for ubiquitination and degradation by the proteasome.

The two highly homologous human tankyrase isoforms, tankyrase 1 and 2 (TNKS1 and TNKS2) are members of the poly(ADP-ribose)polymerase (PARP) enzyme family that catalyze the post-translational modification of proteins using β NAD+ as a substrate to successively add ADP ribose moieties onto target proteins (parylation or parsylation). One of the protein substrates for tankyrases is Axin, a concentration-limiting component of the β-catenin destruction complex; parsylation marks Axin for degradation and tankyrase inhibition leads to Axin stabilization, Wnt signaling inhibition and β catenin degradation.

Wnt signaling pathway activating mutations are found in a broad range of cancers and are believed to contribute to tumor initiation, maintenance, and/or progression. Therefore, inhibition of tankyrase activity appears to be a promising approach in the treatment of cancers such as colorectal cancer, gastric cancer, liver cancer, breast cancer (including triple negative breast cancer), ovarian cancer, medulloblastoma, melanoma, lung cancer (including non-small cell lung cancer), pancreatic cancer, prostate cancer, glioblastoma, T-cell lymphoma, T-lymphoblastic lymphoma, T-cell acute lymphocytic leukemia (T-ALL)), mantle cell lymphoma, multiple myeloma, chronic myeloid leukemia, and acute myeloid leukemia.

Considerable efforts have been made to identify pharmaceutical agents that inhibit the canonical Wnt/β-catenin signaling pathway. TNKS1 and TNKS2 inhibitors such as WO 2013/117288 are known.

Despite WO 2013/117288, there is a need to find compounds having TNKS1 and TNKS2 inhibitory activity. There is a further need to find compounds having selective inhibition of TNKS1 and TNKS2 over other PARPs.

FIG. 1 is a representative XRPD pattern for 8-Methyl-2-[4-(pyrimidin-2-ylmethyl)piperazin-1-yl]-3,5,6,7-tetrahydropyrido[2,3-d]pyrimidin-4-one 4-methylbenzenesulfonic acid salt, the compound of Example 6.

One aspect of the present invention are compounds of Formula I:

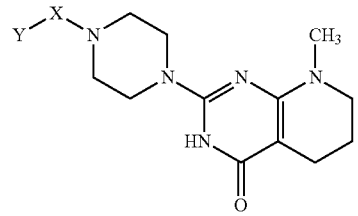

wherein:
Y is:

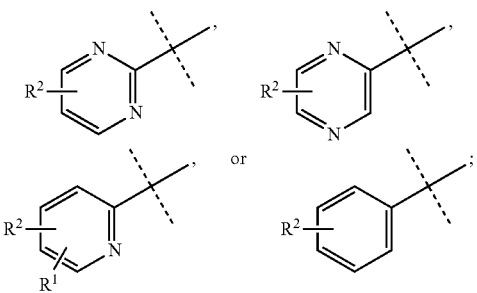

X is —CH$_2$—, —C(CH$_3$)H—, or —C(CH$_2$CH$_3$)H—;
R$^1$ is hydrogen, hydroxy, or halo;
R$^2$ is hydrogen, halo, —CN, —CH$_3$, CF$_3$, or —OCH$_3$;
or a pharmaceutically acceptable salt thereof.

Preferably, a further aspect of the present invention provides compounds of Formula I wherein:
Y is:

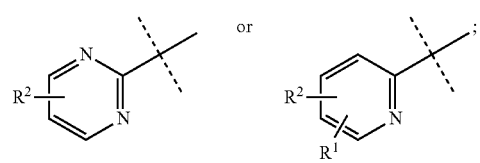

X is —CH$_2$—, —C(CH$_3$)H—, or —C(CH$_2$CH$_3$)H—;
R$^1$ is hydrogen, hydroxy, or halo;
R$^2$ is hydrogen, halo, —CN, —CH$_3$, CF$_3$, or —OCH$_3$;
or a pharmaceutically acceptable salt thereof.

Preferably, another aspect of the present invention provides compounds of Formula I wherein:
Y is

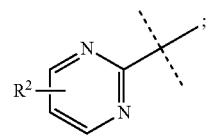

X is —CH$_2$—, —C(CH$_3$)H—, or —C(CH$_2$CH$_3$)H—;
R$^2$ is hydrogen, halo, —CN, —CH$_3$, CF$_3$, or —OCH$_3$;
or a pharmaceutically acceptable salt thereof.

Another preferred aspect of the present invention provides compounds of Formula I wherein:
Y is:

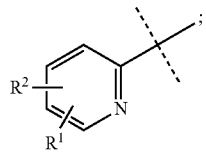

X is —CH$_2$—, —C(CH$_3$)H—, or —C(CH$_2$CH$_3$)H—;
R$^1$ is hydrogen, hydroxy, or halo;
R$^2$ is hydrogen, halo, —CN, —CH$_3$, CF$_3$, or —OCH$_3$;
or a pharmaceutically acceptable salt thereof.

A preferred aspect of the present invention is a compound:
8-Methyl-2-[4-(pyrimidin-2-ylmethyl)piperazin-1-yl]-3,5,6,7-tetrahydropyrido[2,3-d]pyrimidin-4-one, or a pharmaceutically acceptable salt thereof;
8-Methyl-2-[4-(1-pyrimidin-2-ylethyl)piperazin-1-yl]-3,5,6,7-tetrahydropyrido[2,3-d]pyrimidin-4-one, or a pharmaceutically acceptable salt thereof;
2-[4-[(4-Chloropyrimidin-2-yl)methyl]piperazin-1-yl]-8-methyl-3,5,6,7-tetrahydropyrido[2,3-d]pyrimidin-4-one, or a pharmaceutically acceptable salt thereof; or
2-[4-[(4-methoxypyrimidin-2-yl)methyl]piperazin-1-yl]-8-methyl-3,5,6,7-tetrahydropyrido[2,3-d]pyrimidin-4-one, or a pharmaceutically acceptable salt thereof.

Another preferred aspect of the present invention is a compound:
2-[4-[(3-Bromo-2-pyridyl)methyl]piperazin-1-yl]-8-methyl-3,5,6,7-tetrahydropyrido[2,3-d]pyrimidin-4-one, or a pharmaceutically acceptable salt thereof;
2-[4-[(3-Chloro-2-pyridyl)methyl]piperazin-1-yl]-8-methyl-3,5,6,7-tetrahydropyrido[2,3-d]pyrimidin-4-one, or a pharmaceutically acceptable salt thereof;
2-[4-[(3-Fluoro-2-pyridyl)methyl]piperazin-1-yl]-8-methyl-3,5,6,7-tetrahydropyrido[2,3-d]pyrimidin-4-one, or a pharmaceutically acceptable salt thereof; or
2-[[4-(8-Methyl-4-oxo-3,5,6,7-tetrahydropyrido[2,3-d]pyrimidin-2-yl)piperazin-1-yl]methyl]pyridine-3-carbonitrile, or a pharmaceutically acceptable salt thereof.

A further aspect of the present invention is a pharmaceutical composition comprising a compound of Formula I, or a pharmaceutically acceptable salt thereof, in association with a pharmaceutically acceptable carrier.

Still a further aspect of the present invention provides a method of inhibiting Tankyrase 1 and 2 in a cancer patient in need thereof, comprising administering a therapeutically effective amount of a compound of Formula I, or a pharmaceutically acceptable salt thereof, to said patient.

Another aspect of the present invention provides a method of treating a cancer which is colorectal cancer, gastric cancer, liver cancer, breast cancer, triple negative breast cancer, ovarian cancer, medulloblastoma, melanoma, lung cancer, non-small cell lung cancer, pancreatic cancer, prostate cancer, glioblastoma, T-cell lymphoma, T-lymphoblastic lymphoma, T-cell acute lymphocytic leukemia (T-ALL), mantle cell lymphoma, multiple myeloma, chronic myeloid leukemia, or acute myeloid leukemia in a patient comprising administering to a patient in need thereof a therapeutically effective amount of a compound of Formula I, or a pharmaceutically acceptable salt thereof.

A still further aspect of the present invention provides a compound of Formula I, or a pharmaceutically acceptable salt thereof, for use in therapy.

Another aspect of the present invention provides a compound of Formula I, or a pharmaceutically acceptable salt thereof, for use in the treatment of a cancer which is colorectal cancer, gastric cancer, liver cancer, breast cancer, triple negative breast cancer, ovarian cancer, medulloblastoma, melanoma, lung cancer, non-small cell lung cancer, pancreatic cancer, prostate cancer, glioblastoma, T-cell lymphoma, T-lymphoblastic lymphoma, T-cell acute lymphocytic leukemia (T-ALL), mantle cell lymphoma, multiple myeloma, chronic myeloid leukemia, or acute myeloid leukemia.

A further aspect of the present invention provides use of a compound of Formula I, or a pharmaceutically acceptable salt thereof, for the manufacture of a medicament for treatment of a cancer which is colorectal cancer, gastric cancer, liver cancer, breast cancer, triple negative breast cancer, ovarian cancer, medulloblastoma, melanoma, lung cancer, non-small cell lung cancer, pancreatic cancer, prostate cancer, glioblastoma, T-cell lymphoma, T-lymphoblastic lymphoma, T-cell acute lymphocytic leukemia (T-ALL), mantle cell lymphoma, multiple myeloma, chronic myeloid leukemia, or acute myeloid leukemia.

The term "patient" means mammal and "mammal" includes, but is not limited to, a human.

The term "triple negative breast cancer" refers to a breast cancer characterized by a tumor sample having tested negative for estrogen receptors (ER), progesterone receptors (PR), and hormone epidermal growth factor receptors 2 (HER2/neu).

"Therapeutically effective amount" or "effective amount" means the dosage of a compound, or pharmaceutically acceptable salt thereof, or pharmaceutical composition containing a compound, or pharmaceutically acceptable salt thereof, necessary to inhibit Wnt/β-catenin signaling pathway in a cancer patient, and either destroy the target cancer cells or slow or arrest the progression of the cancer in a patient. Anticipated dosages of a compound or a pharmaceutically acceptable salt thereof are in the range of 0.1 to 200 mg/patient/day. Preferred dosages are anticipated to be in the range of 1 to 175 mg/patient/day. Most preferred dosages are anticipated to be in the range of 5 to 150 mg/patient/day. The exact dosage required to treat a patient and the length of treatment time will be determined by a physician in view of the stage and severity of the disease as well as the specific needs and response of the individual patient. Although expressed as dosage on a per day basis, the dosing regimen may be adjusted to provide a more optimal therapeutic benefit to a patient and to manage and/or ameliorate undesirable pharmacodynamic effects. In addition to daily dosing, dosing every other day (Q2D); every other day over a five day period followed by two days without dosing (T.I.W.); or every third day (Q3D) may be appropriate.

The terms "treatment," "treat," and "treating," are meant to include the full spectrum of intervention for the cancer from which the patient is suffering, such as administration of the active compound to alleviate to slow or reverse one or more of the symptoms and to delay progression of the cancer even if the cancer is not actually eliminated. The patient to be treated is a mammal, in particular a human being.

A compound of the present invention is preferably formulated as a pharmaceutical composition using a pharmaceutically acceptable carrier and administered by a variety of routes. Preferably, such compositions are for oral administration. Such pharmaceutical compositions and processes for preparing them are well known in the art. See, e.g., REMINGTON: THE SCIENCE AND PRACTICE OF PHARMACY (A. Gennaro, et al., eds., 19$^{th}$ ed., Mack Publishing Co., 1995). In a particular embodiment, the pharmaceutical composition comprises 8-methyl-2-[4-(pyrimidin-2-ylmethyl)piperazin-1-yl]-5,6,7,8-tetrahydropyrido[2,3-d]pyrimidin-4(3H)-one or a pharmaceutically acceptable salt thereof, together with a pharmaceutically acceptable carrier and optionally other therapeutic ingredients particularly for treatment of a specific cancer type.

A compound of the present invention is capable of reaction with a number of inorganic and organic acids to form pharmaceutically acceptable acid addition salts. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

A compound of the present invention, such as Example 1, is named: 8-methyl-2-[4-(pyrimidin-2-ylmethyl)piperazin-1-yl]-5,6,7,8-tetrahydropyrido[2,3-d]pyrimidin-4(3H)-one (IUPAC); and may also be named: pyrido[2,3-d]pyrimidin-4(3H)-one, 5,6,7,8-tetrahydro-8-methyl-2-[4-(2-pyrimidinylmethyl)-1-piperazinyl]- (CAS); and other names may be used to unambiguously identify a compound of the present invention.

It will be understood compounds of Formula I are depicted as a single stereoisomer. A particular defined substituent may give rise to a chiral center affording a racemic mixture or two stereoisomers. As used herein, unless otherwise designated, references to a specific compound are meant to include individual stereoisomers and racemic mixtures including the named compound. Specific stereoisomers can be prepared by stereospecific synthesis using enantiomerically pure or enriched starting materials. The specific stereoisomers of either starting materials, intermediates, or racemic mixtures can be resolved by techniques well known in the art, such as those found in *Stereochemistry of Organic Compounds*, E. I. Eliel and S. H. Wilen (Wiley 1994) and *Enantiomers, Racemates, and Resolutions*, J., Jacques, A. Collet, and S. H. Wilen (Wiley 1991), including chromatography on chiral stationary phases, enzymatic resolutions, or fractional crystallization or chromatography of diastereomers formed for that purpose, such as diastereomeric salts. Where a chiral compound is isolated or resolved into its isomers, but absolute configurations or optical rotations are not determined, the isomers are arbitrarily designated as isomer 1 and isomer 2 corresponding to the order each elutes from chiral chromatography and if chiral chromatography is initiated early in the synthesis, the same designation is applied to subsequent intermediates and examples.

One of ordinary skill in the art will recognize the compounds of Formula I can exist in tautomeric equilibrium. For illustrative purposes, the equilibrium is shown below:

For convenience, the 4-oxo form is depicted in Formula I, and the corresponding nomenclature is used throughout this specification. However, such depictions include the corresponding tautomeric hydroxy form.

The compounds employed as initial starting materials in the synthesis of compounds of the present invention are well known and, to the extent not commercially available, are readily synthesized using specific references provided, by standard procedures commonly employed by those of ordinary skill in the art, or are found in general reference texts.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

Additionally, certain intermediates described in the following schemes may contain one or more nitrogen protecting groups. The variable protecting group may be the same or different in each occurrence depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Abbreviations used herein are defined according to *Aldrichimica Acta*, Vol. 17, No. 1, 1984. Other abbreviations are defined as follows: "APC" refers to adenomatous polyposis coli; "BID" refers to twice daily dosing; "biotinylated NAD+" refers to 6-biotin-17-nicotinamide-adenine-dinucleotide; "BOC" refers to refers to tert-butyloxycarbonyl; "DCM" refers to dichloromethane; "DMF" refers to dimethylformamide; "DMAP" refers to 4-dimethylaminopyridine; "DMEM" refers to Dulbecco's Modified Eagle's Medium; "DMSO" refers to dimethyl sulfoxide; "DPBS" refers to Dulbecco's Phosphate Buffered Saline; "DTT" refers to dithiothreitol; "EDCI" refers to 1-ethyl-3-(3-dimethylaminopropyl)carbodiimide; "EGFP" refers to Enhanced Green Fluorescent Protein; "EtOAc" refers to ethyl acetate; "FBS" refers to Fetal Bovine Serum; "Flag tag" refers to Flag peptide DYKDDDDK, N-terminus to C-terminus (SEQ ID NO: 6); "HEK" refers to human embryonic kidney; "HEPES" refers to 4-(2-hydroxyethyl)-1-piperazineethanesulfonic acid; "HOAc" refers to acetic acid; "HRP" refers to horseradish peroxidase; "IPAm" refers to isopropylamine; "MEM" refers to Minimum Essential Medium; "MeOH" refers to methanol; "MOI" refers to multiplicity of infection; "NCBI" refers to National Center

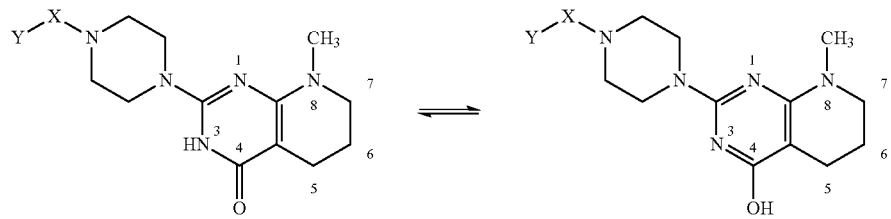

for Biotechnology Information; "PBS" refers to Phosphate Buffered Saline; "RPMI" refers to Roswell Park Memorial Institute; "SCX" refers to a purification column of strong cation exchange phenyl sulfonic acid bound to silica; "SCX-2" refers to a purification column of strong cation exchange propylsulfonic acid bound to silica; "SFC" refers to supercritical fluid chromatography; "TBS" refers to Tris buffered saline; "THF" refers to tetrahydrofuran; "TBME" refers to tert-butyl methyl ether; "TMB peroxidase" refers to 3,3',5,5'-tetramethylbenzidine; Tris" refers to tris(hydroxymethyl) aminomethane; and "X-Phos" refers to 2-(dicyclohexylphosphino)-2',4',6'-triisopropylbiphenyl.

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds of Formula I, or pharmaceutically acceptable salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art.

Scheme 1 depicts the formation of 8-methyl-2-piperazin-1-yl-3,5,6,7-tetrahydropyrido[2,3-d]pyrimidin-4-one (6) as a TFA salt, the neutral material (7) and the trifluoroboranate methyl salt of (7).

In Step A, a protected 2-piperazine-1-yl-3H-pyrido[2,3-d]pyrimidin-4-one (3) is obtained from cyclization of a protected piperazine-1-carboxamide hydrochloride salt (1) with ethyl 2-chloronicotinate (2). The reaction proceeds in an inert solvent, such as DMF, in the presence of a strong base, such as potassium tert-butoxide, at a temperature of 50-120° C. The preferred protecting group is a tert-butyloxycarbonyl but other carbamate protecting groups could be used.

In Step B, a protected 2-piperazine-1-yl-3H-pyrido[2,3-d]pyrimidin-4-one (3) is methylated using methyl iodide to give the quaternary salt, protected 8-methyl-2-piperazin-1-yl-3H-pyrido[2,3-d]pyrimidin-8ium-4-one iodide (4) (Z is I, Scheme 1). The reaction proceeds in an autoclave in an inert solvent, such as THF or dioxane, at a temperature of 50-120° C. for 4 to 24 h. Alternatively the methyl sulfate salt can be formed by adding dimethylsulfate to compound (3) in a polar aprotic solvent such as DMF with heating at about 60-80° C. The solution is transferred at room temperature to a vessel containing TMBE to precipitate the product (4) for Z is $CH_3OSO_3$.

In Scheme 1, Step C, the quaternary salt (4, Z is I) is reduced to provide protected 8-methyl-2-piperazin-1-yl-3,5, Scheme 1

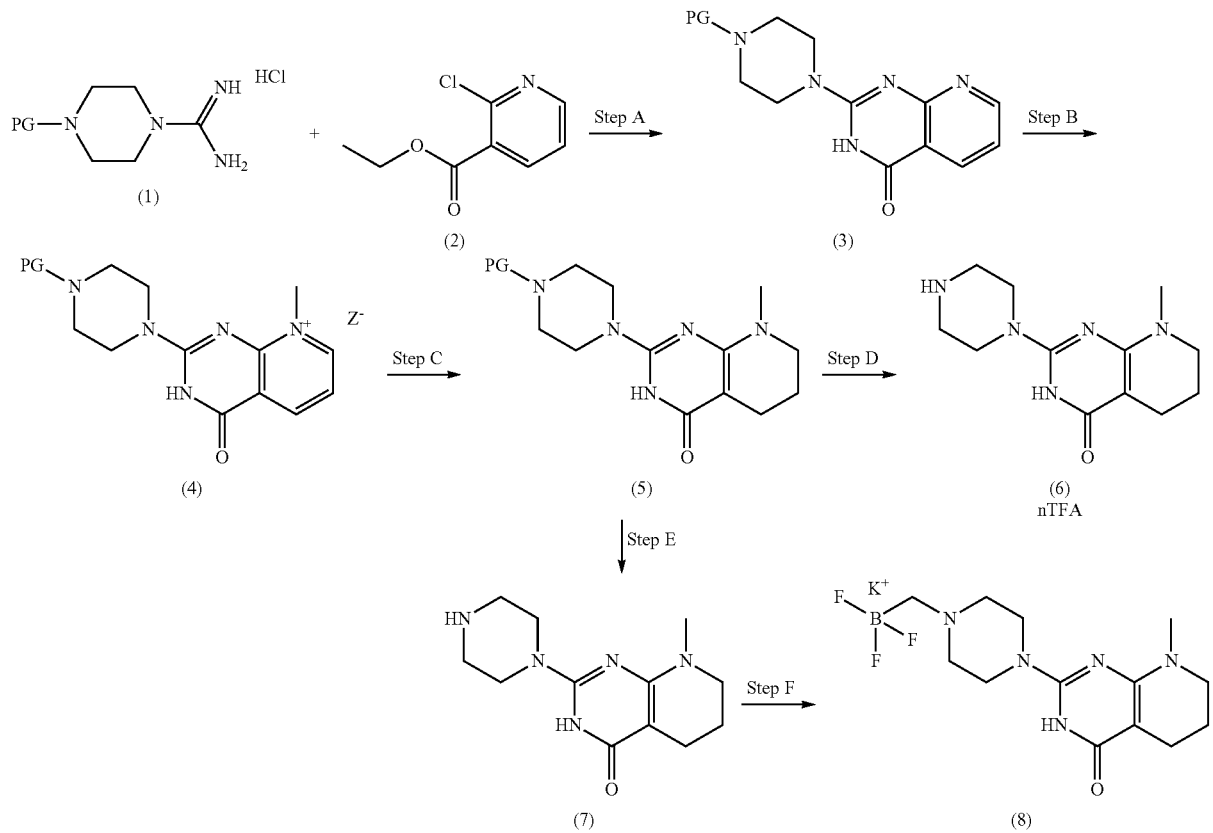

Z = I or $CH_3OSO_3$
n = 2-4 TFA
PG = Protecting Group 6,7-tetrahydropyrido[2,3-d]pyrimidin-4-one (5). The reduction can be accomplished using a reducing agent, such as sodium cyanoborohydride in a mixture of DMF/TFA of about 10/1. The TFA and reducing agent are added at a temperature of 0-5° C. with the temperature not allowed to rise above 15° C. The reaction is then allowed to go about 12 to 24 h at RT. Additional amounts of TFA and reducing agent can be added with cooling to drive the reaction to completion.

Alternatively, Step C can be accomplished by reducing the methyl sulfate salt (4, Z is $CH_3OSO_3$) with a reducing agent such as platinum oxide and hydrogenating at about 155 psi in a polar solvent such as MeOH to give compound (5).

In Step D, the piperazinyl ring is deprotected to provide 8-methyl-2-piperazin-1-yl-3,5,6,7-tetrahydropyrido[2,3-d]pyrimidin-4-one (6). Acidic conditions for removal of protecting groups such as BOC are well known in the art. Preferred conditions use a 1/1 mixture of DCM and TFA at RT for a period of 2 to 24 h to give the product as a TFA salt with 2-4 equivalents of TFA present. The salt form is not characterized but is calculated by weight.

Step E shows the deprotection of the protecting group as discussed above to give the TFA salt which can be neutralized with an ion exchange resin or an SCX column using ammonia/MeOH to give the neutral material (7). The nitrogen of the pyrazine ring can be converted to the methyl trifluoroboranate salt using potassium bromomethyl trifluoroborate in a solvent such as THF to give a salt form as shown in Step F, compound 8.

salt (6) or neutral amine (7) can be used in reductive alkylations or alkylation to give compounds of Formula I. Reductive alkylations are well known in the art and involve the reaction of an aldehyde with an amine using a reducing agent such as sodium cyanoborohydride in an appropriate solvent such as DMF at room temperature or other reducing agents such as sodium triacetoxyborohydride in an appropriate solvent such as DCM at room temperature. A catalytic amount of methanol can be used if desired with DMF and sodium cyanoborohydride to push the reaction forward faster. An appropriate aryl methyl halide can be used to alkylate the TFA amine salt (6) or neutral material (7) using an appropriate organic base such as triethylamine or an inorganic base such as potassium carbonate in a solvent such as acetonitrile or DCM. Sodium iodide can be used in situ to convert a chloromethyl substrate to a more reactive iodo methyl substrate to complete the alkylation of the appropriate pyrazine, pyridine, or pyrimidine. The reactions can be stirred at room temperature for 1-3 days to give compounds of Formula I.

Compound (8) can be coupled with aryl halides under Suzuki palladium catalyzed cross coupling conditions to form N-methyl heteroaryl substituted products. Compound 8 the methyl trifluoroboranate salt, provides another variation to prepare compounds of Formula I. The skilled artisan will recognize that there are a variety of conditions useful for facilitating such cross-coupling reactions. Accordingly, a suitable palladium reagent includes palladium(II) acetate and a suitable organophosphorus reagent such as X-phos with a base such as cesium carbonate, sodium carbonate, Scheme 2

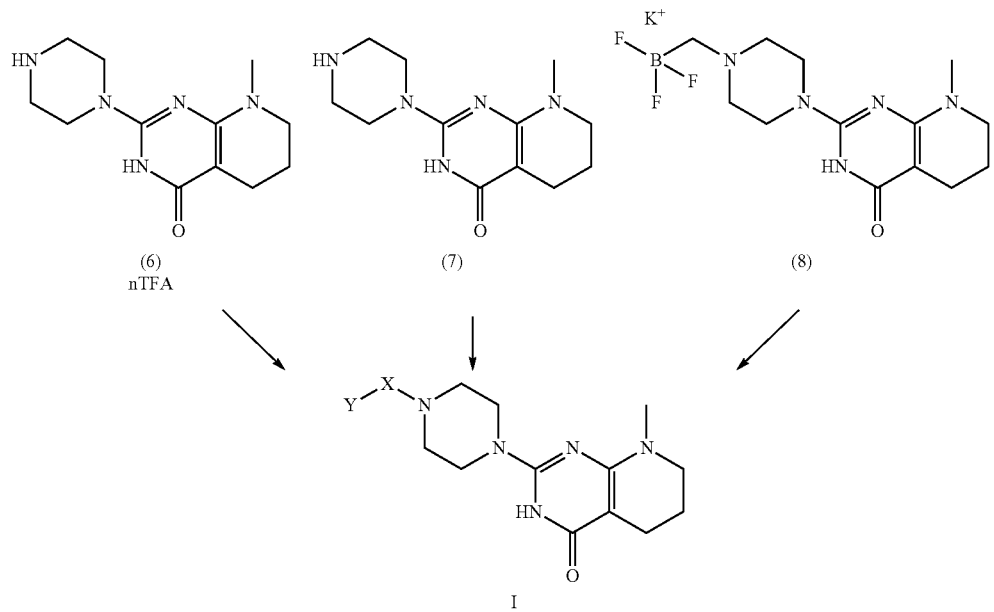

Scheme 2 illustrates the formation of compounds of Formula I from the salt form (6), the neutral material (7), or the methyl trifluoro boranate salt (8). There are many ways to form compounds of Formula I from the intermediates (6), (7), and (8) such as alkylation, reductive alkylation, or Suzuki couplings depending on the availability or synthesis of appropriate aldehydes or ketones for reductive alkylations, appropriate halide reagents for alkylations or boronic acid reagents for Suzuki couplings. The TFA amine potassium carbonate, or potassium phosphate tribasic monohydrate. Other suitable organophosphorus and palladium reagents include bis(triphenylphosphine)palladium(II) chloride, tris(dibenzylideneacetone)dipalladium (0) with tricyclohexylphosphine, (1,1'-bis(diphenylphosphino)ferrocene) palladium(II) chloride, or palladium tetrakistriphenylphosphine.

In an optional step, a pharmaceutically acceptable salt of a compound of Formula I, such as a hydrochloride salt, can be formed by reaction of a free base compound of Formula I with an appropriate acid in a suitable solvent under standard conditions. Additionally, the formation of such salts can occur simultaneously upon deprotection of a nitrogen protecting group.

The following preparations and examples further illustrate the invention. Unless noted to the contrary, the compounds illustrated herein are named and numbered using Accelrys® Draw version 4.0 (Accelrys, Inc., San Diego, Calif.), IUPACNAME ACDLABS, or ChemDraw® Ultra 12.0.

General Method Description of Reverse Phase Purification

System: Agilent 1200 LCM/MS equipped with Mass Selective Detector (MSD) mass spectrometer and Leap autosampler/fraction collector; Column: 75×30 mm Phenomenex Gemini-NX, 5μ particle size column with 10×20 mm guard; Solvent System: A: 10 mM ammonium bicarbonate, pH 10 as the aqueous phase, B: ACN as the organic phase; Flow rate: 85 mL/min; Method: The gradient for each method is designated in the method name as the beginning % B-ending % B (e.g. as in High pH 13-48). The gradient is set as follows: 0-1 min (hold at begin % B), 1-8 min (gradient from begin % B to end % B), 8-8.1 min (ramp from end % B to 100% B), 8.1-9 min (hold 100% B).

Preparation 1

4-Methoxypyrimidine-2-carbaldehyde

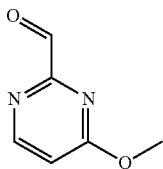

Combine 4-methoxypyrimidine-2-methanol (300 mg, 2.14 mmol) and oxalyl chloride (1 mL, 2.0 M in DCM) in DCM (5 mL) and cool to −78° C. Add DMSO (0.33 mL, 4.71 mmol) and stir the mixture for 2 h. Add triethylamine (0.66 mL, 4.71 mmol) and warm the mixture to room temperature overnight. Add water (5 mL), stir 1 h and extract with DCM (2×50 mL). Dry the combined organic extracts over sodium sulfate, filter, and concentrate the filtrate under reduced pressure to give a light brown solid and used without further purification. $^1$H NMR (400 MHz, CDCl$_3$) δ aldehyde peak 9.94 (s, 1H), remaining peaks not assignable due to the mixture of more than one compound.

Preparation 2

4-Methylpyrimidine-2-carbaldehyde

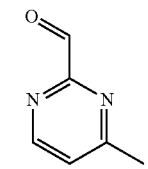

Prepare 4-methylpyrimidine-2-carboxaldehyde essentially as described in Preparation 1 using (4-methylpyrimidin-2-yl)methanol to obtain the title compound and use without further purification. $^1$H NMR, 400 MHz, CDCl$_3$) δ 10.06 (s, 1H), 8.79 (d, 1H, J=5.2 Hz), 7.33 (d, 1H, J=4.8 Hz), 2.65 (s, 3H)

Preparation 3

4-(Trifluoromethyl)-2-vinyl-pyrimidine

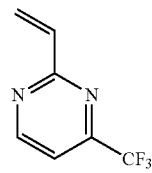

Combine 2-chloro-4-(trifluoromethyl)pyrimidine (250 mg, 1.37 mmol), potassium vinyltrifluoroborate (184 mg, 1.37 mmol), cesium carbonate (1.34 g, 4.11 mmol), THF (5 mL) and water (0.5 mL) in a vial. Degas with a stream of nitrogen for 1 min. Add bis(triphenylphosphine)palladium (II) chloride (48 mg, 0.069 mmol), seal the vial, and heat the mixture at 85° C. for 3 days. Cool, dilute the mixture with DCM, filter through diatomaceous earth, and concentrate the filtrate under reduced pressure to give the title compound (0.200 g, 84%) which is used without further purification. $^1$H NMR (400 MHz, CDCl$_3$) δ 8.93 (d, 1H, J=5.0 Hz), 7.43 (d, 1H, J=5.0 Hz), 6.94 (ABX, 1H, $J_{AX}$=17.3, $J_{BX}$=10.47), 6.74 (ABX, 1H, $J_{AB}$=1.54, $J_{AX}$=17.3), 5.84 (ABX, 1H, $J_{AB}$=1.54, $J_{BX}$=10.47).

Preparation 4

5-Methyl-2-vinyl-pyrimidine

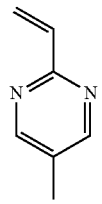

Prepare the title compound essentially as described in Preparation 3 using 2-choro-5-methylpyrimidine and use without further purification (220 mg, 94%). $^1$H NMR (400 MHz, CDCl$_3$) δ 8.38 (s, 2H), 6.73 (ABX, 1H, $J_{AX}$=17.4, $J_{BX}$=10.7), 6.41 (ABX, 1H, $J_{AB}$=1.8, $J_{AX}$=17.4), 5.54 (ABX, 1H, $J_{AB}$=1.8, $J_{BX}$=10.7), 2.16 (s, 3H).

Preparation 5

4-(Trifluoromethyl)pyrimidine-2-carbaldehyde

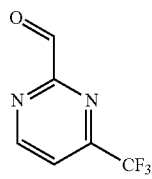

Combine 4-(trifluoromethyl)-2-vinyl-pyrimidine (200 mg, 0.84 mol) with sodium periodate (737 mg, 3.45 mmol) and osmium tetroxide, polymer bound (292 mg, 0.057 mmol) in dioxane (3 mL) and water (1 mL) and stir mixture at room temperature overnight. Dilute the mixture with EtOAc (5 mL) and water (5 mL). Filter the mixture through glass wool and separate the layers. Dry the organic layer over magnesium sulfate, filter, and concentrate the filtrate to give the title compound (40 mg, 20%). Use the crude material without further purification. $^1$H NMR (400 MHz, CDCl$_3$) δ aldehyde 10.16 (s, 1H), remaining peaks not assignable due to the mixture of more than one compound.

Preparation 6

5-Methylpyrimidine-2-carbaldehyde

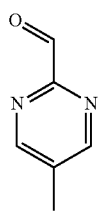

Prepare 5-methylpyrimidine-2-carbaldehyde essentially as described in Preparation 5, using 2-chloro-5-methyl-pyrimidine to give the title compound (90 mg, 44%) and use without further purification. $^1$H NMR (400 MHz, CDCl$_3$) δ 10.06 (s, 1H), 8.79 (s, 2H), 2.42 (s, 3H).

Preparation 7

2-(Bromomethyl)-4-chloro-pyrimidine

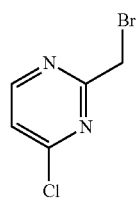

Combine 2-methyl-4-chloropyrimidine (200 mg, 1.55 mmol), carbon tetrachloride (5 mL), N-bromosuccinimide (304 mg, 1.71 mmol), and benzoyl peroxide (38 mg, 1.6 mmol) in a vial, flush with nitrogen for 2 min, seal and heat at 80° C. overnight. Use the crude reaction mixture without further purification. GC-MS m/e: ($^{79}$BR/$^{81}$Br 205/207 (M$^+$).

Preparation 8

2-(Chloromethyl)pyrazine

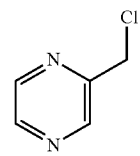

Dissolve 2-pyrazinylmethanol (2.0 g, 18.1 mmol) in DCM (200 mL) and cool to 0° C. while stirring under nitrogen. Add thionyl chloride (4.63 mL, 63.6 mmol) drop wise over 10 min, and allow to warm to 25° C. Stir at room temperature for 16 h. Concentrate the mixture and then dilute with DCM. Wash the crude solution with saturated NaHCO$_3$, dry over MgSO$_4$, filter, and concentrate. Dissolve the crude residue in DCM and purify by silica gel flash chromatography (hexane/EtOAc, 95:5 to 100% EtOAc gradient) to give the title compound as a pale yellow oil. $^1$H NMR (400 MHz, CDCl$_3$) δ 4.67 (s=2H), 8.50-8.55 (m, 2H), 8.73 (s, 1H).

Preparation 9

2-(Bromomethyl)-3-chloro-pyrazine

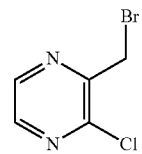

Add together 2-chloro-3-methyl-pyrazine (5.0 g, 38.9 mmol), N-bromosuccinimide (6.92 g, 38.9 mmol), benzoyl peroxide (0.471 g, 1.94 mmol), and carbon tetrachloride (50 mL) and heat at reflux under nitrogen for 16 h. Cool the reaction mixture to 25° C. and dilute with hexanes. Filter the mixture, concentrate the liquid under reduced pressure, and purify by silica gel flash chromatography (hexane/EtOAc, 95:5 with gradient to 40:60) to give the title compound as a brown oil (3.93 g, 49%). $^1$H NMR (400 MHz, CDCl$_3$) δ 4.66 (s=2H), 8.32 (d, J=2.4 Hz, 1H), 8.47 (d, J=2.4 Hz, 1H).

Preparation 10

Methyl 3,5-difluoropyridine-2-carboxylate

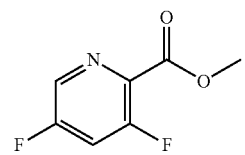

Add together 3,5-difluoropyridine-2-carboxylic acid (1.4 g, 8.8 mmol) and DCM (30 mL) and cool to 0° C. Add MeOH (3 mL), DMAP, (1.32 g, 10.6 mmol) and EDCI (2.1 g, 10.6 mmol). Allow mixture to warm to room temperature and stir overnight. Concentrate the reaction mixture under reduced pressure and purify the residue by chromatography on silica gel (elution with 10/1 petroleum ether/EtOAc) to give the title compound (1.03 g, 72%). LC-ES/MS m/z 174 (M+H)$^+$.

Preparation 11

(3,5-Difluoro-2-pyridyl)methanol

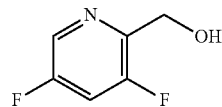

Add together methyl 3,5-difluoropyridine-2-carboxylate (1.0 g, 4.6 mmol), THF (10 mL) and 2 M lithium borohydride in THF (15 mL, 23 mmoL). Stir the mixture at room temperature for 2 days. Concentrate under reduced pressure and purify the residue by silica gel chromatography eluting with DCM to give the title compound (0.448 g, 60%).

Preparation 12

2-(Chloromethyl)-3,5-difluoropyridine

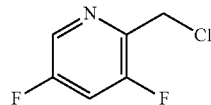

Add together (3,5-difluoro-2-pyridyl)methanol (200 mg, 1.4 mmol), DCM (4 mL), DMF (0.1 mL) and thionyl chloride (1 mL) and stir the mixture for 4 hours. Adjust the pH to about 7.0 with 4 M aqueous sodium bicarbonate and extract the mixture with DCM (3×50 mL). Combine the organic portions, dry over anhydrous sodium sulfate, filter, and concentrate to give the title compound (182 mg, 81%) as an orange oil.

Preparation 13 tert-Butyl 4-carbamimidoylpiperazine-1-carboxylate hydrochloride

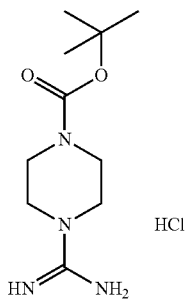 [SMILES: CC(C)(C)OC(=O)N1CCN(C(=N)N)CC1 ; Cl]

Charge a 10 L jacketed reactor with tert-butyl piperazine-1-carboxylate (1500 g, 8.054 mol) and DMF (4.05 L). Stir until a solution is obtained. Add 1H-pyrazole-1-carboxamide HCl (1180 g, 8.054 mol) followed by diisopropylamine (1041 g, 8.054 mol) over 15 min at 22 to 28° C. Heat at 55 to 60° C. for 5 h and then cool to 20° C. Transfer the reaction mixture to a 50 L jacketed reactor containing TBME (30 L) over 15 to 20 minutes and rinse the transfer lines with DMF (400 mL). Stir the suspension for 1 hour at 20° C. and then filter through three separate 26 cm Buchner funnels. Wash each product cake with TMBE (2×1000 mL) and dry in a vacuum oven at 60° C. overnight to give the title compound (1898 g, 89%) as a white solid. $^1$H NMR (400 MHz, DMSO-d$_6$) δ 1.41 (s, 9H), 3.42-3.50 (m, 4H), 3.33-3.42 (m, 4H), 7.77 (s, 4H).

Preparation 14 tert-Butyl 4-(4-oxo-3H-pyrido[2,3-d]pyrimidin-2-yl)piperazine-1-carboxylate

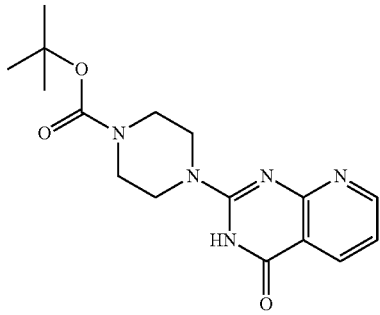 [SMILES: CC(C)(C)OC(=O)N1CCN(c2nc3ncccc3c(=O)[nH]2)CC1]

Charge a 22 L round bottom flask with tert-butyl 4-carbamimidoylpiperazine-1-carboxylate hydrochloride (1897 g, 7.165 mol), DMF (10.1 L), and ethyl 2-chloronicotinate (1266 g, 6.824 mol). Add potassium tert-butoxide (1293 g, 11.52 mol) portion-wise over 55 min while allowing the temperature to rise gradually from 17 to 62° C. Heat the reaction at 100° C. for 2.5 h. -Cool the reaction mixture to 20° C. and transfer to a 30 L jacketed reactor containing water (15.2 L) using DMF (350 mL) to rinse the reactor and transfer lines. Introduce 3 N hydrochloric acid (1.52 L) until a pH of 5 to 6 is obtained and stir the suspension for 2 hours at 20° C. Collect the product by filtration through three separate 26 cm Buchner funnels and wash each cake with water (3×1.5 L). Combine the cakes, suspend them in water (15.0 L), and stir for 60 min at 20° C. Collect the product by filtration through two separate 26 cm Buchner funnel and wash the cake with water (2×1.5 L). Dry the solid in a vacuum oven at 60° C. for 24 hours to give the title compound (1332 g, 59%) as a yellow solid. $^1$H NMR (400 MHz, DMSO-d$_6$) δ 1.43 (s, 9H), 3.36-3.49 (m, 4H), 3.62-3.76 (m, 4H), 7.13-7.20 (m, 1H), 8.22-8.27 (m, 1H), 8.62-8.70 (m, 1H).

Preparation 15 tert-Butyl 4-(8-methyl-4-oxo-3H-pyrido[2,3-d]pyrimidin-8-ium-2-yl)piperazine-1-carboxylate, methyl sulfate

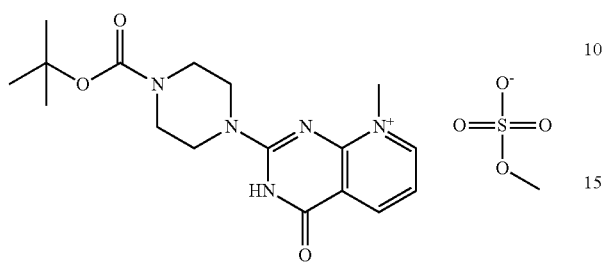

Charge a 20 L jacketed reactor with tert-butyl 4-(4-oxo-3H-pyrido[2,3-d]pyrimidin-2-yl)piperazine-1-carboxylate (1331 g, 4.017 mol) and DMF (6.66 L). Add dimethylsulfate (583 g, 2.83 mol) over 5-10 min and observe a slight exotherm to 38° C. Heat the solution to 63 to 73° C. for 30 minutes Then introduce additional dimethylsulfate (50.7 g, 0.402 mol) and heat at 68 to 73° C. for 30 min Sample of the reaction shows 2.0% starting material remaining Add additional dimethylsulfate (50.7 g, 0.402 mol) and heat at 68 to 73° C. Sample again to show 1.3% staring material remaining Cool the reaction to 20° C. and transfer over 20 to 30 minutes to a 50 L jacket reactor containing TBME (26.6 L), tert-butyl 4-(8-methyl-4-oxo-3H-pyrido[2,3-d]pyrimidin-8-ium-2-yl)piperazine-1-carboxylate and seeds (1 g) using DMF (300 mL) to rinse the reactor and transfer lines. Stir the suspension overnight at 20° C. overnight and collect the product by filtration using three separate 26 cm Buchner funnels. Rinse each cake with TBME (3×1.3 L), Combine the three portions and suspend the material in TMBE (13.3 L), stir for 1 h at 20° C., and collect the product on two separate 26 cm Buchner funnel. Wash each cake with TBME (3×2.0 L) and dry in a vacuum oven at 55 to 60° C. for 16 hours to give the title compound (1812 g, 98%) as a yellow solid. $^1$H NMR (400 MHz, DMSO-$d_6$) δ 1.44 (s, 9H), 3.37 (s, 3H), 3.45-3.55 (m, 4H), 3.80-3.95 (m, 4H), 4.08 (s, 3H), 7.40-7.45 (m, 1H), 8.72-8.76 (m, 1H), 8.86-8.91 (m, 1H)

Preparation 15 Seed Crystal Formation

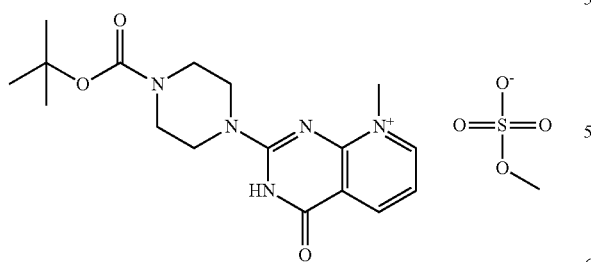

Charge a 250 mL reactor with tert-butyl 4-(4-oxo-3H-pyrido[2,3-d]pyrimidin-2-yl)piperazine-1-carboxylate (15 g, 45.3 mmol) and dimethylformamide (75 mL). Add dimethylsulfate (6.28 g, 49.8 mmol) in one portion to the stirring mixture (observe slight exotherm to 34° C.). Heat the resulting solution at 68 to 73° C. for 3 hours. Add dimethylsulfate (0.57 g, 4.5 mmol) and stir at 68 to 73° C. for an additional 1 hour. Cool to 20° C. and transfer drop wise to a 1 L flask containing TBME (300 mL). Observe the sticky solid change to stirrable suspension, stir overnight at 20° C. and filter on a Buchner funnel. Wash the product cake with TBME (3×35 mL) and suspend in TBME (100 mL). Stir the suspension for 1 hour at 20° C., filter on a Buchner funnel and wash the cake with TBME (2×35 mL). Dry the solids in a vacuum oven at 55 to 60° C. for 16 hours to give tert-Butyl 4-(8-methyl-4-oxo-3H-pyrido[2,3-d]pyrimidin-8-ium-2-yl)piperazine-1-carboxylate, methyl sulfate (18.84 g, 91% yield) (HPLC purity 95%).

Preparation 16 tert-Butyl 4-(8-methyl-4-oxo-3H-pyrido[2,3-d]pyrimidin-8-ium-2-yl)piperazine-1-carboxylate iodide

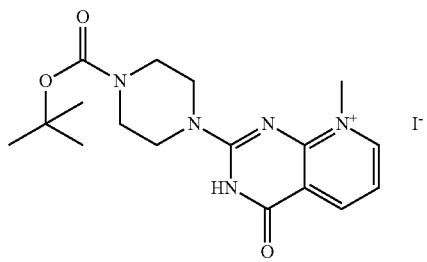 [SMILES: C[n+]1cccc2c(=O)[nH]c(N3CCN(C(=O)OC(C)(C)C)CC3)nc21 ; [I-]]

Combine tert-butyl 4-(4-oxo-3H-pyrido[2,3-d]pyrimidin-2-yl)piperazine-1-carboxylate (115.43 g), THF (1.4 L), and methyl iodide (24 mL) in a 2 L Parr autoclave with mechanical stirrer. Seal the autoclave and stir the reaction with heating at 70° C. for 22 hours. Cool the reaction to room temperature and transfer the resulting bright yellow slurry to a round bottom flask using MeOH. Concentrate the slurry and dry the resulting solid in a vacuum oven at 50-60° C. to give the title compound as a yellow solid (167.44 g, 100%). LC-ES/MS m/z 346.2 [M+H]$^+$, $T_R$=1.16 min.

Preparation 17 tert-Butyl 4-(8-methyl-4-oxo-3,5,6,7-tetrahydropyrido[2,3-d]pyrimidin-2-yl)piperazine-1-carboxylate

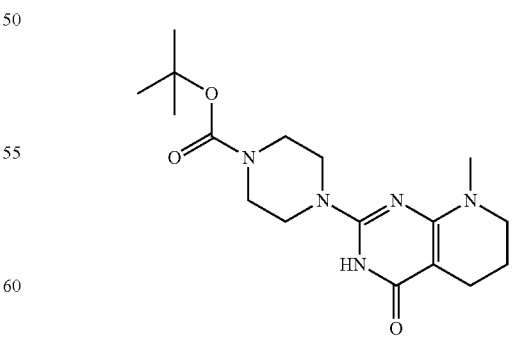

Charge a 2 gallon pressure vessel with tert-butyl 4-(8-methyl-4-oxo-3H-pyrido[2,3-d]pyrimidin-8-ium-2-yl)piperazine-1-carboxylate, methyl sulfate (881 g, 1.927 mol) and MeOH (4.9 L). Add platinum oxide (1% w/w, 8.81 g) and pressurize with hydrogen to 155 psi. Stir for 4 hours at 22-28° C. Filter through a filter cartridge to collect the catalyst. Set aside the filtrate to be combined with the filtrate of a second hydrogenation. Repeat the reaction on another portion of tert-butyl 4-(8-methyl-4-oxo-3H-pyrido[2,3-d]pyrimidin-8-ium-2-yl)piperazine-1-carboxylate, methyl sulfate (925 g, 2.023 mol), MeOH (5.0 L) and platinum oxide (1% w/w, 9.25 g) as before filter and combine the two filtrates and concentrate to an oily residue. Dissolve the residue in DCM (9.3 L) and wash with 0.1 N aqueous HOAc (2×2.0 L and 2×1.1 L) and 0.5 M NaOH (8.0 L). Add water (4.0 L) and adjust to pH 6-7 with 0.1 N aqueous HOAc (about 1.9 L). Separate the layers and dry the organic layer over magnesium sulfate, filter, and concentrate to a volume of about 4.5 L and add EtOAc (16.0 L) to crystallize the product. Concentrate the suspension to a volume of about 4.5 L, cool to 0 to 5° C. and collect the product by filtration. Wash the cake with EtOAc (2×2.0 L and 2×1.1 L) and dry in a vacuum oven at 55 to 65° C. for 16 h to give the title compound (1185 g, 77%) as a white solid (very electrostatic). $^1$H NMR (400 MHz, CDCl$_3$) δ 1.45 (s, 9H), 1.76-1.88 (m, 2H), 2.53 (t, J=6.3 Hz, 2h), 3.04 (s, 3H), 3.20-3.26 (m, 2H), 3.40-3.52 (m, 4H), 3.60-3.70 (m, 4H), 5.01 (s, 1H), 12.1-12.3 (br s, 1H). $^{13}$C NMR (101 MHz, CDCl$_3$) δ 20.00, 21.63, 28.81, 36.55, 44.99, 50.20, 80.38, 85.85, 152.38, 155.15, 160.14, 164.03. ESI/MS m/z 350.0 [M+H]$^+$.

Preparation 17

Alternative Synthesis

Charge a round bottom flask with tert-butyl 4-(8-methyl-4-oxo-3H-pyrido[2,3-d]pyrimidin-8-ium-2-yl)piperazine-1-carboxylate iodide (167.44 g, 353.76 mmol) and DMF (815 mL) and cool in an ice bath to an internal temperature of 0-5° C. Add trifluoroacetic acid (80.25 mL, 1.06 mol) at a rate to maintain the internal temperature below 15° C. (45 min) Cool the reaction to an internal temperature of 0-5° C. and add sodium cyanoborohydride (66.69 g, 1.06 mol) at a rate to maintain the temperature below 15° C. (about 50 min) Stir the reaction for 18 h while warming to 25° C. Cool the reaction back down to 0-5° C. and add trifluoroacetic acid (80.25 mL, 1.06 mol) at a rate to maintain the temperature below 15° C. (10 min) followed by sodium cyanoborohydride (66.69 g, 1.06 mol) at a rate to maintain the temperature below 15° C. (10 min). Stir the reaction overnight while warming to 25° C. Cool the reaction back down to 0-5° C. and add trifluoroacetic acid (26.6 mL, 0.345 mol) at a rate to maintain the temperature below 10° C. (5 min) followed by sodium cyanoborohydride (22.3 g, 0.345 mol) in two portions over 10 min. Stir overnight while warming to 25° C. Fit a 12 L bucket with an overhead stirrer and charge it with sodium bicarbonate (297.18 g, 3.54 mol) and water (7.2 L). Add the crude reaction mixture to the bicarbonate solution using a separatory funnel over a period of 30 min and observe gas evolution. Stir the mixture for 2 hours and then let sit at 25° C. overnight. Collect the resulting solid by filtration and rinse with water and diethyl ether. Dry the solid in a vacuum oven at about 60° C. overnight to give the title compound (111.34 g, 90%) as a beige solid. LC-ES/MS m/z 350.0 [M+H]$^+$, T$_R$=1.93 min.

Preparation 18

8-Methyl-2-piperazin-1-yl-3,5,6,7-tetrahydropyrido[2,3-d]pyrimidin-4-one bis-(2,2,2-trifluoroacetic acid) salt

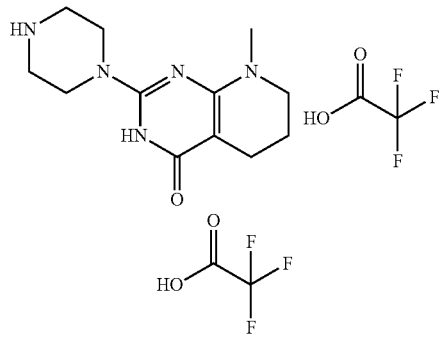

Add together tert-butyl 4-(8-methyl-4-oxo-3,5,6,7-tetrahydropyrido[2,3-d]pyrimidin-2-yl)piperazine-1-carboxylate (46.8 g, 133.9 mmol) and DCM (100 mL). Add trifluoroacetic acid (80 mL, 1.09 moles) over 15 min and stir at 25° C. overnight. Concentrate under reduced pressure, add DCM (200 mL), and re-concentrate under reduced pressure four times to give the title compound as an off white solid (69.685 g, 100% crude). LC-ES/MS m/z 250.0 [M+H]$^+$, T$_R$=0.53 min.

Preparation 19

8-Methyl-2-piperazin-1-yl-3,5,6,7-tetrahydropyrido[2,3-d]pyrimidin-4-one; tri-2,2,2-trifluoroacetic acid

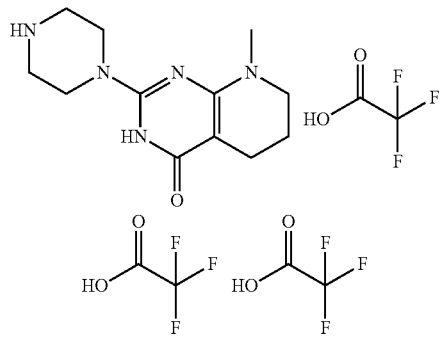

Add together tert-butyl 4-(8-methyl-4-oxo-3,5,6,7-tetrahydropyrido[2,3-d]pyrimidin-2-yl)piperazine-1-carboxylate (196.0 g, 560.8 mmol) and DCM (783 mL). Cool the cloudy suspension in an ice bath to an internal temperature of 4° C. and add trifluoroacetic acid (254 mL) over 10 min while stirring. Stir for 42 hours at room temperature. Remove the volatiles under reduced pressure and dissolve in DCM. Remove the volatiles under reduced pressure and dry under vacuum at 40° C. overnight to give the title compound (431.5 g, 99%) as a white solid. $^1$H NMR (300 MHz, DMSO-d6) δ 8.96 (br s, 2H), 7.49 (br s, TFA/water, 9H), 3.78 (t, 4H, J=5 Hz), 3.29 (t, 2H, J=5 Hz), 3.15 (br s, 4H), 3.04 (s, 3H), 2.37 (t, 2H, J=6.3 Hz), 1.76 (pt, 2H, J=5.8 Hz

Preparation 20

8-Methyl-2-piperazin-1-yl-3,5,6,7-tetrahydropyrido[2,3-d]pyrimidin-4-one; tetra-2,2,2-trifluoroacetic acid

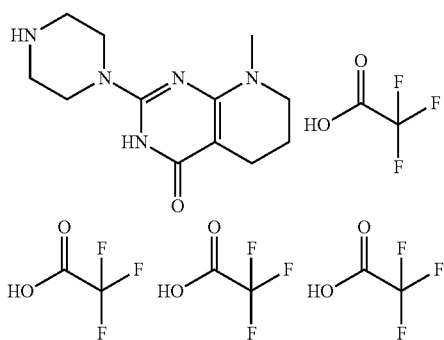

Add together tert-butyl 4-(8-methyl-4-oxo-3,5,6,7-tetrahydropyrido[2,3-d]pyrimidin-2-yl)piperazine-1-carboxylate (0.29 g, 0.83 mmol), DCM (3 mL) and trifluoroacetic acid (3 mL). Stir the reaction at room temperature for 4 hrs. Concentrate the mixture and dissolve the residue in DCM (2×) and concentrate the mixture. Dry under vacuum for 1 hour to give the title compound (0.556 g, 95%) which is used without purification or characterization.

Preparation 21

8-Methyl-2-piperazin-1-yl-3,5,6,7-tetrahydropyrido[2,3-d]pyrimidin-4-one

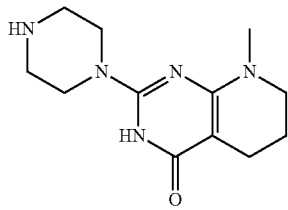 [SMILES: CN1CCCc2c1nc(N1CCNCC1)[nH]c2=O]

Charge a round bottom flask with tert-butyl 4-(8-methyl-4-oxo-3,5,6,7-tetrahydropyrido[2,3-d]pyrimidin-2-yl)piperazine-1-carboxylate (730 mg, 1.53 mmol), DCM (15 mL) and trifluoroacetic acid (15 mL) and stir the reaction at room temperature for 3 hours. Concentrate under reduced pressure, dissolve the residue in methanol, add ion-exchange resin Dowex® 50WX4-400 (5.5 g), and stir the mixture at room temperature overnight. Filter the mixture and wash the ion exchange resin with 7 M ammonia in methanol. Combine the filtrate and washings, and concentrate under reduce pressure to give the title compound as an orange solid (385 mg, 95%). LC-ES/MS m/z 250 [M+H]$^+$.

Alternate Preparation 21

Prewash a 10 g SCX-2 column with DCM (30 mL) and load with a solution of 8-methyl-2-piperazin-1-yl-3,5,6,7-tetrahydropyrido[2,3-d]pyrimidin-4-one bis-(2,2,2-trifluoroacetic acid) (0.5 g, 1.05 mmol) in DCM (10 mL) and MeOH (1 mL). Wash the column with DCM (30 mL), followed by MeOH (30 mL), and elute with 2 M NH$_3$/MeOH (60 mL). Concentrate the fractions containing the product under reduced pressure to give the title compound (0.26 g, 100%).

Preparation 22

Potassium trifluoro-[[4-(8-methyl-4-oxo-3,5,6,7-tetrahydropyrido[2,3-d]pyrimidin-2-yl)piperazin-1-yl]methyl]boranuide

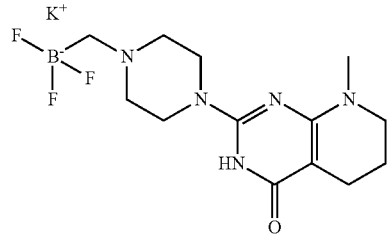 [SMILES: [K+] ; CN1CCCc2c1nc(N1CCN(C[B-](F)(F)F)CC1)[nH]c2=O]

Dissolve 8-methyl-2-piperazin-1-yl-3,5,6,7-tetrahydropyrido[2,3-d]pyrimidin-4-one (250 mg, 1.00 mmol) in THF (4 mL) and add potassium bromomethyl trifluoroborate (208 mg, 1.00 mmol). Heat at 80° C. for 90 min and then concentrate under a stream of nitrogen. Add acetone (30 mL) and potassium bicarbonate (100 mg, 1.00 mmol) and stir at room temperature overnight. Remove the solids by filtration and concentrate the filtrate under reduced pressure to give the title compound (273 mg, 73%) as an off-white solid. ES/MS m/z 330 [M-K$^+$]$^-$.

EXAMPLE 1

8-Methyl-2-[4-(pyrimidin-2-ylmethyl)piperazin-1-yl]-3,5,6,7-tetrahydropyrido[2,3-d]pyrimidin-4-one

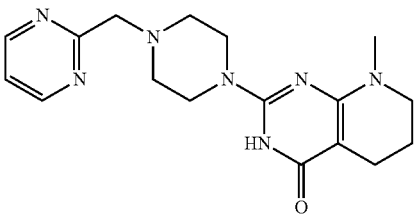 [SMILES: CN1CCCc2c1nc(N1CCN(Cc3ncccn3)CC1)[nH]c2=O]

Dissolve 8-methyl-2-piperazin-1-yl-3,5, 6,7-tetrahydropyrido[2,3-d]pyrimidin-4-one; tri-2,2,2-trifluoroacetic acid (409 g, 531 mmol) in DCM (2.0 L) in a 5 L extraction funnel. Purge the funnel with nitrogen and equip it with an overhead mechanical stirrer. Add pyrimidine-2-carboxaldehyde (66.6 g, 616 mmol) and stir for 40 min. Then add sodium triacetoxyborohydride (225.1 g, 1060 mmol) portion wise and observe an exotherm from 20 to 36° C. immediately after the addition. Stir the reaction at room temperature overnight. Pour the reaction carefully into 1 M NaOH (2.32 L) at 20° C. in a 10 L reactor while controlling the resulting exotherm with a chiller. Adjust the pH to 8 to 9 with 1 N NaOH (2.55 L). Collect the organic layer and extract the aqueous layer with DCM (2.32 L). Combine the organic layers, concentrate and dry under a stream of nitrogen overnight to give the title compound (193 g, 100% crude product). $^1$H NMR (300 MHz, DMSO-d6) δ (br s, 1H), 8.78 (d, 2H, J=5.5 Hz), 7.41 (t, 1H, J=4.9 Hz), 3.76 (s, 2H), 3.52 (br s, 4H), 3.187 (t, 2H, J=5.2 Hz), 2.96 (s, 3H), 2.54 (m, 2H), 2.28 (t, 2H, J=6 Hz), 1.72 (pt, 2H, J=5.2 Hz). This lot is combined with 4 other lots for purification (203 g). Purify by silica filtration (20 cm diameter by 8 cm high) and elute with 90% DCM/10% 2 M NH$_3$ in MeOH to give the title compound (162 g, 84%). $^1$H-NMR (300 MHz, CDCl$_3$): δ 8.74 (d, J=5.1 Hz, 2H), 7.20 (t, J=5.1 Hz, 1H), 3.85 (s, 2H), 3.78-3.69 (m, 4H), 3.27-3.19 (m, 2H), 3.03 (2, 3H), 2.68-2.59 (m, 4H), 2.47-2.38 (m, 2H), 1.88-1.76 (m, 2H).

EXAMPLE 1

Alternate Synthesis

Combine 8-methyl-2-piperazin-1-yl-3,5,6,7-tetrahydropyrido[2,3-d]pyrimidin-4-one tri-2,2,2-trifluoroacetic acid (203.23 g, 344 mmol), pyrimidine-2-carbaldehyde (40 g, 370 mmol) and DMF (343 mL) and stir until a homogeneous solution is obtained (30 min). Cool the solution in an ice bath and add sodium cyanoborohydride (25 g, 397 mmol) in a 5 g portion followed by a 10 g portion 5 minutes later. Stir for 1.5 hr and add the final 10 g of cyanoborohydride. Stir 30 minutes while maintaining the temperature below 25° C. Stir the reaction overnight and allow to warm 25° C. Pour the reaction mixture into a beaker (4 L) fitted with an overhead stirrer containing sodium bicarbonate (115 g, 1.37 mol) and water (350 mL). Stir the mixture for 20 min and then add EtOAc (1 L) and stir for 30 min. Pour the mixture through diatomaceous earth (700 g) over about 30 min and gravity filter for about 1 hour. Then apply vacuum and rinse the diatomaceous earth with EtOAc (2×1 L). Combine and concentrate the organic layer to give a viscous yellow oil with a crude weight of 117 g. Purify the oil by silica gel flash chromatography (DCM to 90% DCM/MeOH, gradient). Dry the resulting material in a vacuum oven at 50° C. to give the title compound as a white foamy solid (44.22 g, 38%). LC-ES/MS m/z 342.3 [M+H]$^+$, T$_R$=0.96 min.

EXAMPLE 2

2-[4-[(3-Chloro-2-pyridyl)methyl]piperazin-1-yl]-8-methyl-3,5,6,7-tetrahydropyrido[2,3-d]pyrimidin-4-one

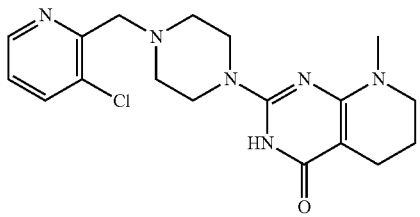 [SMILES: CN1CCCc2c1nc(N1CCN(Cc3ncccc3Br)CC1)[nH]c2=O]

Add together 8-methyl-2-piperazin-1-yl-3,5,6,7-tetrahydropyrido[2,3-d]pyrimidin-4-one; tetra 2,2,2-trifluoroacetic acid (0.556 g, 0.788 mmol), 3-chloropicolinaldehyde (557.87 mg, 3.94 mmol) in DMF (3 mL) followed by sodium cyanoborohydride (148.6 mg, 2.36 mmol). The reaction is stirred at room temperature for 5 days. Dilute the reaction with CHCl$_3$ (75 mL) and wash with saturated NaHCO$_3$ and brine. Dry over Na$_2$SO$_4$, filter, and concentrate to dryness. The crude product is purified by silica gel chromatography eluting with DCM to 90% DCM/MeOH to give the title product (214 mg, 72%). LC ES/MS m/z 375.3 ($^{35}$Cl) (M+H)$^+$.

The following Examples 3, 4 and 5 are prepared essentially following the procedure described in Example 2, using the appropriate aldehyde or ketone, stirring at room temperature for 2 hrs up to 48 hrs and monitoring reaction for completion, adding more sodium cyanoborohydride if needed and stirring for a further 24 hours.

TABLE 1

| Ex. No. | Chemical name | Structure | LC-ES/MS m/z |
|---|---|---|---|
| 3$^a$ | 2-[4-[(3-Bromo-2-pyridyl)methyl]piperazin-1-yl]-8-methyl-3,5,6,7-tetrahydropyrido[2,3-d]pyrimidin-4-one | | 419.1 ($^{79}$Br) (M + H)$^+$ |
| 4$^b$ | 2-[4-[(3-Hydroxy-2-pyridyl)methyl]piperazin-1-yl]-8-methyl-3,5,6,7-tetrahydropyrido[2,3-d]pyrimidin-4-one | | 357.2 (M + H)$^+$ |

TABLE 1-continued

| Ex. No. | Chemical name | Structure | LC-ES/MS m/z |
|---|---|---|---|
| 5[c] | 8-Methyl-2-[4-[1-[5-(trifluoromethyl)pyrimidin-2-yl]ethyl]piperazin-1-yl]-3,5,6,7-tetrahydropyrido[2,3-d]pyrimidin-4-one | 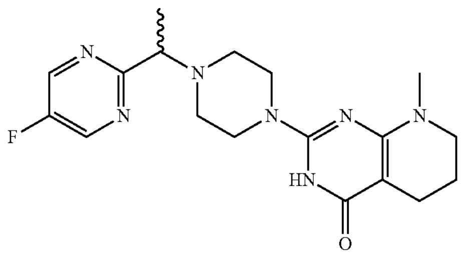 [SMILES: CC(c1ncc(F)cn1)N1CCN(c2nc3c(c(=O)[nH]2)CCCN3C)CC1] | 374.2 (M + H)[+] |

[a]MeOH (1 mL) added in addition to DMF as solvent.
[b]Dichlormethane is solvent and sodium triacetoxyborohydride is used instead of sodium borohydride.
[c]MeOH is solvent.

EXAMPLE 6

8-Methyl-2-[4-(pyrimidin-2-ylmethyl)piperazin-1-yl]-3,5,6,7-tetrahydropyrido[2,3-d]pyrimidin-4-one 4-methylbenzenesulfonic acid salt

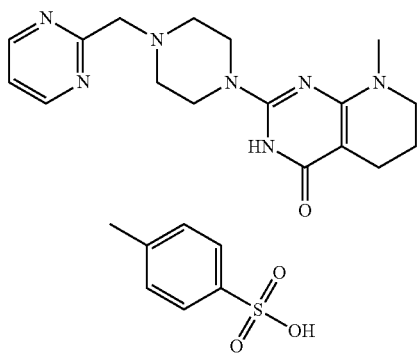

Add 8-methyl-2-[4-(pyrimidin-2-ylmethyl)piperazin-1-yl]-3,5,6,7-tetrahydropyrido[2,3-d]pyrimidin-4-one (274.5 mg, 0.804 mmol) to ethanol (0.5 mL) and add toluenesulfonic acid monohydrate (160 mg). Sonicate to give a dark amber red solution. Add heptane (5 mL), cap the mixture, stir, and heat the mixture to 80° C. The mixture solidifies to a tan-brown solid. Stir mixture for 30 minutes, collect the solid by vacuum filtration and air dry to give the title compound (387 mg, 94%).

EXAMPLE 6

X-Ray Powder Diffraction

The XRPD patterns of crystalline solids are obtained on a Bruker D4 Endeavor X-ray powder diffractometer, equipped with a CuKa source ($\lambda$=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The U. S. Pharmacopeia 35—National Formulary 30 Chapter <941> Characterization of crystalline and partially crystalline solids by X-ray powder diffraction (XRPD) Official Dec. 1, 2012-May 1, 2013. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of °2θ), typically the more prominent peaks. The crystal form diffraction patterns, collected at ambient temperature and relative humidity, were adjusted based on NIST 675 standard peaks at 8.85 and 26.77 degrees 2-theta.

A prepared sample of Example 6 is characterized by an XRPD pattern using CuKa radiation as having diffraction peaks (2-theta values) as described in Table 1 below. Specifically the pattern contains a peak at 7.68 in combination with one or more of the peaks selected from the group consisting of 12.02, 12.93, 15.17, 19.24 and 23.21 with a tolerance for the diffraction angles of 0.2 degrees.

TABLE 2

X-ray powder diffraction peaks of Example 6

| Peak | Angle (2-Theta °) | Relative Intensity (%) |
|---|---|---|
| 1 | 7.28 | 20 |
| 2 | 7.68 | 100 |
| 3 | 9.88 | 15 |
| 4 | 12.02 | 46 |
| 5 | 12.42 | 16 |
| 6 | 12.93 | 69 |
| 7 | 13.11 | 36 |
| 8 | 13.76 | 33 |
| 9 | 15.17 | 45 |
| 10 | 17.02 | 32 |
| 11 | 17.24 | 17 |
| 12 | 19.24 | 83 |
| 13 | 19.88 | 19 |
| 14 | 20.27 | 27 |

TABLE 2-continued

X-ray powder diffraction peaks of Example 6

| Peak | Angle (2-Theta °) | Relative Intensity (%) |
|---|---|---|
| 15 | 21.85 | 36 |
| 16 | 22.06 | 47 |
| 17 | 22.52 | 23 |
| 18 | 23.21 | 75 |
| 19 | 23.42 | 27 |
| 20 | 24.36 | 38 |
| 21 | 24.80 | 33 |
| 22 | 25.76 | 21 |
| 23 | 25.87 | 23 |
| 24 | 28.58 | 28 |

EXAMPLE 7

8-Methyl-2-[4-(1-pyrimidin-2-ylethyl)piperazin-1-yl]-3,5,6,7-tetrahydropyrido[2,3-d]pyrimidin-4-one

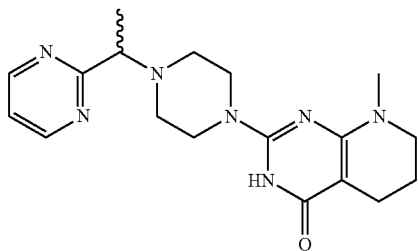 [SMILES: CC(c1ncccn1)N1CCN(c2nc3c(c(=O)[nH]2)CCCN3C)CC1]

EXAMPLE 8

8-Methyl-2-[4-(1-pyrimidin-2-ylethyl)piperazin-1-yl]-3,5,6,7-tetrahydropyrido[2,3-d]pyrimidin-4-one, Isomer 1

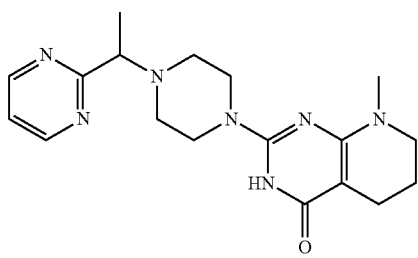 [SMILES: CC(c1ncccn1)N1CCN(c2nc3c(c(=O)[nH]2)CCCN3C)CC1]

EXAMPLE 9

8-Methyl-2-[4-(1-pyrimidin-2-ylethyl)piperazin-1-yl]-3,5,6,7-tetrahydropyrido[2,3-d]pyrimidin-4-one, Isomer 2

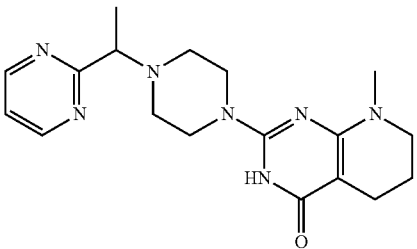 [SMILES: CC(c1ncccn1)N1CCN(c2nc3c(c(=O)[nH]2)CCCN3C)CC1]

Combine 8-methyl-2-piperazin-1-yl-3,5, 6,7-tetrahydropyrido[2,3-d]pyrimidin-4-one bis-(2,2,2-trifluoroacetic acid) salt (1.0 g, 2.1 mmol), 2-acetylpyrimidine (0.38 g, 3.14 mmol), DMF (3 mL), MeOH (1 mL), sodium cyanoborohydride (0.20 g, 3.14 mmol) and stir at room temperature for 20 hours. Add additional 2-acetylpyrimidine (0.38 g, 3.14 mmol) and sodium cyanoborohydride (0.20 g, 3.14 mmol) and heat at 80° C. overnight. Evaporate the DMF under a stream of nitrogen for 4 days and purify by silica gel flash chromatography eluting with DCM to 90% DCM/MeOH to give the title compound, Example 7 (330 mg, 44%) as the racemate.

Separate 8-Methyl-2-[4-(1-pyrimidin-2-ylethyl)piperazin-1-yl]-3,5,6,7-tetrahydropyrido[2,3-d]pyrimidin-4-one using SFC on a Phenomene® Lux® Cellulose-2 column (2.1×25 cm, 5 μm). Mobile Phase: 40% EtOH (0.2% IPAm)/carbon dioxide. Flow rate: 70 mL/min. Detection: 225 nm Obtain the first eluting peak as Isomer 1 and the second eluting peak as Isomer 2.

Example 8, Isomer 1: 135 mg, 99.25% pure with 0.75% of Isomer 2 as an impurity ($T_R$=4.59 min; Phenomenex® Lux® Cellulose-2 column (2.1×25 cm, 5 μm), mobile phase: 40% EtOH (0.2% IPAm)/carbon dioxide, flow rate: 5 mL/min detection: 225 nm). LC-ES/MS m/z 356.3 (M+H)+.

Example 9, Isomer 2: 121 mg, 96.63% pure with 3.36% of Isomer 1 as an impurity ($T_R$=5.91 min, Phenomenex® Lux® Cellulose-2 column (2.1×25 cm, 5 μm), mobile phase: 40% EtOH (0.2% IPAm)/carbon dioxide, flow rate: 5 mL/min, detection: 225 nm). LC-ES/MS m/z 356.3 (M+H)+.

EXAMPLE 10

8-Methyl-2-[4-(1-pyrimidin-2-ylpropyl)piperazin-1-yl]-3,5,6,7-tetrahydropyrido[2,3-d]pyrimidin-4-one

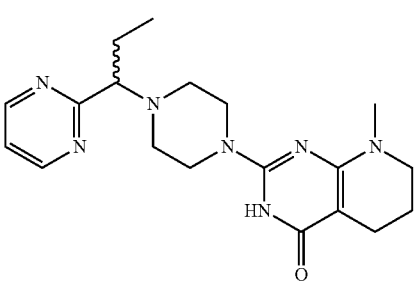 [SMILES: CCC(c1ncccn1)N1CCN(c2nc3c(c(=O)[nH]2)CCCN3C)CC1]

EXAMPLE 11

8-Methyl-2-[4-(1-pyrimidin-2-ylpropyl)piperazin-1-yl]-3,5,6,7-tetrahydropyrido[2,3-d]pyrimidin-4-one, Isomer 1

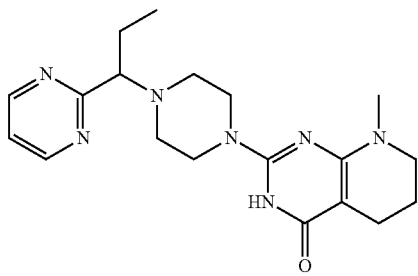 [SMILES: CCC(c1ncccn1)N1CCN(c2nc3c(c(=O)[nH]2)CCCN3C)CC1]

EXAMPLE 12

8-Methyl-2-[4-(1-pyrimidin-2-ylpropyl)piperazin-1-yl]-3,5,6,7-tetrahydropyrido[2,3-d]pyrimidin-4-one, Isomer 2

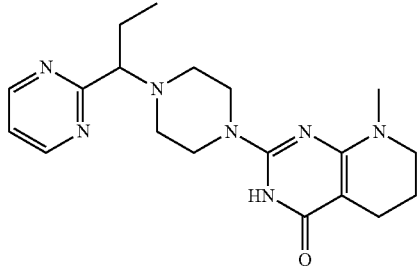 [SMILES: CCC(c1ncccn1)N1CCN(c2nc3c(c(=O)[nH]2)CCCN3C)CC1]

Prepare Examples 10, 11, and 12 essentially following the procedure as described in Examples 7, 8, and 9 using 1-(2-pyrimidinyl)-1-propanone and purifying by silica gel flash chromatography eluting with a gradient of DCM to 90% DCM/MeOH. Purify a second time by silica gel chromatography using the same conditions. Then purify further by high pH prep HPLC (Column: 150 g High resolution C18 Gold; Initial: 5% acetonitrile/95% 10 mM ammonium bicarbonate w/5% MeOH with gradient to 60% acetonitrile/40% ammonium bicarbonate w/5% MeOH over 30 mM, detection wavelengths 239, 254, 280 and 290 nm) to give the title compound, Example 10 (140 mg, 18%). Separate the resulting enantiomeric mixture using SFC using the conditions described for Examples 8 and 9 with the exception that a Lux® Cellulose-4 column is used.

Example 11, Isomer 1: 50 mg, >99.9% purity ($T_R$=4.26 mM; Phenomenex® Lux® Cellulose-4 column (2.1×25 cm, 5 μm), mobile phase: 40% EtOH (0.2% IPAm)/carbon dioxide, flow rate: 5 mL/min, detection: 225 nm). LC-ES/MS m/z 370.2 (M+H)$^+$.

Example 12, Isomer 2: 47 mg, >99.9% purity ($T_R$=5.67 min; Phenomenex® Lux® Cellulose-4 column (2.1×25 cm, 5 μm). Mobile Phase: 40% EtOH (0.2% IPAm)/carbon dioxide. Flow rate: 5 mL/min Detection: 225 nm), LC-ES/MS m/z 370.2 (M+H)$^+$.

EXAMPLE 13

2-[4-[(4-methoxypyrimidin-2-yl)methyl]piperazin-1-yl]-8-methyl-3,5,6,7-tetrahydropyrido[2,3-d]pyrimidin-4-one

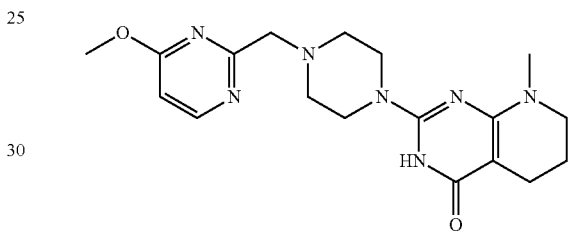

Combine 8-methyl-2-piperazin-1-yl-3,5, 6,7-tetrahydropyrido[2,3-d]pyrimidin-4-one bis-(2,2,2-trifluoroacetic acid) salt (0.5 g, 1.0 mmol), 4-methoxypyrimidine-2-carbaldehyde (150 mg, 1.08 mmol), DMF (10 mL), MeOH (1 mL) and sodium cyanoborohydride (136 mg, 2.17 mmol) and stir at room temperature for 3 days. Dilute with MeOH and absorb onto an SCX-2 column, rinse with MeOH and then elute with 2 M NH$_3$ in MeOH, concentrate and purify by silica gel flash chromatography eluting with a gradient of DCM to 90% DCM/MeOH to give the title compound (43 mg, 11%). LC-ES/MS m/z 372.1 (M+H)$^+$ $T_R$=1.519 min.

The following Examples are prepared essentially following the procedure of Example 13, using the appropriate aldehyde and the appropriate chromatography.

TABLE 3

| Ex. No. | Chemical Name | Structure | LC-ES/MS m/z |
|---|---|---|---|
| 14[1] | 8-Methyl-2-[4-[(4-methylpyrimidin-2-yl)methyl]piperazin-1-yl]-3,5,6,7-tetrahydropyrido[2,3-d]pyrimidin-4-one | 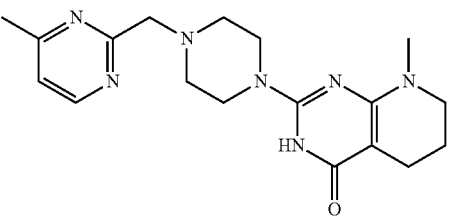 [SMILES: Cc1ccnc(CN2CCN(c3nc4c(c(=O)[nH]3)CCCN4C)CC2)n1] | 356.1 (M + H)$^+$ |

TABLE 3-continued

| Ex. No. | Chemical Name | Structure | LC-ES/MS m/z |
|---|---|---|---|
| 15[2] | 8-Methyl-2-[4-[[5-(trifluoromethyl)pyrimidin-2-yl]methyl)piperazin-1-yl]-3,5,6,7-tetrahydropyrido[2,3-d]pyrimidin-4-one | 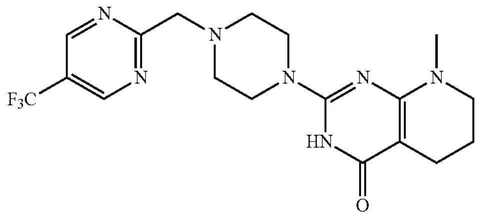 [SMILES: CN1CCCc2c1nc(N1CCN(Cc3ncc(C(F)(F)F)cn3)CC1)[nH]c2=O] | 410.1 (M + H)+ |
| 16 | 8-Methyl-2-[4-[[4-(trifluoromethyl)pyrimidin-2-yl]methyl]piperazin-1-yl]-3,5,6,7-tetrahydropyrido[2,3-d]pyrimidin-4-one | 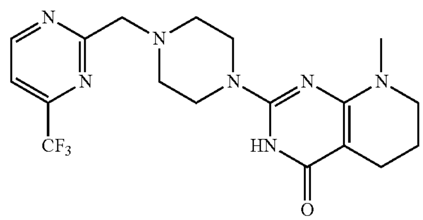 [SMILES: CN1CCCc2c1nc(N1CCN(Cc3nccc(C(F)(F)F)n3)CC1)[nH]c2=O] | 410.2 (M + H)+ |
| 17[3] | 8-Methyl-2-[4-[(5-methylpyrimidin-2-yl)methyl]piperazin-1-yl]-3,5,6,7-tetrahydropyrido[2,3-d]pyrimidin-4-one | 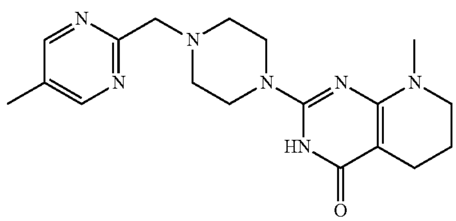 [SMILES: Cc1cnc(CN2CCN(c3nc4c(c(=O)[nH]3)CCCN4C)CC2)nc1] | 356.3 (M + H)+ |
| 18[4] | 2-[4-[(5-Chloropyrimidin-2-yl)methyl]piperazin-1-yl]-8-methyl-3,5,6,7-tetrahydropyrido[2,3-d]pyrimidin-4-one | 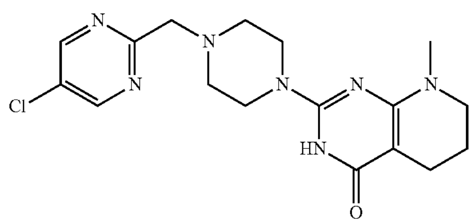 [SMILES: CN1CCCc2c1nc(N1CCN(Cc3ncc(Cl)cn3)CC1)[nH]c2=O] | 376.0 ($^{35}$Cl) (M + H)+ |
| 19[5] | 8-Methyl-2-[4-(2-pyridylmethyl)piperazin-1-yl]-3,5,6,7-tetrahydropyrido[2,3-d]pyrimidin-4-one | 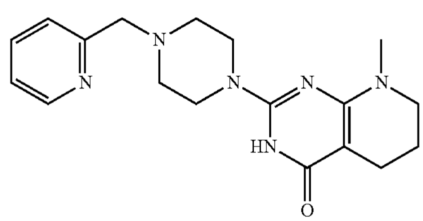 [SMILES: CN1CCCc2c1nc(N1CCN(Cc3ccccn3)CC1)[nH]c2=O] | 341.2 (M + H)+ |

[1] Stir reaction for 3 days.

[2] Add additional aldehyde (1 eq) and sodium cyanoborohydride (1.5 eq); then heat at 80° C. for 6 h. Further purify by general method of reverse phase chromatography (High pH 5-100).

[3] Further purify by general method of reverse phase chromatography (High pH 9-24).

[4] Further purify by general method of reverse phase chromatography (Low pH 0.1% TFA/ACN) followed by chromatography on an SCX-2 column.

[5] Stir reaction at rt for 12 hours and further purify by general method of reverse phase chromatography (High pH 13-48).

EXAMPLE 20

2-[4-[(3-Fluoro-2-pyridyl)methyl]piperazin-1-yl]-8-methyl-3,5,6,7-tetrahydropyrido[2,3-d]pyrimidin-4-one

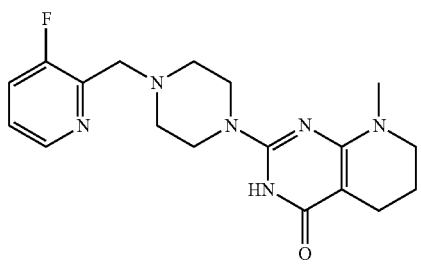 [SMILES: CN1CCCc2c1nc(N1CCN(Cc3ncccc3F)CC1)[nH]c2=O]

Suspend 8-methyl-2-piperazin-1-yl-3,5,6,7-tetrahydropyrido[2,3-d]pyrimidin-4-one bis-(2,2,2-trifluoroacetic acid) (20.31 g, 34.34 mmol) in DCM (114 mL) and purge with nitrogen. Add 3-fluoropyridine-2-carbaldehyde (5.26 g, 41.2 mmol) and stir for 60 minutes. Then add sodium triacetoxyborohydride (14.56 g, 68.68 mmol) in one portion and observe an exotherm to reflux. Stir and allow the reaction to cool to room temperature over 1 hour. Pour into 0.5 M NaOH (200 mL) and adjust the pH: 7-8 with 2 M NaOH. Collect the organic layer and extract the aqueous layer with DCM (2×200 mL). Combine and dry the organic layers over sodium sulfate, filter, and concentrate to give an oil. Purify by silica gel chromatography (400 g), eluting with 95% DCM/5% MeOH for 8 column volumes and with 90% DCM/10% MeOH for 8 column volumes to give the title compound (7.59 g, 61.7%) with >97% HPLC purity and also 2.64 g (21.5%) of additional product with 87% HPLC purity. LC ES/MS m/z 359.1 (M+1)+.

EXAMPLE 21

2-[4-[(2-Methoxyphenyl)methyl]piperazin-1-yl]-8-methyl-3,5,6,7-tetrahydropyrido[2,3-d]pyrimidin-4-one

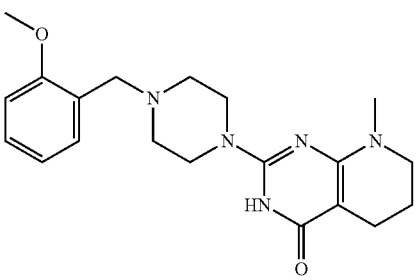 [SMILES: COc1ccccc1CN1CCN(c2nc3c(c(=O)[nH]2)CCCN3C)CC1]

Combine 8-methyl-2-piperazin-1-yl-3,5,6,7-tetrahydropyrido[2,3-d]pyrimidin-4-one bis-(2,2,2-trifluoroacetic acid) salt (0.25 g, 0.52 mmol), 2-methoxybenzaldehyde (0.21 g, 1.57 mmol), DMF (15 mL), MeOH (5 mL) and sodium cyanoborohydride (100 mg, 1.57 mmol) and stir at room temperature for 12 hours. Dilute with methanol and absorb onto an SCX-2 column, rinse with MeOH and then elute with 2 M $NH_3$ in MeOH, concentrate and purify by reverse phase chromatography, see general method for reverse chromatography (High pH 21-55) to give the title compound (223 mg, 59%). LC-ES/MS m/z 370.2 (M+H)+.

The following compounds are prepared essentially as described in Example 21 using the appropriate aldehyde.

TABLE 4

| Ex. No. | Chemical name | Structure | LC-ES/MS m/z |
|---|---|---|---|
| 22 | 2-[4-[(2-Fluorophenyl)methyl]piperazin-1-yl]-8-methyl-3,5,6,7-tetrahydropyrido[2,3-d]pyrimidin-4-one | 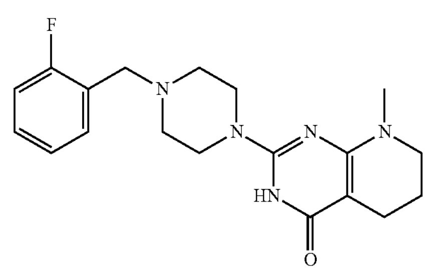 [SMILES: CN1CCCc2c1nc(N1CCN(Cc3ccccc3F)CC1)[nH]c2=O] | 358.2 (M + H)+ |
| 23[a] | 8-Methyl-2-[4-(o-tolylmethyl)piperazin-1-yl]-3,5,6,7-tetrahydropyrido[2,3-d]pyrimidin-4-one | 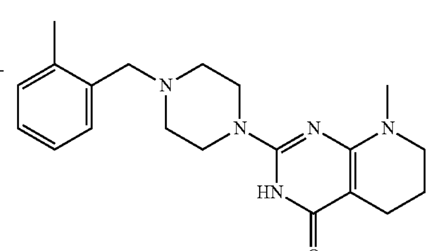 | 354.2 (M + H)+ |

TABLE 4-continued

| Ex. No. | Chemical name | Structure | LC-ES/MS m/z |
|---|---|---|---|
| 24[b] | 8-Methyl-2-[4-[(3-methyl-2-pyridyl)methyl]piperazin-1-yl]-3,5,6,7-tetrahydropyrido[2,3-d]pyrimidin-4-one | 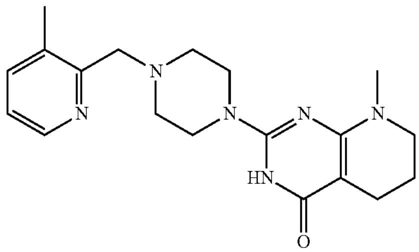 [SMILES: Cc1cccnc1CN1CCN(c2nc3c(c(=O)[nH]2)CCCN3C)CC1] | 355.2 (M + H)+ |
| 25[c] | 2-[4-[(3-Methoxy-2-pyridyl)methyl]piperazin-1-yl]-8-methyl-3,5,6,7-tetrahydropyrido[2,3-d]pyrimidin-4-one | 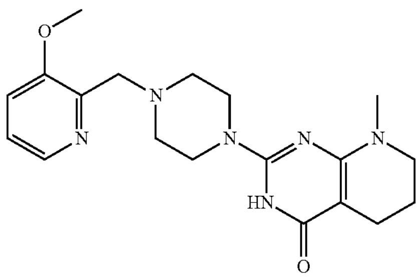 [SMILES: COc1cccnc1CN1CCN(c2nc3c(c(=O)[nH]2)CCCN3C)CC1] | 371.2 (M + H)+ |
| 26[b] | 8-Methyl-2-[4-[[3-(trifluoromethyl)-2-pyridyl]methyl]piperazin-1-yl]-3,5,6,7-tetrahydropyrido[2,3-d]pyrimidin-4-one | 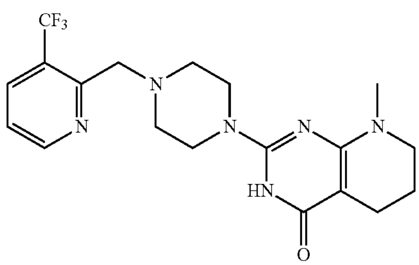 [SMILES: CN1CCCc2c1nc(N1CCN(Cc3ncccc3C(F)(F)F)CC1)[nH]c2=O] | 409.2 (M + H)+ |
| 27[d] | 8-Methyl-2-[4-[[2-(trifluoromethyl)phenyl]methyl]piperazin-1-yl]-3,5,6,7-tetrahydro-pyrido[2,3-d]pyrimidin-4-one | 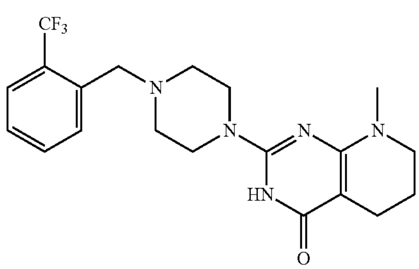 [SMILES: CN1CCCc2c1nc(N1CCN(Cc3ccccc3C(F)(F)F)CC1)[nH]c2=O] | 408.2 (M + H)+ |

[a]Reverse phase chromatography (High pH 30-64).
[b]Reverse phase chromatography (High pH 23-57).
[c]Reverse phase chromatography (High pH 13-48).
[d]Reverse phase chromatography (High pH 39-73).

EXAMPLE 28

2-[4-[(3-Fluoro-2-pyridyl)methyl]piperazin-1-yl]-8-methyl-3,5,6,7-tetrahydropyrido[2,3-d]pyrimidin-4-one, dihydrochloride

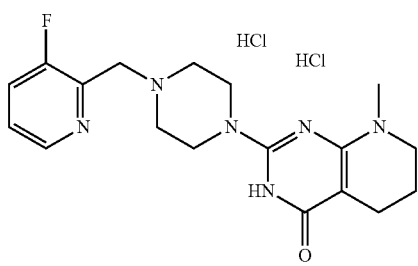 [SMILES: CN1CCCc2c1nc(N1CCN(Cc3ncccc3F)CC1)[nH]c2=O ; Cl ; Cl]

In 2 vials add to each DCM (5 mL) 4M HCl in dioxane (1 mL, 4 mmol), and 2-[4-[(3-fluoro-2-pyridyl)methyl]piperazin-1-yl]-8-methyl-3,5,6,7-tetrahydropyrido[2,3-d]pyrimidin-4-one (0.117 g, 0.65 mmol). Shake the vials for 1 hour, combine into 1 vial and then evaporate under a stream of nitrogen overnight. Dry the material in a vacuum oven overnight to give the title compound (0.28 g, 99%). LC-ES/MS m/z 359.2 [M+H]$^+$, $T_R$=1.04 min.

The following Examples are prepared essentially as described in Example 28 using the appropriate compound of Examples 21-27.

TABLE 5

| Ex. No. | Chemical name | Structure | LC-ES/MS m/z |
|---|---|---|---|
| 29 | 2-[4-[(2-Methoxyphenyl)methyl]piperazin-1-yl]-8-methyl-3,5,6,7-tetrahydropyrido[2,3-d]pyrimidin-4-one dihydrochloride | 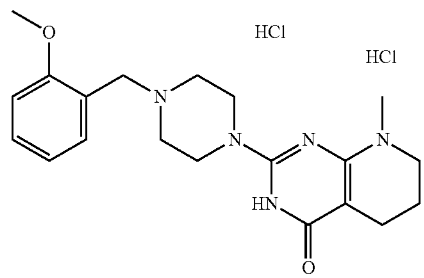 [SMILES: COc1ccccc1CN1CCN(c2nc3c(c(=O)[nH]2)CCCN3C)CC1 ; Cl ; Cl] | 370.2 (M + H)$^+$ |
| 30 | 2-[4-[(2-Fluorophenyl)methyl]piperazin-1-yl]-8-methyl-3,5,6,7-tetrahydropyrido[2,3-d]pyrimidin-4-one dihydrochloride | 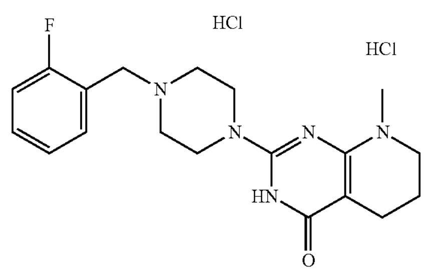 [SMILES: Cl ; CN1CCCc2c1nc(N1CCN(Cc3ccccc3F)CC1)[nH]c2=O ; Cl] | 358.2 (M + H)$^+$ |
| 31 | 8-Methyl-2-[4-(o-tolylmethyl)piperazin-1-yl]-3,5,6,7-tetrahydropyrido[2,3-d]pyrimidin-4-one dihydrochloride | 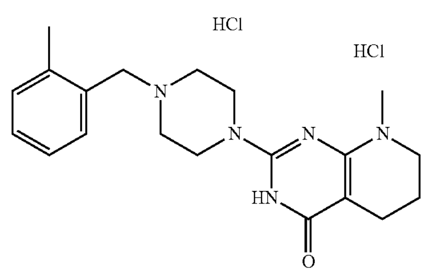 [SMILES: Cl ; Cc1ccccc1CN1CCN(c2nc3c(c(=O)[nH]2)CCCN3C)CC1 ; Cl] | 354.2 (M + H)$^+$ |
| 32 | 8-Methyl-2-[4-[(3-methyl-2-pyridyl)methyl]piperazin-1-yl]-3,5,6,7-tetrahydropyrido[2,3-d]pyrimidin-4-one dihydrochloride | 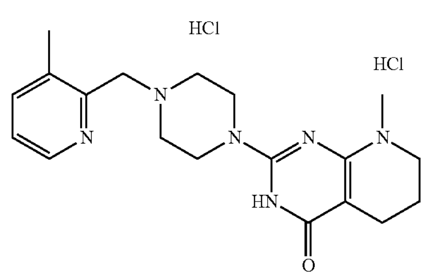 [SMILES: Cl ; Cc1cccnc1CN1CCN(c2nc3c(c(=O)[nH]2)CCCN3C)CC1 ; Cl] | 355.2 (M + H)$^+$ |

TABLE 5-continued

| Ex. No. | Chemical name | Structure | LC-ES/MS m/z |
|---|---|---|---|
| 33 | 2-[4-[(3-Methoxy-2-pyridyl)methyl]piperazin-1-yl]-8-methyl-3,5,6,7-tetrahydropyrido[2,3-d]pyrimidin-4-one dihydrochloride | 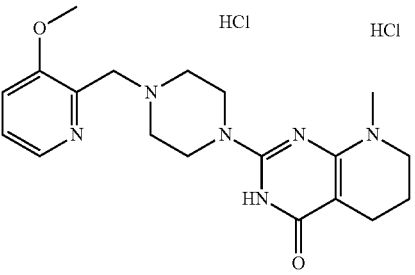 [SMILES: COc1cccnc1CN1CCN(c2nc3c(c(=O)[nH]2)CCCN3C)CC1 ; Cl ; Cl] | 371.2 (M + H)⁺ |
| 34 | 8-Methyl-2-[4-(2-pyridylmethyl)piperazin-1-yl]-3,5,6,7-tetrahydropyrido[2,3-d]pyrimidin-4-one dihydrochloride | 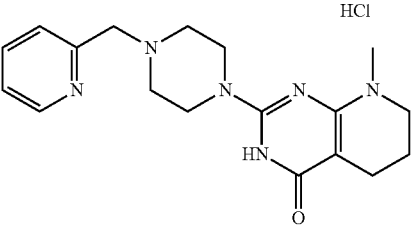 | 341.2 (M + H)⁺ |
| 35 | 8-Methyl-2-[4-[[3-(trifluoromethyl)-2-pyridyl]methyl]piperazin-1-yl]-3,5,6,7-tetrahydropyrido[2,3-d]pyrimidin-4-one dihydrochloride | 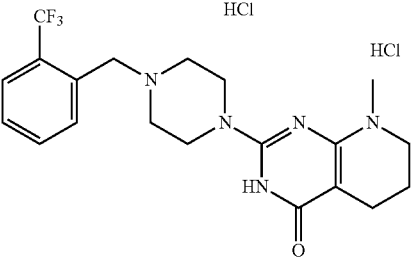 [SMILES: Cl ; CN1CCCc2c1nc(N1CCN(Cc3ccccc3C(F)(F)F)CC1)[nH]c2=O ; Cl] | 409.2 (M + H)⁺ |
| 36 | 8-Methyl-2-[4-[[2-(trifluoromethyl)phenyl]methyl]piperazin-1-yl]-3,5,6,7-tetrahydropyrido[2,3-d]pyrimidin-4-one dihydrochloride | 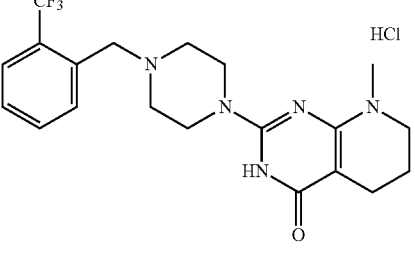 | 408.2 (M + H)⁺ |

EXAMPLE 37

2-[[4-(8-Methyl-4-oxo-3,5,6,7-tetrahydropyrido[2,3-d]pyrimidin-2-yl)piperazin-1-yl]methyl]benzonitrile; bis-2,2,2-trifluoroacetic acid

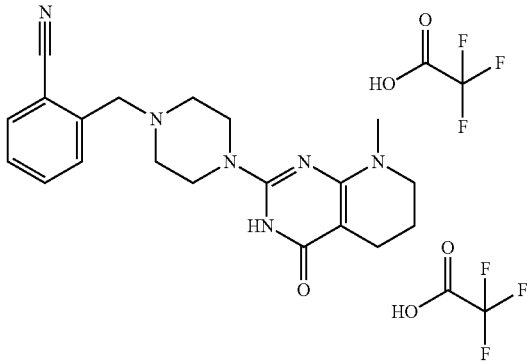

Combine a solution of 8-methyl-2-piperazin-1-yl-3,5,6,7-tetrahydropyrido[2,3-d]pyrimidin-4-one bis-(2,2,2-trifluoroacetic acid) (0.364 g, 0.76 mmol) in DMF (3.2 mL) with 2-cyanobenzaldehyde (0.499 g, 3.18 mmol) and stir at room temperature for 1 hour. Add sodium cyanoborohydride (0.143 g, 2.28 mmol) and stir at room temperature overnight. Pour into water and attempt collection by filtration. Observe clogging of filter and then add 2 N NaOH and NaCl (aqueous) and extract the crude product into ethyl acetate (3×). Combine the organic layers, dry over sodium sulfate, filter, and concentrate. Purify by silica gel chromatography eluting with 98% DCM/2% ethanol isocratic for 10 min with step gradient to 95% DCM/5% ethanol and hold for 45 min. Purify further by preparative reverse phase chromatography eluting with 5% acetonitrile (0.1% TFA)/95% water (0.1% TFA) gradient to 54% acetonitrile (0.1% TFA)/46% water (0.1% TFA) to give the title compound (48.1 mg, 10.7%). LC-ES/MS m/z 365.2 [M+H]$^+$

EXAMPLE 38

2-[4-[(2-Chlorophenyl)methyl]piperazin-1-yl]-8-methyl-3,5,6,7-tetrahydropyrido[2,3-d]pyrimidin-4-one

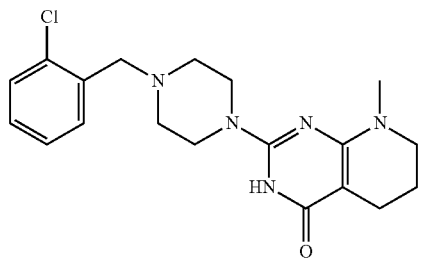

Prepare the title compound essentially as described in Example 37 using 2-chloro-5-methyl-pyrimidine 2-chlorobenzaldehyde. Purify the crude material by silica gel flash chromatography (5% EtOH/CHCl$_3$ to 10% EtOH/CHCl$_3$ gradient). Recrystallize the material from DMSO/MeOH to obtain a white solid (83 mg, 29%). LC-ES/MS m/z 374.3 ($^{35}$Cl) [M+H]$^+$.

EXAMPLE 39

2-[4-[(5-Fluoropyrimidin-2-yl)methyl]piperazin-1-yl]-8-methyl-3,5,6,7-tetrahydropyrido [2,3-d]pyrimidin-4-one

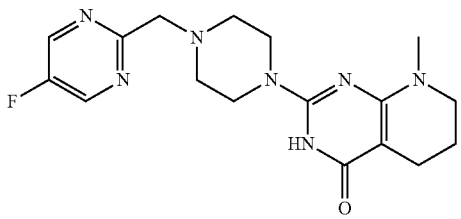 [SMILES: CN1CCCc2c1nc(N1CCN(Cc3ncc(F)cn3)CC1)[nH]c2=O]

Combine potassium trifluoro-[[4-(8-methyl-4-oxo-3,5,6,7-tetrahydropyrido[2,3-d]pyrimidin-2-yl)piperazin-1-yl]methyl]boranuide (273 mg, 0.74 mmol), 2-chloro-5-fluoropyrimidine (98 mg, 0.74 mmol), cesium carbonate (723 mg, 2.22 mmol), X-Phos (71 mg, 0.15 mmol), THF (10 mL) and water (1 mL) and degas with a stream of nitrogen for 2 min. Add palladium (II) acetate (17 mg, 0.074 mmol) and heat at 80° C. overnight. Partition the mixture between ethyl acetate and water and separate the organic layer. Dry over magnesium sulfate, filter, and concentrate the filtrate under reduced pressure. Purify the resulting residue by silica gel flash chromatography eluting with DCM to 90% DCM/MeOH to give the title compound (20 mg, 7.5%). LC-ES/MS m/z 360.2 [M+H]$^+$.

EXAMPLE 40

2-[[4-(8-Methyl-4-oxo-3,5,6,7-tetrahydropyrido[2,3-d]pyrimidin-2-yl)piperazin-1-yl]methyl]pyridine-3-carbonitrile

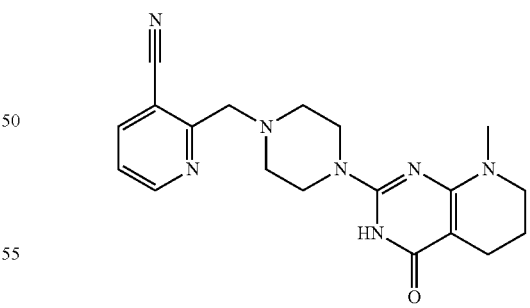

Dissolve 2-[4-[(3-bromo-2-pyridyl)methyl]piperazin-1-yl]-8-methyl-3,5,6,7-tetrahydropyrido[2,3-d]pyrimidin-4-one (167 mg, 0.398 mmol) in DMF (10 mL) and degas with a stream of nitrogen for 1 min. Add tetrakis(triphenylphosphine)palladium (92 mg, 0.080 mmol) and zinc cyanide (187 mg, 1.59 mmol) and heat the mixture at 120° C. overnight. Cool the reaction and dilute with MeOH. Transfer the mixture to a 10 g SCX-2 column and elute with 2 M NH$_3$ in MeOH. Concentrate and further purify the resulting residue reverse phase chromatography (High pH 9-29) to give the title compound (35 mg, 24%). LC-ES/MS m/z 366.2 (M+H)+

EXAMPLE 41

2-[4-[(4-Chloropyrimidin-2-yl)methyl]piperazin-1-yl]-8-methyl-3,5,6,7-tetrahydropyrido[2,3-d]pyrimidin-4-one

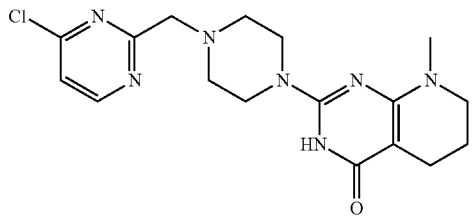 [SMILES: CN1CCCc2c1nc(N1CCN(Cc3nccc(Cl)n3)CC1)[nH]c2=O]

Combine 2-(bromomethyl)-4-chloro-pyrimidine (322 mg, 1.55 mmol) as a crude solution in carbon tetrachloride (5 mL), DCM (2 mL), triethylamine (0.65 mL, 4.65 mmol), and 8-methyl-2-piperazin-1-yl-3,5,6,7-tetrahydropyrido[2,3-d]pyrimidin-4-one bis-(2,2,2-trifluoroacetic acid) (739 mg, 1.55 mmol) and stir at 25° C. for 3 days. Partition the reaction mixture between DCM and water and extract the aqueous layer with DCM. Combine the organic layers, dry over MgSO4, filter, and concentrate. Purify the resulting residue by mass guided SFC (column: 4-nitrobenzene sulfonamide, Princeton Chromatography, 150×30 mm, flow rate=100 mL/min; method: 95% CO2/14 mM ammonia in MeOH isocratic for 30 sec. then gradient to 60% CO2/14 mM ammonia in MeOH gradient over 330 sec., then ramp to 50% CO2/14 mM ammonia in MeOH over 10 sec. and hold for 30 sec.) to give 71 mg of desired product with ammonia salt impurities. The product is further purified by silica gel flash chromatography (CH2Cl2/MeOH, 90:10) to give the title compound (28 mg, 5%). LC-ES/MS m/z 376.0 [M+H]+

EXAMPLE 42

8-Methyl-2-[4-(pyrazin-2-ylmethyl)piperazin-1-yl]-3,5,6,7-tetrahydropyrido[2,3-d]pyrimidin-4-one

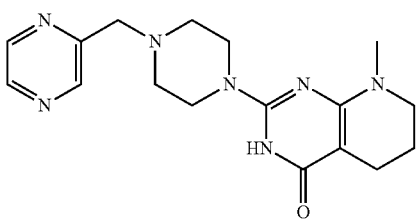 [SMILES: CN1CCCc2c1nc(N1CCN(Cc3cnccn3)CC1)[nH]c2=O]

Combine 8-methyl-2-piperazin-1-yl-3,5, 6,7-tetrahydropyrido[2,3-d]pyrimidin-4-one bis-(2,2,2-trifluoroacetic acid) (500 mg, 1.05 mmol), triethylamine (0.73 mL, 5.2 mmol), sodium iodide (78.5 mg, 0.52 mmol) and acetonitrile (7 mL). Add 2-(chloromethyl)pyrazine (201 mg, 1.57 mmol) and stir at 25° C. for 72 h. Dilute the reaction with DCM and water and extract the product into DCM. Wash the organic portion with saturated NaHCO3 and brine, dry over Na2SO4, filter, and concentrate. Purify the resulting residue by silica gel flash chromatography (DCM/2M NH3 in MeOH, 90:10) to give the title compound as a yellow solid (249 mg, 0.72 mmol, 70%). LC-ES/MS m/z 342.0 [M+H]+, $T_R$=0.99 min.

The following Examples are prepared essentially following the procedure described in Example 42, using the appropriate halo-methylpyrazine.

TABLE 6

| Ex. No. | Chemical name | Structure | LC-ES/MS m/z |
|---|---|---|---|
| 43 | 2-[4-[(3-Chloropyrazin-2-yl)methyl]piperazin-1-yl]-8-methyl-3,5,6,7-tetrahydropyrido[2,3-d]pyrimidin-4-one | 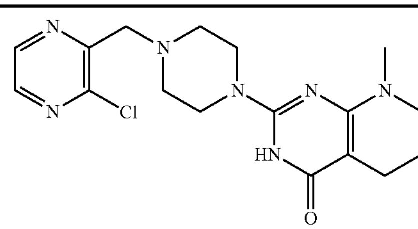 | 376.0 [M + H]+, $T_R$ = 1.17 min. |
| 44 | 8-Methyl-2-[4-[(3-methyl-pyrazin-2-yl)methyl]piperazin-1-yl]-3,5,6,7-tetrahydropyrido[2,3-d]pyrimidin-4-one | 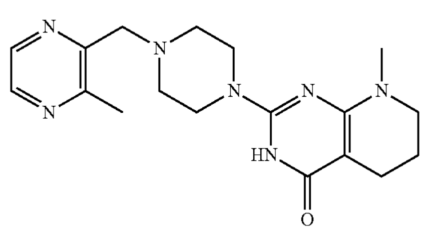 [SMILES: Cc1nccnc1CN1CCN(c2nc3c(c(=O)[nH]2)CCCN3C)CC1] | 356.0 [M + H]+, $T_R$ = 1.03 min. |

EXAMPLE 45

2-[4-[(3,5-Difluoro-2-pyridyl)methyl]piperazin-1-yl]-8-methyl-3,5,6,7-tetrahydropyrido[2,3-d]pyrimidin-4-one

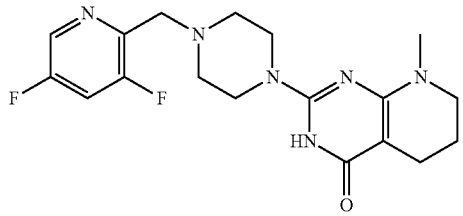 [SMILES: CN1CCCc2c1nc(N1CCN(Cc3ncc(F)cc3F)CC1)[nH]c2=O]

Add 2-(chloromethyl)-3,5-difluoropyridine (182 mg, 1.11 mmol), 8-methyl-2-piperazin-1-yl-3,5,6,7-tetrahydropyrido[2,3-d]pyrimidin-4-one (260 mg, 1.04 mmol), potassium carbonate (2.2 g, 15 mmol) and acetonitrile (5 mL) and stir the mixture at room temperature overnight. Concentrate the reaction mixture under reduced pressure and purify the residue by silica gel chromatography (elution with MeOH/DCM, 1/20) to give the title compound (160 mg, 43%). LC-ES/MS m/z 377.2 (M+H)$^+$, $T_R$=1.11 min Cancer is increasingly recognized as a heterogeneous collection of diseases whose initiation and progression are induced by the aberrant activation or function of one or more genes that regulate DNA repair, genome stability, cell proliferation, cell death, adhesion, angiogenesis, invasion, and metastasis in cell and tissue microenvironments. Variant or aberrant function of the "cancer" genes may result from naturally occurring DNA polymorphism, changes in genome copy number (through amplification, deletion, chromosome loss, or duplication), changes in gene and chromosome structure (through chromosomal translocation, inversion, or other rearrangement that leads to deregulated gene expression), and point mutations. Cancerous neoplasms may be induced by one aberrant gene function, and maintained by the same aberrant gene function, or maintenance and progression exacerbated by additional aberrant gene activations or functions.

Beyond the genetic chromosomal aberrations mentioned above, each of the cancers may also include epigenetic modifications of the genome including DNA methylation, genomic imprinting, and histone modification by acetylation, methylation, or phosphorylation. An epigenetic modification may play a role in the induction and/or maintenance of the malignancy.

Diagnosis of cancerous malignancies by biopsy, immunophenotyping and other tests are known and routinely used. In addition to high resolution chromosome banding and advanced chromosomal imaging technologies, chromosome aberrations in suspected cases of cancer can be determined through cytogenetic analysis such as fluorescence in situ hybridization (FISH), karyotyping, spectral karyotyping (SKY), multiplex FISH (M-FISH), comparative genomic hybridization (CGH), single nucleotide polymorphism arrays (SNP Chips) and other diagnostic and analysis tests known and used by those skilled in the art.

An important part of the Wnt/β-catenin signaling pathway is the regulated proteolysis of the downstream effector β-catenin by the β-catenin destruction complex. The principal constituents of the β-catenin destruction complex are adenomatous polyposis *coli* (APC), Axin, and GSK3α/β. In the absence of Wnt pathway activation, cytosolic β-catenin is constitutively phosphorylated and targeted for degradation. Upon Wnt stimulation, the β-catenin destruction complex disassociates, which leads to the accumulation of cytosolic β-catenin, translocation to the nucleus, and transcription of Wnt canonical pathway responsive genes.

Considerable efforts have been made to identify pharmaceutical agents that inhibit the canonical Wnt/β-catenin signaling pathway. TNKS1 and TNKS2 inhibitors such as XAV939, Huang et al., *Nature*, 2009, 461, 614; JW55, Waaler et al., *Cancer Res.*, 2012, 72(11), 2822; G007-LK, Lau et al., *Cancer Res.*, 2013, 73(10), 3132; TNKS656, Shultz et al., *J. Med. Chem.* published online Jul. 11, 2013, DOI: 10.1021/jm400807n; and WO 2013/117288 are known. Despite these efforts, no clinical TNKS1 and TNKS2 inhibitor therapeutic agents have emerged at this time.

Aberrant activation of the pathway, mediated by over expression of Wnt proteins or mutations affecting components of the β-catenin destruction complex, thus leading to stabilization of β-catenin, has been observed in cancers. Notably, truncating mutations of APC are the most prevalent genetic alterations in colorectal carcinomas (Miyaki, M. et al. *Cancer Res.* 1994, 54, 3011-20; Miyoshi, Y. et al. *Hum. Mol. Genet.* 1992, 1, 229-33; and Powell, S. M. et al. *Nature* 1992, 359, 235-7). In addition, Axin1 and Axin2 mutations, negative regulators of the Wnt signaling pathway, have been identified in patients with hepatocarcinomas and colorectal cancer respectively (Taniguchi, K. et al. *Oncogene* 2002, 21, 4863-71; Liu, W. et al. *Nat. Genet.* 2000, 26, 146-7; Lammi, L. et al. *Am. J. Hum. Genet.* 2004, 74, 1043-50). These somatic mutations result in Wnt-independent stabilization of β-catenin and constitutive activation of β-catenin-mediated transcription.

Aberrant Wnt signaling pathway activity has been implicated in several cancers (Waaler et al. *Cancer Res.* 2012, 72, 2822-2832; Busch et al. *BMC Cancer* 2013, 13, 211; Yang et al. *Oncogene* 2011, 30, 4437-4446; De Robertis et al. *Mol. Cancer Ther.* 2013, 12, 1180-1189; Polakis, P. *Curr. Opin. Genet. Dev.* 2007, 17, 45-51; and Barker, N. et al. *Nat. Rev. Drug Discov.* 2006, 5, 997-1014), including colorectal, gastric, liver, breast, triple negative breast cancer, ovarian, medulloblastoma, melanoma, lung, non-small cell lung, pancreas, prostate cancers and glioblastomas. Aberrant Wnt/β-catenin pathway signaling activity has been implicated in T-cell lymphoma, T-lymphoblastic lymphoma, T-cell acute lymphocytic leukemia (T-ALL) Groen et al. *Cancer Res.* 2008, 68, 6969-6977; multiple myeloma Qiang et al. *Oncogene* 2003, 22, 1536-1545, and Chim et al. *Leukemia* 2007, 21, 2527-2536; mantle cell lymphoma Gelebart et al. *Blood* 2008, 112, 5171-5179; chronic myeloid leukemia (CML), Heidel et al. *Cell Stem Cell* 2012, 10(4):412-424, and acute myeloid leukemia (AML), Ysebaert et al. *Leukemia* 2006, 20, 1211-1216.

It has been found that β-catenin degradation can be promoted by stabilizing the Axin/APC/GSK3α/β destruction complex through the inhibition of the poly-ADP-ribose polymerase (PARP) enzymes tankyrase 1 and tankyrase 2, Huang et al. *Nature* 2009, 461, 614-620.

The following in vitro and in vivo studies demonstrate the Wnt/β-catenin signaling pathway inhibitory activity and efficacy of exemplified and tested compounds of Formula I, or a pharmaceutically acceptable salt thereof, in inhibiting hTNKS1 and hTNKS2, stabilization of Axin2 in HEK293 cells, selectivity against PARP1 inhibition, reduce the expression of Wnt-inducible genes expression, and in vivo antitumor activity. These assays are generally recognized by those skilled in the art as indicative of human clinical chemotherapeutic activity Inhibition of TNKS1 and TNKS2 are believed to be effective against aberrant activation of the Wnt/β-catenin signaling pathway. Assays evidencing Wnt/β-catenin signaling pathway inhibitory activity and efficacy may be carried out substantially as follows or by similar assays affording similar data.

Assays

Generally, cell lines are generated using commercially available materials and by procedures known to and routinely used by those skilled in the art.

Biochemical Assay to Demonstrate Compound Inhibition of hTNKS Enzyme Activity

The enzymatic activity of hTNKS1 and hTNKS2 is assessed using an enzyme-linked immunosorbent assay (ELISA) which detects poly ADP ribose incorporated into plate-bound Telomeric repeat binding factor 1 (TRF1) protein (NCBI, Accession number NP_059523.2 (SEQ ID NO: 1) in a 384-well format. Using recombinant hTNKS1 (NCBI, Accession number NP_003738.2 (SEQ ID NO: 2) or hTNKS2 (NCBI, Accession number NP_079511.1 (SEQ ID NO: 3) enzyme, this assay uses biotinylated NAD+ and measures its incorporation into recombinant hTRF1 using a streptavidin-horseradish peroxidase (HRP) conjugate and TMB peroxidase substrate to generate a colorimetric signal. Recombinant Flag-tagged hTRF1 protein is generated by expressing full length human TRF1 protein with an N-terminal Flag tag in *E. coli*. Recombinant Flag-hTNKS1 (with a change of Q83P) protein is generated by expressing full length human TNKS1 with an N-terminal Flag tag in Baculovirus according to the manufacturer's protocol of Bac-to-Bac Baculovirus Expression system (Invitrogen™; See also Invitrogen™ User Manual, Version F, dated 4 Sep. 2010; and Invitrogen™ Instruction Manual dated 27 Feb. 2002). The Flag tags on hTRF1 and hTNK1 are used only for purification of the enzymes and are not otherwise involved in the ELISA assay.

Flag-TRF1 is diluted to 5 µg/ml using TBS coating buffer (50 mM Tris, pH 8.0, 150 mM NaCl) and 25 µl is added to each well of a Corning 3700 plate (Tewksbury, Mass. #CLS3700). The plates are incubated overnight at 4° C. The next day the plates are washed 3 times with 50 µl/well wash buffer (PBS (prepared from 10× concentrate using Hyclone, Logan, Utah #SH30258.01) with 0.1% Tween-20 (Sigma, St. Louis, Mo. #7949)) followed with blocking for 1.5 hours at room temperature using 50 µl 1% Casein block buffer (Thermo Scientific, Waltham, Mass. #37528) in 1×PBS (Roche, Indianapolis, Ind. #11666789001). After blocking, the plates are washed 3 times with 50 µl/well wash buffer. The enzyme assay is set up using 2 µg/ml of Flag-hTNKS1, 9.5 µM NAD+ (Sigma, St. Louis, Mo. #N0632), 0.5 µM biotin-NAD+ (Trevigen, Gaithersburg, Md. #4670-500-01), and compounds diluted from 10 µM to 4 nM final concentration in 50 mM Tris, pH 8.0 (Invitrogen™, Grand Island, N.Y. #15568-025), 4 mM MgCl$_2$, 0.2 mM DTT, 0.5% Triton X-100 (Roche, Indianapolis, Ind. #11332481001) and 1.0% DMSO in a total volume of 25 µl. The reaction is incubated for 120 minutes at room temperature and stopped by washing the plate 3 times with 50 µl/well wash buffer. Detection of the biotin-NAD+ incorporation is done using 25 µl/well of Strepavidin-HRP (GE Life Sciences Pittsburgh, Pa. #RPN1231V) diluted 1:3000 with wash buffer and incubated for 60 minutes at room temperature. The plate is then washed 3 times using 50 µl/well wash buffer. This is followed by incubation with 25 µl/well TMB peroxidase substrate kit (KPL, Gaithersburg, Md. #50-76-02 and #50-65-02) for 15 minutes at room temperature and stopping the reaction using 25 µl/well of 2 N H$_2$SO$_4$. The absorbance is read at 450 nm using an Envision model 2103.

By substantially following the procedures described above for hTNKS1, and using hTNKS2, an essentially similar ELISA assay is prepared.

Activity of those compounds tested against both hTNKS isoforms is shown in Table 7.

TABLE 7

| Example No. | hTNKS1 IC$_{50}$ (nM) | hTNKS2 IC$_{50}$ (nM) |
|---|---|---|
| 1 | 19.1 (±17.7, n = 13) | 13.7 (±7.77, n = 13) |
| 2 | 10.7 (±7.13, n = 6/7) | 6.25 (±1.20, n = 5) |
| 3 | 10.9 (±10.5, n = 4) | 6.58 (±4.48, n = 5) |
| 4 | 26.4 (±11.2, n = 5) | 11.6 (±6.88, n = 5) |
| 5 | 85.2 (±35.5, n = 8) | 69.4 (±17.6, n = 8) |
| 6 | 17.5 (±6.48, n = 3) | 9.95 |
| 7 | 41.9 (±19.9, n = 5) | 37.1 (±8.12, n = 5) |
| 8 | 94.8 (±2.99, n = 3/4) | 68.7 (±8.48, n = 3/4) |
| 9 | 83.3 (±89.4, n = 4) | 54.9 (±44.7, n = 4) |
| 10 | 158 (±89.0, n = 4) | 121 (±11.3, n = 4) |
| 11 | 32.7 (±29.9, n = 5) | 24.7 (±20.0, n = 5) |
| 12 | 27.5 (±32.7, n = 5) | 22.0 (±15.1, n = 5) |
| 13 | 14.9 (±9.89, n = 6/7) | 12.4 (±3.67, n = 6) |
| 14 | 22.8 (±13.0, n = 7) | 11.7 (±7.32, n = 6) |
| 15 | 25.3 (±5.05, n = 6/7) | 16.7 (±5.16, n = 5) |
| 16 | 55.1 (±32.5, n = 6) | 43.4 (±23.8, n = 4) |
| 17 | 67.6 (±64.7, n = 5) | 81.5 (±9.15, n = 4) |
| 18 | 114 (±84.2, n = 6) | 85.1 (±6.72, n = 5) |
| 19 | 19.9 (±6.75, n = 5) | 11.8 (±6.55, n = 5) |
| 20 | 31.8 (±38.2, n = 6) | 11.3 (±4.26, n = 5) |
| 28 | 29.5 (±47.3, n = 5) | 35.8 (±19.1, n = 4/5) |
| 29 | 18.4 (±13.3, n = 5) | 14.1 (±3.57, n = 5) |
| 30 | 41.7 (±40.2, n = 5) | 24.5 (±22.6, n = 5) |
| 31 | 15.2 (±5.04, n = 5) | 12.2 (±4.59, n = 5) |
| 32 | 37.2 (±39.7, n = 6) | 22.7 (±24.2, n = 6) |
| 33 | 35.8 (±32.5, n = 6) | 26.6 (±20.8, n = 6) |
| 34 | 47.6 (±36.6, n = 5) | 11.6 (±4.30, n = 4) |
| 35 | 21.6 | 7.54 |
| 36 | 26.2 (±2.55, n = 5) | 17.6 (±11.0, n = 5) |
| 37 | 19.8 (±13.3, n = 4) | 10.8 (±1.34, n = 4) |
| 38 | 45.3 (±32.0, n = 4) | 30.2 (±5.13, n = 4) |
| 39 | 30.3 (±26.6, n = 6) | 15.9 (±8.48, n = 6) |
| 40 | 14.3 (±4.89, n = 5) | 8.41 (±1.99, n = 5) |
| 41 | 14.5 (±10.7, n = 5) | 10.6 (±3.51, n = 5) |
| 42 | 19.8 (±15.9, n = 5) | 13.0 (±7.41, n = 5) |
| 43 | 34.3 (±12.7, n = 4) | 12.7 (±6.54, n = 4) |
| 44 | 17.6 (±8.49, n = 6) | 12.7 (±2.49, n = 6) |
| 45 | 37.3 (±11.1, n = 6) | 19.6 (±9.93, n = 6) |

Mean ± SEM;
SEM = standard error of the mean

Data in Table 7 provides evidence that the compounds tested have in vitro inhibitory activity against both isoforms of human tankyrases.

EGFP-Axin2 Stabilization Assay to Demonstrate Cell-Based Activity of Tankyrase Inhibitors Enhanced Green Fluorescent Protein-Axin2 cells (EGFP-Axin2) are prepared by stable transfection of HEK293 cells with an Axin2 construct containing an N-terminal truncated EGFP tag (amino acids 228-466; SEQ ID NO:7). Changes in Axin2 levels, specifically Axin2 stabilization, are monitored by quantitation of the level of EGFP in the stable cell line after various treatments in a 384-well format. Increases in fluorescence, reflecting the stabilization of the EGFP-Axin2 fusion protein as a consequence of tankyrase inhibition, are monitored in an Acumen Laser Scanning Cytometer.

HEK293 cells (ATCC, Manassas, Va. #CRL-1573) are maintained in complete medium of DMEM:F12 (Invitrogen™, Grand Island, N.Y. #93-0152DK) containing 5% FBS (Invitrogen™, Grand Island, N.Y. #10082-147), 20 mM HEPES (Hyclone, Logan, Utah #SH30237.01), and Glutamax (Invitrogen™, Grand Island, N.Y. #35050-061). EGFP-Axin2 cells are generated by transfecting HEK293 cells with full length human Axin2 (NCBI, Accession number NP_004646.3 (SEQ ID NO: 4)) containing a truncated (amino acids 228-466) EGFP N-terminal tag (full length EGFP, NCBI, Accession number ABG78037.1 (SEQ ID NO: 5) in pcDNA3.1+ (according to the manufacturer's protocol, Invitrogen™, Grand Island, N.Y. #V79020). Stable EGFP-Axin2 cells are maintained in HEK293 complete medium above with the addition of 800 μg/ml G418 (Invitrogen™ Grand Island, N.Y. #10131-035). The EGFP-Axin2 stabilization assay is done by plating 2000 EGFP-Axin2 cells/well in a poly-D-lysine coated BD 384-well plate (BD Biosciences, San Jose, Calif. #356663) and incubating in 30 μl/well complete HEK293 medium and grown overnight at 37° C., 5% $CO_2$. Compounds in 100% DMSO are added directly to the cell media at 100 nl/well. Final concentration of compounds tested in the assay is 33 μM-1.7 nM with final concentration of DMSO in the assay being 0.33%. Cells are incubated with compound for 24 hours at 37° C., 5% $CO_2$ and the cells fixed using 2% final concentration of formaldehyde for 15 minutes at room temperature. The fixed cells are washed twice for 20 minutes each in 40 μl/well PBS (Hyclone, Logan, Utah #SH30264.01) containing 0.1% Triton X-100 (Thermo Fisher Scientific, Waltham, Mass. #BP151-500). They are then stained using 30 μl/well PBS containing 10 μg/ml propidium iodide (Invitrogen™, Grand Island, N.Y. #P3566) and 50 μg/ml RNaseA (Sigma, St. Louis, Mo. #R6513). EGFP intensity is measured using an Acumen model eX3 Acumen Laser Scanning Cytometer gated to have 10% EGFP/cell.

TABLE 8

| Example No. | Axin2 Stabilization $EC_{50}$ (nM) |
|---|---|
| 1 | 65.9 (±22.7, n = 11) |
| 2 | 32.0 (±9.34, n = 4) |
| 3 | 18.4 (±15.8, n = 3) |
| 4 | 26.9 (±11.5, n = 3) |
| 5 | 115 (±78.3, n = 4) |
| 6 | 59.5 (±6.94, n = 4) |
| 7 | 121 (±21.9, n = 4) |
| 8 | 71.5 (±28.7, n = 5) |
| 9 | 70.9 (±30.6, n = 4) |
| 10 | 590 (±228, n = 3) |
| 11 | 119 (±26.6, n = 4) |
| 12 | 122 (±31.2, n = 4) |
| 13 | 101 (±26.8, n = 4) |
| 14 | 52.7 (±23.9, n = 4) |
| 15 | 115 (±17.5, n = 4) |
| 16 | 509 (±130, n = 3) |
| 17 | 198 (±57.4, n = 3) |
| 18 | 901 (±138, n = 3) |
| 19 | 62.6 (±14.6, n = 4) |
| 20 | 77.9 (±29.6, n = 3) |
| 28 | 130 (±79.4, n = 4) |
| 29 | 41.7 (±12.9, n = 3) |
| 30 | 57.7 (±27.1, n = 3) |
| 31 | 38.5 (±6.69, n = 3) |
| 32 | 136 (±84.8, n = 4) |
| 33 | 122 (±73.6, n = 4) |
| 34 | 156 (±141, n = 3) |
| 35 | 27.8 |
| 36 | 29.1 (±8.88, n = 3) |
| 37 | 23.9 (±4.48, n = 3) |
| 38 | 34.8 (±4.46, n = 3) |

TABLE 8-continued

| Example No. | Axin2 Stabilization $EC_{50}$ (nM) |
|---|---|
| 39 | 181 (±64.9, n = 5) |
| 40 | 39.8 (±16.2, n = 6) |
| 41 | 61.6 (±10.5, n = 4) |
| 42 | 141 (±44.0, n = 3) |
| 43 | 74.5 (±20.0, n = 4) |
| 44 | 118 (±33.2, n = 4) |
| 45 | 144 (±1.88 n = 3) |

Mean ± SEM;
SEM = standard error of the mean

Data in Table 8 provides evidence that the compounds tested stabilize Axin2 in HEK293 cells.

Human PARP1 Enzyme Assay to Assess Selectivity of Tankyrase Inhibitors (Vs. PARP1)

The Poly ADP-ribose polymerase 1(PARP1) assay is an ELISA which detects poly ADP ribose incorporated into plate-bound histone protein in a 384-well format. Using recombinant hPARP1 enzyme, this assay uses biotinylated NAD+ and measures the incorporation into histone using a streptavidin-horseradish peroxidase (HRP) conjugate and TMB peroxidase substrate to generate a colorimetric signal.

Histone is diluted to 0.1 mg/ml in coating buffer (50 mM $Na_2CO_3$, pH 9.4, Mallinckrodt, St. Louis, Mo.) and 25 μl is added to each well of a Corning 3700 plate. The plates are incubated overnight at 4° C. The next day the plates are washed 3× with 50 μl/well wash buffer (PBS (prepared from 10× concentrate) with 0.1% Tween-20) followed with blocking for 1.5 hours at room temperature using 50 μl 1% Casein block buffer in 1×PBS (Roche, Indianapolis, Ind. #11666789001). After blocking, the plates are washed 3 times with 50 μl/well wash buffer. The PARP1 enzyme assay is set up by using 0.01 U/μl hPARP1 (Trevigen, Gaithersburg, Md. #4668-500-01), 0.5×PARP cocktail, activated DNA (Trevigen, Gaithersburg, Md. #4671-096-03 and #4671-096-06) and compounds diluted from 10 μM to 4 nM final concentration in Assay buffer containing 50 mM Tris, pH 8.0, 10 mM $MgCl_2$, 1 mM DTT (Invitrogen™, Grand Island, N.Y. #15508-013), 0.5% Triton X-100 and 1.0% DMSO. The reaction is incubated for 60 minutes at room temperature and stopped by washing the plate 3 times with 50 μl/well wash buffer. Detection of the biotin-NAD+ incorporation is done using 25 μl/well of Strepavidin-HRP diluted 1:3000 with wash buffer and incubated for 60 minutes at room temperature. The plate is then washed 3 times using 50 μl/well wash buffer. This is followed by incubation with 25 μl/well TMB peroxidase substrate kit (KPL, Gaithersburg, Md. #50-76-02 and #50-65-02) for 15 minutes at room temperature and stopping the reaction using 25 μl/well of 2 N $H_2SO_4$. The absorbance is read at 450 nm using an Envision model 2103.

TABLE 9

| Example No. | PARP1 Inhibition $IC_{50}$ (nM) |
|---|---|
| 1 | 4,510 (±3030, n = 2) |
| 2 | 919 (n = 1/2) |
| 3 | 2,330 (±234, n = 2) |
| 4 | 3,020 (±197, n = 2) |
| 5 | 7,660 (±1450, n = 2) |
| 6 | 2,670 (±433, n = 2) |
| 7 | 5,930 (±647, n = 2) |

TABLE 9-continued

| Example No. | PARP1 Inhibition IC$_{50}$ (nM) |
|---|---|
| 8 | 5470 |
| 9 | 3940 |
| 10 | 33,700 (±3130, n = 2) |
| 11 | 13,500 |
| 12 | 5,050 |
| 13 | 3,470 (±318, n = 2) |
| 14 | 5,660 (±698, n = 2) |
| 15 | 6,910 (±746, n = 2) |
| 16 | 187 (±183, n = 2) |
| 17 | 7,220 (±1790, n = 2) |
| 18 | 77,600 (±24000, n = 2) |
| 19 | 5390 |
| 20 | 8,240 (±10800, n = 4) |
| 29 | 6,070 (±1730, n = 2) |
| 30 | 8,800 (±1720, n = 2) |
| 31 | 17,400 (±48.1, n = 2) |
| 32 | 21,500 (±2340, n = 2) |
| 33 | 15,300 (±2230, n = 2) |
| 34 | 16,200 (±5740, n = 2) |
| 36 | 95,700 (±6420, n = 2) |
| 37 | 2,440 (±598, n = 2) |
| 38 | 46,700 (±23700, n = 2) |
| 39 | 7,740 |
| 40 | 2,840 |
| 41 | 4,660 |
| 42 | 2,650 (±143, n = 2) |
| 43 | 6,390 (±1430, n = 2) |
| 44 | 5,830 (±229, n = 2) |
| 45 | 3,530 (±2030, n = 2) |

Mean ± SEM;
SEM = standard error of the mean

Data in Table 9 provides evidence as to each tested compound's selective inhibition of tankyrases when compared to PARP1 inhibition.

DLD-1 TOPFlash Assay to Determine the Ability of Tankyrase Inhibitors to Reduce the Expression of Wnt-Inducible Genes DLD-1 cells contain a mutation in the adenoma polyposis coli (APC) gene which encodes a truncated APC protein. This protein is incapable of binding the destruction complex and causes a constitutively activated Wnt pathway by allowing β catenin to translocate to the nucleus and activate the TCF/LEF transcription factors. DLD-1 TOPFlash is a reporter cell line derived from DLD-1 (human colorectal adenocarcinoma) cells by stable transfection of a TCF4 promoter linked to a luciferase reporter. The amount of luciferase in the cell lysates is quantitated by measuring luminescence in a 96 well format.

DLD-1 cells (ATCC, Manassas, Va., #CCL-221) are maintained in complete medium of RPMI (Invitrogen™, Grand Island, N.Y. #11875-093) containing 10% FBS (Hyclone, Logan, Utah #SH30070.03). DLD-1 TOPFlash cells are generated according to the manufacturer's protocol by infecting DLD-1 cells with Cignal Lenti TCF/LEF Reporter (Luc) (Qiagen, Valencia, Calif. #CLS-018L-8, lot#BX16) at an MOI of 10. Polybreen (Sigma, St. Louis, Mo. #H9268) is added to a final concentration of 8 μg/ml and the cells are incubated overnight at 37° C., 5% CO$_2$. The next day the medium is changed to fresh growth medium containing 10 μg/ml puromycin (Clontech, Mountain View, Calif. #631305) and the cells are incubated for an additional 3 days at 37° C., 5% CO$_2$ to generate a stable cell line. The TOPFlash assay is done by plating DLD-1 TOPFlash cells at 10,000 cells/well in a Corning 96 well white/clear plate (Corning Tewksbury, Mass. #3610) and incubating in 30 μl/well complete medium containing RPMI (Hyclone, Logan, Utah #SH30027.01), 10% FBS and 10 μg/ml puromycin and grown overnight at 37° C., 5% CO$_2$. The compounds in 100% DMSO are diluted 28.5 fold in OptiMEM® (Invitrogen™, Grand Island, N.Y. #31985-062) containing 0.2% BSA (diluted from 7.5% BSA Invitrogen™, Grand Island, N.Y. #15260-037) and 5 μl diluted compound added to the 30 μl cell culture medium/well. Final concentration of compounds tested in the assay is 50 μM-1.5 nM with final concentration of DMSO in the assay being 0.48%. Cells are incubated with compound for 24 hours at 37° C., 5% CO$_2$ and the plates removed from the incubator and placed at room temperature for 30 minutes. BugLite™ (3×) reagent is prepared by dissolving 2.296 g DTT (Sigma, St. Louis, Mo. #D0632), 1.152 g CoA (Sigma, St. Louis, Mo. #C3019), 0.248 g ATP (Sigma, St. Louis, Mo. #A7699), and 0.42 g Luciferin (Biosynth AG, Itasca, Ill. #L-8240) in 1 liter of Triton-X100 lysis buffer which contains 150 mM Tris (108.15 ml 1M Tris HCl and 41.85 ml 1M Tris Base (Sigma, St. Louis, Mo. #T3253 and T-1503)), 3 mM MgCl$_2$ and 3% Triton X-100. After the plates are equilibrated to room temperature, 18 μl of 3× BugLite reagent is added to each well and the plates are incubated at room temperature for 30 minutes with shaking. Luminescence is measured using an Envision model 2103.

TABLE 10

| Example No. | Wnt-inducible gene expression inhibition IC$_{50}$ (μM) |
|---|---|
| 1 | 0.0132 (±0.00595, n = 6) |
| 2 | 0.00817 (±0.00587, n = 4) |
| 3 | 0.00866 (±0.00190, n = 3) |
| 4 | 0.00671 (±0.00248, n = 3) |
| 5 | 0.0211 (±0.00437, n = 4) |
| 6 | 0.00720 (±0.00120, n = 2) |
| 7 | 0.0146 (±0.0128, n = 3) |
| 8 | 0.0184 (±0.0110, n = 3) |
| 9 | 0.0282 (±0.0257, n = 4) |
| 10 | 0.171 (±0.0474, n = 3) |
| 11 | 0.0281 (±0.00945, n = 3) |
| 12 | 0.0195 (±0.0111, n = 3) |
| 13 | 0.0230 (±0.0126, n = 3) |
| 14 | 0.00935 (±0.00872, n = 3) |
| 15 | 0.0154 (±0.00630, n = 3) |
| 16 | 0.102 (±0.0268, n = 3) |
| 17 | 0.0373 (±0.0103, n = 3) |
| 18 | 0.156 (±0.0724, n = 3) |
| 19 | 0.0126 (±0.00325, n = 3) |
| 20 | 0.0222 (±0.00155, n = 2) |
| 28 | 0.0228 (±0.0105, n = 3) |
| 29 | 0.0177 (+ 0.0138, n = 3) |
| 30 | 0.0168 (±0.0124, n = 3) |
| 31 | 0.0178 (±0.0119, n = 3) |
| 32 | 0.0201 (±0.0178, n = 3) |
| 33 | 0.0268 (±0.0229, n = 3) |
| 34 | 0.0236 (±0.0246, n = 3) |
| 35 | 0.0058 |
| 36 | 0.0208 (±0.0168, n = 3) |
| 37 | 0.00622 (±0.00286, n = 3) |
| 38 | 0.0222 (±0.00824, n = 3) |
| 39 | 0.0206 (±0.0129, n = 4) |
| 40 | 0.00695 (±0.00456, n = 4) |
| 41 | 0.0138 (±0.00253, n = 3) |
| 42 | 0.0220 (±0.00397, n = 3) |
| 43 | 0.0110 (±0.00217, n = 3) |
| 44 | 0.0112 (±0.00315, n = 3) |
| 45 | 0.0188 (±0.00510, n = 4) |

Mean ± SEM;
SEM = standard error of the mean

Data in Table 10 demonstrates that the compounds tested are inhibitors of Wnt inducible genes as measured by the TOPFlash Wnt reporter assay.

Assessment of In Vivo Antitumor Activity of Tankyrase Inhibitors

C57BL/6J-Apc$^{Min}$/J strain mice carry a truncating mutation at codon 850 of the Apc gene and develop intestinal polyps and colorectal neoplasms at the age of 3-6 months. Truncation in the APC gene leads to activation of the Wnt signaling pathway and elevated levels of β catenin are frequently detected in pre-neoplastic/neoplastic lesions in these mice.

In order to assess the in vivo antitumor activity of tankyrase inhibitors, C57BL/6J-Apc$^{Min}$/J strain mice are purchased from Jackson Laboratories (stock number 002020) and acclimated for 1 week Animals are divided into 2 groups and treated with either 25 mg/kg (BID) of Example 1 or vehicle for 60 consecutive days. At the end of the treatment period, the animals are sacrificed and the number of polyps in the small intestine is counted under a dissection microscope. As shown in Table 11, C57BL/6J-Apc$^{Min}$/J strain mice treated with the compound of Example 1 has a statistically significant lower number of tumors in the small intestine when compared to vehicle-treated animals.

TABLE 11

| Treatment | Number of Animals per Group | Average Number of polyps per Animal | p Value |
|---|---|---|---|
| Vehicle | 13 | 7.3 ± 0.53 | |
| Example 1 | 9 | 4.3 ± 0.70 | 0.0028 |

Data in Table 11 provides evidence that in vivo treatment with Example 1 reduces the number of intestinal polyps in C57BL/6J-Apc$^{Min}$J strain mice.

Colony Formation Assay

The compound of Example 1 is also tested in an in vitro colony formation assay against four different human tumor cell lines, three derived from pancreatic tumors (Capan-2, HPAF-II, and Panc 04.03) and one derived from non-small cell lung cancer (A549). This assay is carried out using commercially available materials by procedures known and routinely used by those skilled in the art.

A549 cells (ATCC, Manassas, Va. # CCL-185) are maintained in complete medium of F12K (Hyclone, Logan, Utah #SH30526) containing 10% FBS (Invitrogen, Grand Island, N.Y. #16000-044). Capan-2 cells (ATCC, Manassas, Va. # HTB-80) are maintained in complete medium of McCoys 5A (Hyclone, Logan, Utah #SH30200) containing 10% FBS (Invitrogen, Grand Island, N.Y. #16000-044). HPAF-II cells (ATCC, Manassas, Va. #CRL-1997) are maintained in complete medium of EMEM (Hyclone, Logan, Utah #SH30024) containing 10% FBS (Invitrogen, Grand Island, N.Y. #16000-044). Panc 04.03 cells (ATCC, Manassas, Va. #CRL-2555) are maintained in complete medium of RPMI (Hyclone, Logan, Utah #SH30255) containing 15% FBS (Invitrogen, Grand Island, N.Y. #16000-044) and 20 µg/ml Insulin (Sigma, St. Louis, Mo. #I9278). Colony formation assays are done by plating A549 cells at 250 cells/well; Capan-2 cells at 2000 cells/well; HPAF-II cells at 1000 cells/well or Panc 04.03 cells at 2000 cells/well each in a 6-well plate (Corning Life Sciences, Tewksbury, Mass. #353046), incubating in 2 ml complete medium and grown overnight at 37° C., 5% $CO_2$. The next day the medium is removed and replaced with 2 ml fresh respective growth medium for each cell line. Test compounds in 100% DMSO are diluted in 100% DMSO to 1000× concentration and 2 µl added to 2 ml of medium in the well to achieve a final concentration of 0.03 to 3 µM. Cells are incubated at 37° C., 5% $CO_2$. Every three to four days, the medium is removed and replaced with 2 ml fresh complete medium for each cell line as before. After the medium change, fresh compound is added as above. Cells are incubated a total of 11 days in the presence of compound. On day 11, the medium is removed and the cells washed once with 5 ml DPBS (Hyclone, Logan, Utah #SH30028). Crystal violet stain (0.5% crystal violet (Sigma, St Louis, Mo., #C3886) in 20% Methanol (EMD Millipore, Billerica, Mass. #MX0490-4) is added to each well (0.4 ml) and incubated at room temperature for 15 min. The wells are then washed twice with DPBS and the plates photographed using the Fuji LAS4000 (FujiFilm, Tokyo, Japan). Analysis of the colony area within each well is done using FujiFilm Colony Version 1.1 Software (FujiFilm, Tokyo, Japan).

TABLE 12

Effect of Compound of Example 1 on Colony Formation

| Compound of Example 1 Concentration | % Inhibition of Colony Formation | | | |
|---|---|---|---|---|
| | A549 | Capan-2 | HPAF-II | Panc 04.03 |
| Control | 0 | 0 | 0 | 0 |
| 0.03 µM | 25.46 | −20.82 | 2.44 | −34.35 |
| 0.11 µM | 46.50 | 18.04 | 40.47 | 51.39 |
| 0.33 µM | 54.23 | 55.90 | 61.65 | 92.79 |
| 1 µM | 74.35 | 63.92 | 85.22 | 92.51 |
| 3 µM | 72.07 | 70.73 | 88.23 | 90.03 |

The data in Table 12 evidences the compound of Example 1 inhibits colony formation when compared to control against each of the cell lines tested.

TABLE 13

| Polypeptide Used in Assays | Amino Acid Sequences |
|---|---|
| hTRF1 NCBI, Accession number NP_059523.2 | (SEQ ID NO: 1) |
| hTNKS1 NCBI, Accession number NP_003738.2 | (SEQ ID NO: 2) |
| hTNKS2 NCBI, Accession number NP_079511.1 | (SEQ ID NO: 3) |
| hAxin2 NCBI, Accession number NP_004646.3 | (SEQ ID NO: 4) |
| EGFP NCBI, Accession number ABG78037.1 | (SEQ ID NO: 5) |
| Flag Peptide Sigma-Aldrich | (SEQ ID NO: 6) |
| EGFP Amino acids 228-466 NCBI, Accession number ABG78037.1 | (SEQ ID NO: 7) |

Sequences hTRF1-protein

SEQ ID NO: 1
MAEDVSSAAPSPRGCADGRDADPTEEQMAETERNDEEQFECQELLECQV
QVGAPEEEEEEEEDAGLVAEAEAVAAGWMLDFLCLSLCRAFRDGRSEDF
RRTRNSAEAIIHGLSSLTACQLRTIYICQFLTRIAAGKTLDAQFENDER
ITPLESALMIWGSIEKEHDKLHEEIQNLIKIQAIAVCMENGNFKEAEEV
FERIFGDPNSHMPFKSKLLMIISQKDTFHSFFQHFSYNHMMEKIKSYVN
YVLSEKSSTFLMKAAAKVVESKRTRTITSQDKPSGNDVEMETEANLDTR
KSVSDKQSAVTESSEGTVSLLRSHKNLFLSKLQHGTQQQDLNKKERRVG
TPQSTKKKKESRRATESRIPVSKSQPVTPEKHRARKRQAWLWEEDKNLR
SGVRKYGEGNWSKILLHYKFNNRTSVMLKDRWRTMKKLKLISSDSED

Sequences hTNKS1-protein

SEQ ID NO: 2

MAASRRSQHHHHHHQQQLQPAPGASAPPPPPPPPLSPGLAPGTTPASPT
ASGLAPFASPRHGLALPEGDGSRDPPDRPRSPDPVDGTSCCSTTSTICT
VAAAPVVPAVSTSSAAGVAPNPAGSGSNNSPSSSSSPTSSSSSSPSSPG
SSLAESPEAAGVSSTAPLGPGAAGPGTGVPAVSGALRELLEACRNGDVS
RVKRLVDAANVNAKDMAGRKSSPLHFAAGFGRKDVVEHLLQMGANVHAR
DDDGGLIPLHNACSFGHAEVVSLLLCQGADPNARDNWNYTPLHEAAIKGK
IDVCIVLLQHGADPNIRNTDGKSALDLADPSAKAVLTGEYKKDELLEAA
RSGNEEKLMALLTPLNVNCHASDGRKSTPLHLAAGYNRVRIVQLLLQHG
ADVHAKDKGGLVPLHNACSYGHYEVTELLLKHGACVNAMDLWQFTPLHE
AASKNRVEVCSLLLSHGADPTLVNCHGKSAVDMAPTPELRERLTYEFKG
HSLLQAAREADLAKVKKTLALEIINFKQPQSHETALHCAVASLHPKRKQ
VTELLLRKGANVNEKNKDFMTPLHVAAERAHNDVMEVLHKHGAKMNALD
TLGQTALHRAALAGHLQTCRLLLSYGGDPSIISLQGFTAAQMGNEAVQQ
ILSESTPIRTSDVDYRLLEASKAGDLETVKQLCSSQNVRCRDLEGRHST
PLHFAAGYNRVSVVEYLLHHGADVHAKDKGGLVPLHNACSYGHYEVAEL
LVRHGASVNVADLWKFTPLHEAAAKGKYEICKLLLKHGADPTKKNRDGN
TPLDLVKEGDTDIQDLLRGDAALLDAAKKGCLARVQKLCTPENINCRDT
QGRNSTPLHLAAGYNNLEVAEYLLEHGADVNAQDKGGLIPLHNAASYGH
VDIAALLIKYNTCVNATDKWAFTPLHEAAQKGRTQLCALLLAHGADPTM
KNQEGQTPLDLATADDIRALLIDAMPPEALPTCFKPQATVVSASLISPA
STPSCLSAASSIDNLTGPLAELAVGGASNAGDGAAGTERKEGEVAGLDM
NISQFLKSLGLEHLRDIFETEQITLDVLADMGHEELKEIGINAYGHRHK
LIKGVERLLGGQQGTNPYLTFHCVNQGTILLDLAPEDKEYQSVEEEMQS
TIREHRDGGNAGGIFNRYNVIRIQKVVNKKLRERFCHRQKEVSEENHHN
HNERMLFHGSPFINAIIHKGFDERHAYIGGMFGAGIYFAENSSKSNQYV
YGIGGGTGCPTHKDRSCYICHRQMLFCRVTLGKSFLQFSTMKMAHAPPG
HHSVIGRPSVNGLAYAEYVIYRGEQAYPEYLITYQIMKPEAPSQTATAA
EQKT hTNKS2-protein

SEQ ID NO: 3

MSGRRCAGGGAACASAAAEAVEPAARELFEACRNGDVERVKRLVTPEKV
NSRDTAGRKSTPLHFAAGFGRKDVVEYLLQNGANVQARDDGGLIPLHNA
CSFGHAEVVNLLLRHGADPNARDNWNYTPLHEAAIKGKIDVCIVLLQHG
AEPTIRNTDGRTALDLADPSAKAVLTGEYKKDELLESARSGNEEKMMAL
LTPLNVNCHASDGRKSTPLHLAAGYNRVKIVQLLLQHGADVHAKDKGDL
VPLHNACSYGHYEVTELLVKHGACVNAMDLWQFTPLHEAASKNRVEVCS
LLLSYGADPTLLNCHNKSAIDLAPTPQLKERLAYEFKGHSLLQAAREAD
VTRIKKHLSLEMVNFKHPQTHETALHCAAASPYPKRKQICELLLRKGAN
INEKTKEFLTPLHVASEKAHNDVVEVVVKHEAKVNALDNLGQTSLHRAA
YCGHLQTCRLLLSYGCDPNIISLQGFTALQMGNENVQQLLQEGISLGNS
EADRQLLEAAKAGDVETVKKLCTVQSVNCRDIEGRQSTPLHFAAGYNRV
SVVEYLLQHGADVHAKDKGGLVPLHNACSYGHYEVAELLVKHGAVVNVA
DLWKFTPLHEAAAKGKYEICKLLLQHGADPTKKNRDGNTPLDLVKDGDT
DIQDLLRGDAALLDAAKKGCLARVKKLSSPDNVNCRDTQGRHSTPLHLA
AGYNNLEVAEYLLQHGADVNAQDKGGLIPLHNAASYGHVDVAALLIKYN
ACVNATDKWAFTPLHEAAQKGRTQLCALLLAHGADPTLKNQEGQTPLDL
VSADDVSALLTAAMPPSALPSCYKPQVLNGVRSPGATADALSSGPSSPS
SLSAASSLDNLSGSFSELSSVVSSSGTEGASSLEKKEVPGVDFSITQFV
RNLGLEHLMDIFEREQITLDVLVEMGHKELKEIGINAYGHRHKLIKGVE

RLISGQQGLNPYLTLNTSGSGTILIDLSPDDKEFQSVEEEMQSTVREHR
DGGHAGGIFNRYNILKIQKVCNKKLWERYTHRRKEVSEENHNHANERML
FHGSPFVNAIIHKGFDERHAYIGGMFGAGIYFAENSSKSNQYVVGIGGG
TGCPVHKDRSCYICHRQLLFCRVTLGKSFLQFSAMKMAHSPPGHHSVTG
RPSVNGLALAEYVIYRGEQAYPEYLITYQIMRPEGMVDG hAxin2-protein

SEQ ID NO: 4

MSSAMLVTCLPDPSSSFREDAPRPPVPGEEGETPPCQPGVGKGQVTKPM
PVSSNTRRNEDGLGEPEGRASPDSPLTRWTKSLHSLLGDQDGAYLFRTF
LEREKCVDTLDFWFACNGRFRQMNLKDTKTLRVAKAIYKRYIENNSIVSK
QLKPATKTYIRDGIKKQQIDSIMFDQAQTEIQSVMEENAYQMFLTSDIY
LEYVRSGGENTAYMSNGGLGSLKVVCGYLPTLNEEEEWTCADFKCKLSP
TVVGLSSKTLRATASVRSTETVDSGYRSFKRSDPVNPYHIGSGYVFAPA
TSANDSEISSDALTDDSMSMTDSSVDGIPPYRVGSKKQLQREMHRSVKA
NGQVSLPHFPRTHRLPKEMTPVEPATFAAELISRLEKLKLELESRHSLE
ERLQQIREDEEREGSELTLNSREGAPTQHPLSLLPSGSYEEDPQTILDD
HLSRVLKTPGCQSPGVGRYSPRSRSPDHHHHHHSQYHSLLPPGGKLPPA
AASPGACPLLGGKGFVTKQTTKHVHHHYIHHHAVPKTKEEIEAEATQRV
HCFCPGGSEYYCYSKCKSHSKAPETMPSEQFGGSRGSTLPKRNGKGTEP
GLALPAREGGAPGGAGALQLPREEGDRSQDVWQWMLESERQSKPKPHSA
QSTKKAYPLESARSSPGERASRHHLWGGNSGHPRTTPRAHLFTQDPAMP
PLTPPNTLAQLEEACRRLAEVSKPPKQRCCVASQQRDRNHSATVQTGAT
PFSNPSLAPEDHKEPKKLAGVHALQASELVVTYFFCGEEIPYRRMLKAQ
SLTLGHFKEQLSKKGNYRYYFKKASDEFACGAVFEEIWEDETVLPMYEG
RILGKVERID

EGFP-full length protein

SEQ ID NO: 5

MDRKFVFLVSILSIVVASVTGETTRAPTPTPTPTPTPTPTPTPTPTPTP
TPTPTPTPTPTPTPTPTPTPTPTPTPTPTPTPTPTPTPTPTPTPTPTPT
PTPTPTPTPTPTPTPTPTPTPTPTPTPTPTPTPTPTPTPTPTPTPTPTP
TPTPTPTPTPTPTPTPTPTPTPTPTPTPTPTPTPTPTPTPTPTPTPTPT
PTPTPTPTPTPTPTPTPTPTPTPTPSMVSKGEELFTGVVPILVE
LDGDVNGHKFSVSGEGEGDATYGKLTLKFICTTGKLPVPWPTLVTTLTY
GVQCFSRYPDHMKQHMKSAMPEGYVQERTIFFKDDGNYKTRAEVKFEGD
TLVNRIELKGIDFKEDGNLGHKLEYNYNSHNVYIMADKQKNGIKVNFK
IRHNIEDGSVQLADHYQQNTPIGDGPVLLPDNHYLSTQSALSKDPNEKR
DHMVLLEFVTAAGITLGMDELYK

Flag Peptide

SEQ ID NO: 6

DYKDDDDK

EGFP-truncated protein amino acids 228-466

SEQ ID NO: 7

MVSKGEELFTGVVPILVELDGDVNGHKFSVSGEGEGDATYGKLTLKFIC
TTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYN
SHNVYIMADKQKNGIKVNFKIRHNIEDGSVQLADHYQQNTPIGDGPVLL
PDNHYLSTQSALSKDPNEKRDHMVLLEFVTAAGITLGMDELYK

We claim:

1. A compound having the formula:

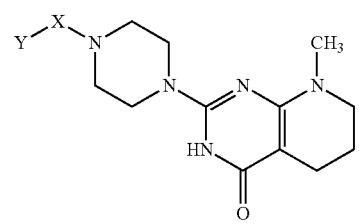

wherein:

Y is:

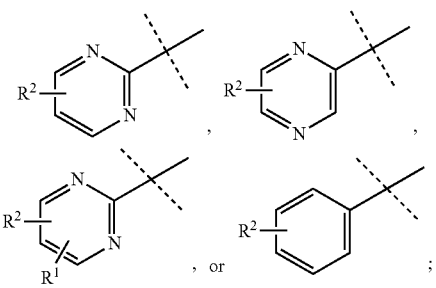

X is —CH$_2$—, —C(CH$_3$)H—, or —C(CH$_2$CH$_3$)H—;
R$^1$ is hydrogen, hydroxy, or halo;
R$^2$ is hydrogen, halo, —CN, —CH$_3$, CF$_3$, or —OCH$_3$;
or a pharmaceutically acceptable salt thereof.

2. A compound of claim 1 wherein:

Y is:

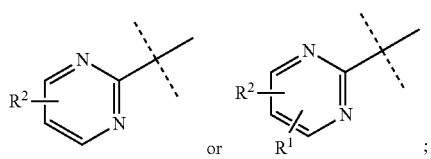

X is —CH$_2$—, —C(CH$_3$)H—, or —C(CH$_2$CH$_3$)H—;
R$^1$ is hydrogen, hydroxy, or halo;
R$^2$ is hydrogen, halo, —CN, —CH$_3$, CF$_3$, or —OCH$_3$;
or a pharmaceutically acceptable salt thereof.

3. A compound of claim 2 wherein:

Y is

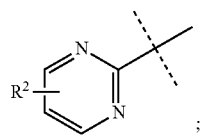

X is —CH$_2$—, —C(CH$_3$)H—, or —C(CH$_2$CH$_3$)H—;
R$^2$ is hydrogen, halo, —CN, —CH$_3$, CF$_3$, or —OCH$_3$;
or a pharmaceutically acceptable salt thereof.

4. A compound of claim 2 wherein:
Y is:

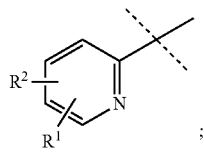

X is —CH₂—, —C(CH₃)H—, or —C(CH₂CH₃)H—;
R¹ is hydrogen, hydroxy, or halo;
R² is hydrogen, halo, —CN, —CH₃, CF₃, or —OCH₃;
or a pharmaceutically acceptable salt thereof.

5. A compound of claim 3 which is:
8-Methyl-2-[4-(pyrimidin-2-ylmethyl)piperazin-1-yl]-3,5,6,7-tetrahydropyrido[2,3-d]pyrimidin-4-one, or a pharmaceutically acceptable salt thereof;
8-Methyl-2-[4-(1-pyrimidin-2-ylethyl)piperazin-1-yl]-3,5,6,7-tetrahydropyrido[2,3-d]pyrimidin-4-one, or a pharmaceutically acceptable salt thereof thereof;
2-[4-[(4-Chloropyrimidin-2-yl)methyl]piperazin-1-yl]-8-methyl-3,5,6,7-tetrahydropyrido[2,3-d]pyrimidin-4-one, or a pharmaceutically acceptable salt thereof; or
2-[4-[(4-methoxypyrimidin-2-yl)methyl]piperazin-1-yl]-8-methyl-3,5,6,7-tetrahydropyrido[2,3-d]pyrimidin-4-one, or a pharmaceutically acceptable salt thereof.

6. A compound of claim 4 which is:
2-[4-[(3-Bromo-2-pyridyl)methyl)]piperazin-1-yl]-8-methyl-3,5,6,7-tetrahydropyrido[2,3-d]pyrimidin-4-one or a pharmaceutically acceptable salt thereof;
2-[4-[(3-Chloro-2-pyridyl)methyl]piperazin-1-yl]-8-methyl-3,5,6,7-tetrahydropyrido[2,3-d]pyrimidin-4-one, or a pharmaceutically acceptable salt thereof;
2-[4-[(3-Fluoro-2-pyridyl)methyl]piperazin-1-yl]-8-methyl-3,5,6,7-tetrahydropyrido[2,3-d]pyrimidin-4-one, or a pharmaceutically acceptable salt thereof; or
2-[[4-(8-Methyl-4-oxo-3,5,6,7-tetrahydropyrido[2,3-d]pyrimidin-2-yl)piperazin-1-yl]methyl]pyridine-3-carbonitrile, or a pharmaceutically acceptable salt thereof.

7. A compound of claim 5 which is 8-methyl-2-[4-(pyrimidin-2-ylmethyl)piperazin-1-yl]-3,5,6,7-tetrahydropyrido[2,3-d]pyrimidin-4(3H)-one, or a pharmaceutically acceptable salt thereof.

8. A compound of claim 7 which is 8-Methyl-2-[4-(pyrimidin-2-ylmethyl)piperazin-1-yl]-3,5,6,7-tetrahydropyrido[2,3-d]pyrimidin-4-one 4-methylbenzenesulfonic acid salt.

9. A pharmaceutical composition comprising a compound of claim 1, or a pharmaceutically acceptable salt thereof, in a pharmaceutically acceptable carrier.

* * * * *

UNITED STATES PATENT AND TRADEMARK OFFICE
CERTIFICATE OF CORRECTION

PATENT NO. : 9,624,218 B2
APPLICATION NO. : 15/027301
DATED : April 18, 2017
INVENTOR(S) : Marcio Chedid It is certified that error appears in the above-identified patent and that said Letters Patent is hereby corrected as shown below:

In Column 79, Claim 1, Line 5, please delete " 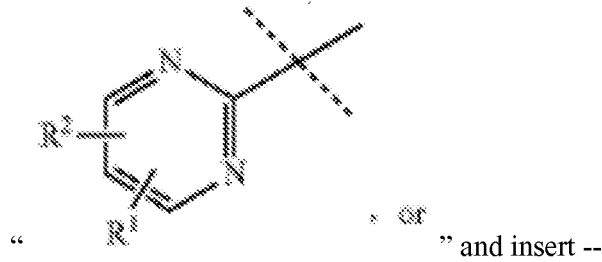 " and insert -- 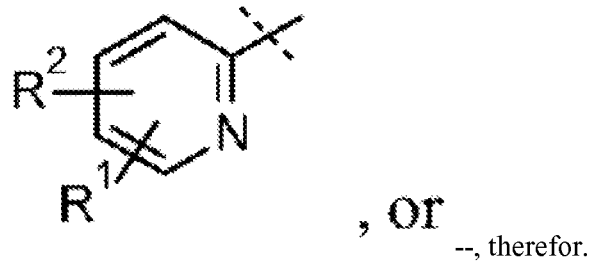 --, therefor.

In Column 80, Claim 2, Line 3, please delete " 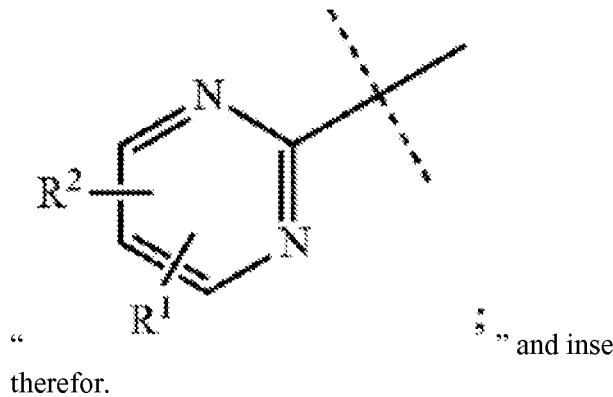 " and insert -- 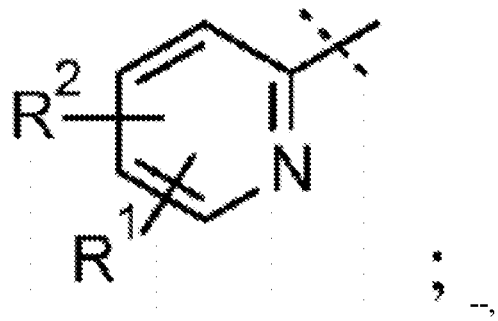 --, therefor.

In Column 81, approximately Line 13, please delete "R¹'" and insert -- $R^1$ --, therefor.

Signed and Sealed this
Thirteenth Day of June, 2017

Joseph Matal
*Performing the Functions and Duties of the
Under Secretary of Commerce for Intellectual Property and
Director of the United States Patent and Trademark Office*

SEQUENCE LISTING

<160> NUMBER OF SEQ ID NOS: 7

<210> SEQ ID NO 1
<211> LENGTH: 439
<212> TYPE: PRT
<213> ORGANISM: Homo sapiens

<400> SEQUENCE: 1

Met Ala Glu Asp Val Ser Ser Ala Ala Pro Ser Pro Arg Gly Cys Ala
1               5                   10                  15

Asp Gly Arg Asp Ala Asp Pro Thr Glu Glu Gln Met Ala Glu Thr Glu
            20                  25                  30

Arg Asn Asp Glu Glu Gln Phe Glu Cys Gln Glu Leu Leu Glu Cys Gln
        35                  40                  45

Val Gln Val Gly Ala Pro Glu Glu Glu Glu Glu Glu Asp Ala
    50              55                  60

Gly Leu Val Ala Glu Ala Glu Ala Val Ala Ala Gly Trp Met Leu Asp
65              70                  75                  80

Phe Leu Cys Leu Ser Leu Cys Arg Ala Phe Arg Asp Gly Arg Ser Glu
                85                  90                  95

Asp Phe Arg Arg Thr Arg Asn Ser Ala Glu Ala Ile Ile His Gly Leu
            100                 105                 110

Ser Ser Leu Thr Ala Cys Gln Leu Arg Thr Ile Tyr Ile Cys Gln Phe
            115                 120                 125

Leu Thr Arg Ile Ala Ala Gly Lys Thr Leu Asp Ala Gln Phe Glu Asn
130                 135                 140

Asp Glu Arg Ile Thr Pro Leu Glu Ser Ala Leu Met Ile Trp Gly Ser
145                 150                 155                 160

Ile Glu Lys Glu His Asp Lys Leu His Glu Glu Ile Gln Asn Leu Ile
                165                 170                 175

Lys Ile Gln Ala Ile Ala Val Cys Met Glu Asn Gly Asn Phe Lys Glu
            180                 185                 190

Ala Glu Glu Val Phe Glu Arg Ile Phe Gly Asp Pro Asn Ser His Met
            195                 200                 205

Pro Phe Lys Ser Lys Leu Leu Met Ile Ile Ser Gln Lys Asp Thr Phe
210                 215                 220

His Ser Phe Phe Gln His Phe Ser Tyr Asn His Met Met Glu Lys Ile
225                 230                 235                 240

Lys Ser Tyr Val Asn Tyr Val Leu Ser Glu Lys Ser Ser Thr Phe Leu
                245                 250                 255

Met Lys Ala Ala Ala Lys Val Val Glu Ser Lys Arg Thr Arg Thr Ile
            260                 265                 270

Thr Ser Gln Asp Lys Pro Ser Gly Asn Asp Val Glu Met Glu Thr Glu
            275                 280                 285

Ala Asn Leu Asp Thr Arg Lys Ser Val Ser Asp Lys Gln Ser Ala Val
290                 295                 300

Thr Glu Ser Ser Glu Gly Thr Val Ser Leu Leu Arg Ser His Lys Asn
305                 310                 315                 320

Leu Phe Leu Ser Lys Leu Gln His Gly Thr Gln Gln Gln Asp Leu Asn
                325                 330                 335

Lys Lys Glu Arg Arg Val Gly Thr Pro Gln Ser Thr Lys Lys Lys Lys
            340                 345                 350

Glu Ser Arg Arg Ala Thr Glu Ser Arg Ile Pro Val Ser Lys Ser Gln
            355                 360                 365

Pro Val Thr Pro Glu Lys His Arg Ala Arg Lys Arg Gln Ala Trp Leu
370                 375                 380

Trp Glu Glu Asp Lys Asn Leu Arg Ser Gly Val Arg Lys Tyr Gly Glu
385                 390                 395                 400

Gly Asn Trp Ser Lys Ile Leu Leu His Tyr Lys Phe Asn Asn Arg Thr
                405                 410                 415

Ser Val Met Leu Lys Asp Arg Trp Arg Thr Met Lys Lys Leu Lys Leu
            420                 425                 430

Ile Ser Ser Asp Ser Glu Asp
            435

<210> SEQ ID NO 2
<211> LENGTH: 1327
<212> TYPE: PRT

<213> ORGANISM: Homo sapiens

<400> SEQUENCE: 2

```
Met Ala Ala Ser Arg Ser Gln His His His His His Gln Gln
 1               5                  10                  15

Gln Leu Gln Pro Ala Pro Gly Ala Ser Ala Pro Pro Pro Pro
                20                  25                  30

Pro Pro Leu Ser Pro Gly Leu Ala Pro Gly Thr Thr Pro Ala Ser Pro
            35                  40                  45

Thr Ala Ser Gly Leu Ala Pro Phe Ala Ser Pro Arg His Gly Leu Ala
 50                  55                  60

Leu Pro Glu Gly Asp Gly Ser Arg Asp Pro Asp Arg Pro Arg Ser
 65                  70                  75                  80

Pro Asp Pro Val Asp Gly Thr Ser Cys Cys Ser Thr Thr Ser Thr Ile
                85                  90                  95

Cys Thr Val Ala Ala Ala Pro Val Val Pro Ala Val Ser Thr Ser Ser
                100                 105                 110

Ala Ala Gly Val Ala Pro Asn Pro Ala Gly Ser Gly Ser Asn Asn Ser
                115                 120                 125

Pro Ser Ser Ser Ser Pro Thr Ser Ser Ser Ser Ser Pro Ser
130                 135                 140

Ser Pro Gly Ser Ser Leu Ala Glu Ser Pro Glu Ala Ala Gly Val Ser
145                 150                 155                 160

Ser Thr Ala Pro Leu Gly Pro Gly Ala Ala Gly Pro Gly Thr Gly Val
                165                 170                 175

Pro Ala Val Ser Gly Ala Leu Arg Glu Leu Leu Glu Ala Cys Arg Asn
                180                 185                 190

Gly Asp Val Ser Arg Val Lys Arg Leu Val Asp Ala Ala Asn Val Asn
                195                 200                 205

Ala Lys Asp Met Ala Gly Arg Lys Ser Ser Pro Leu His Phe Ala Ala
210                 215                 220

Gly Phe Gly Arg Lys Asp Val Val Glu His Leu Leu Gln Met Gly Ala
225                 230                 235                 240

Asn Val His Ala Arg Asp Asp Gly Gly Leu Ile Pro Leu His Asn Ala
                245                 250                 255

Cys Ser Phe Gly His Ala Glu Val Val Ser Leu Leu Leu Cys Gln Gly
                260                 265                 270

Ala Asp Pro Asn Ala Arg Asp Asn Trp Asn Tyr Thr Pro Leu His Glu
                275                 280                 285

Ala Ala Ile Lys Gly Lys Ile Asp Val Cys Ile Val Leu Leu Gln His
                290                 295                 300

Gly Ala Asp Pro Asn Ile Arg Asn Thr Asp Gly Lys Ser Ala Leu Asp
305                 310                 315                 320

Leu Ala Asp Pro Ser Ala Lys Ala Val Leu Thr Gly Glu Tyr Lys Lys
                325                 330                 335

Asp Glu Leu Leu Glu Ala Ala Arg Ser Gly Asn Glu Glu Lys Leu Met
                340                 345                 350

Ala Leu Leu Thr Pro Leu Asn Val Asn Cys His Ala Ser Asp Gly Arg
                355                 360                 365

Lys Ser Thr Pro Leu His Leu Ala Ala Gly Tyr Asn Arg Val Arg Ile
                370                 375                 380

Val Gln Leu Leu Leu Gln His Gly Ala Asp Val His Ala Lys Asp Lys
385                 390                 395                 400
```

```
Gly Gly Leu Val Pro Leu His Asn Ala Cys Ser Tyr Gly His Tyr Glu
            405                 410                 415
Val Thr Glu Leu Leu Lys His Gly Ala Cys Val Asn Ala Met Asp
        420                 425                 430
Leu Trp Gln Phe Thr Pro Leu His Glu Ala Ala Ser Lys Asn Arg Val
        435                 440                 445
Glu Val Cys Ser Leu Leu Leu Ser His Gly Ala Asp Pro Thr Leu Val
450                 455                 460
Asn Cys His Gly Lys Ser Ala Val Asp Met Ala Pro Thr Pro Glu Leu
465                 470                 475                 480
Arg Glu Arg Leu Thr Tyr Glu Phe Lys Gly His Ser Leu Leu Gln Ala
                485                 490                 495
Ala Arg Glu Ala Asp Leu Ala Lys Val Lys Lys Thr Leu Ala Leu Glu
            500                 505                 510
Ile Ile Asn Phe Lys Gln Pro Gln Ser His Glu Thr Ala Leu His Cys
            515                 520                 525
Ala Val Ala Ser Leu His Pro Lys Arg Lys Gln Val Thr Glu Leu Leu
            530                 535                 540
Leu Arg Lys Gly Ala Asn Val Asn Glu Lys Asn Lys Asp Phe Met Thr
545                 550                 555                 560
Pro Leu His Val Ala Ala Glu Arg Ala His Asn Asp Val Met Glu Val
                565                 570                 575
Leu His Lys His Gly Ala Lys Met Asn Ala Leu Asp Thr Leu Gly Gln
                580                 585                 590
Thr Ala Leu His Arg Ala Leu Ala Gly His Leu Gln Thr Cys Arg
            595                 600                 605
Leu Leu Leu Ser Tyr Gly Ser Asp Pro Ser Ile Ile Ser Leu Gln Gly
            610                 615                 620
Phe Thr Ala Ala Gln Met Gly Asn Glu Ala Val Gln Gln Ile Leu Ser
625                 630                 635                 640
Glu Ser Thr Pro Ile Arg Thr Ser Asp Val Asp Tyr Arg Leu Leu Glu
                645                 650                 655
Ala Ser Lys Ala Gly Asp Leu Glu Thr Val Lys Gln Leu Cys Ser Ser
            660                 665                 670
Gln Asn Val Asn Cys Arg Asp Leu Glu Gly Arg His Ser Thr Pro Leu
            675                 680                 685
His Phe Ala Ala Gly Tyr Asn Arg Val Ser Val Val Glu Tyr Leu Leu
            690                 695                 700
His His Gly Ala Asp Val His Ala Lys Asp Lys Gly Gly Leu Val Pro
705                 710                 715                 720
Leu His Asn Ala Cys Ser Tyr Gly His Tyr Glu Val Ala Glu Leu Leu
                725                 730                 735
Val Arg His Gly Ala Ser Val Asn Val Ala Asp Leu Trp Lys Phe Thr
                740                 745                 750
Pro Leu His Glu Ala Ala Ala Lys Gly Lys Tyr Glu Ile Cys Lys Leu
            755                 760                 765
Leu Leu Lys His Gly Ala Asp Pro Thr Lys Lys Asn Arg Asp Gly Asn
        770                 775                 780
Thr Pro Leu Asp Leu Val Lys Glu Gly Asp Thr Asp Ile Gln Asp Leu
785                 790                 795                 800
Leu Arg Gly Asp Ala Ala Leu Leu Asp Ala Ala Lys Lys Gly Cys Leu
            805                 810                 815
Ala Arg Val Gln Lys Leu Cys Thr Pro Glu Asn Ile Asn Cys Arg Asp
```

-continued

```
                820                 825                 830
Thr Gln Gly Arg Asn Ser Thr Pro Leu His Leu Ala Ala Gly Tyr Asn
                    835                 840                 845

Asn Leu Glu Val Ala Glu Tyr Leu Leu Glu His Gly Ala Asp Val Asn
850                 855                 860

Ala Gln Asp Lys Gly Gly Leu Ile Pro Leu His Asn Ala Ala Ser Tyr
865                 870                 875                 880

Gly His Val Asp Ile Ala Ala Leu Leu Ile Lys Tyr Asn Thr Cys Val
                    885                 890                 895

Asn Ala Thr Asp Lys Trp Ala Phe Thr Pro Leu His Glu Ala Ala Gln
                    900                 905                 910

Lys Gly Arg Thr Gln Leu Cys Ala Leu Leu Leu Ala His Gly Ala Asp
                    915                 920                 925

Pro Thr Met Lys Asn Gln Glu Gly Gln Thr Pro Leu Asp Leu Ala Thr
                    930                 935                 940

Ala Asp Asp Ile Arg Ala Leu Leu Ile Asp Ala Met Pro Pro Glu Ala
945                 950                 955                 960

Leu Pro Thr Cys Phe Lys Pro Gln Ala Thr Val Val Ser Ala Ser Leu
                    965                 970                 975

Ile Ser Pro Ala Ser Thr Pro Ser Cys Leu Ser Ala Ala Ser Ser Ile
                    980                 985                 990

Asp Asn Leu Thr Gly Pro Leu Ala Glu Leu Ala Val Gly Gly Ala Ser
                    995                 1000                1005

Asn Ala Gly Asp Gly Ala Ala Gly Thr Glu Arg Lys Glu Gly Glu
            1010                1015                1020

Val Ala Gly Leu Asp Met Asn Ile Ser Gln Phe Leu Lys Ser Leu
            1025                1030                1035

Gly Leu Glu His Leu Arg Asp Ile Phe Glu Thr Glu Gln Ile Thr
            1040                1045                1050

Leu Asp Val Leu Ala Asp Met Gly His Glu Glu Leu Lys Glu Ile
            1055                1060                1065

Gly Ile Asn Ala Tyr Gly His Arg His Lys Leu Ile Lys Gly Val
            1070                1075                1080

Glu Arg Leu Leu Gly Gly Gln Gln Gly Thr Asn Pro Tyr Leu Thr
            1085                1090                1095

Phe His Cys Val Asn Gln Gly Thr Ile Leu Leu Asp Leu Ala Pro
            1100                1105                1110

Glu Asp Lys Glu Tyr Gln Ser Val Glu Glu Met Gln Ser Thr
            1115                1120                1125

Ile Arg Glu His Arg Asp Gly Gly Asn Ala Gly Ile Phe Asn
            1130                1135                1140

Arg Tyr Asn Val Ile Arg Ile Gln Lys Val Val Asn Lys Lys Leu
            1145                1150                1155

Arg Glu Arg Phe Cys His Arg Gln Lys Glu Val Ser Glu Glu Asn
            1160                1165                1170

His Asn His His Asn Glu Arg Met Leu Phe His Gly Ser Pro Phe
            1175                1180                1185

Ile Asn Ala Ile Ile His Lys Gly Phe Asp Glu Arg His Ala Tyr
            1190                1195                1200

Ile Gly Gly Met Phe Gly Ala Gly Ile Tyr Phe Ala Glu Asn Ser
            1205                1210                1215

Ser Lys Ser Asn Gln Tyr Val Tyr Gly Ile Gly Gly Gly Thr Gly
            1220                1225                1230
```

```
Cys Pro Thr His Lys Asp Arg Ser Cys Tyr Ile Cys His Arg Gln
    1235                1240                1245

Met Leu Phe Cys Arg Val Thr Leu Gly Lys Ser Phe Leu Gln Phe
    1250                1255                1260

Ser Thr Met Lys Met Ala His Ala Pro Pro Gly His His Ser Val
    1265                1270                1275

Ile Gly Arg Pro Ser Val Asn Gly Leu Ala Tyr Ala Glu Tyr Val
    1280                1285                1290

Ile Tyr Arg Gly Glu Gln Ala Tyr Pro Glu Tyr Leu Ile Thr Tyr
    1295                1300                1305

Gln Ile Met Lys Pro Glu Ala Pro Ser Gln Thr Ala Thr Ala Ala
    1310                1315                1320

Glu Gln Lys Thr
    1325

<210> SEQ ID NO 3
<211> LENGTH: 1166
<212> TYPE: PRT
<213> ORGANISM: Homo sapiens

<400> SEQUENCE: 3

Met Ser Gly Arg Arg Cys Ala Gly Gly Gly Ala Ala Cys Ala Ser Ala
1               5                   10                  15

Ala Ala Glu Ala Val Glu Pro Ala Ala Arg Glu Leu Phe Glu Ala Cys
                20                  25                  30

Arg Asn Gly Asp Val Glu Arg Val Lys Arg Leu Val Thr Pro Glu Lys
            35                  40                  45

Val Asn Ser Arg Asp Thr Ala Gly Arg Lys Ser Thr Pro Leu His Phe
        50                  55                  60

Ala Ala Gly Phe Gly Arg Lys Asp Val Val Glu Tyr Leu Leu Gln Asn
65                  70                  75                  80

Gly Ala Asn Val Gln Ala Arg Asp Gly Gly Leu Ile Pro Leu His
                85                  90                  95

Asn Ala Cys Ser Phe Gly His Ala Glu Val Val Asn Leu Leu Leu Arg
                100                 105                 110

His Gly Ala Asp Pro Asn Ala Arg Asp Asn Trp Asn Tyr Thr Pro Leu
            115                 120                 125

His Glu Ala Ala Ile Lys Gly Lys Ile Asp Val Cys Ile Val Leu Leu
        130                 135                 140

Gln His Gly Ala Glu Pro Thr Ile Arg Asn Thr Asp Gly Arg Thr Ala
145                 150                 155                 160

Leu Asp Leu Ala Asp Pro Ser Ala Lys Ala Val Leu Thr Gly Glu Tyr
                165                 170                 175

Lys Lys Asp Glu Leu Leu Glu Ser Ala Arg Ser Gly Asn Glu Glu Lys
            180                 185                 190

Met Met Ala Leu Leu Thr Pro Leu Asn Val Asn Cys His Ala Ser Asp
        195                 200                 205

Gly Arg Lys Ser Thr Pro Leu His Leu Ala Ala Gly Tyr Asn Arg Val
    210                 215                 220

Lys Ile Val Gln Leu Leu Leu Gln His Gly Ala Asp Val His Ala Lys
225                 230                 235                 240

Asp Lys Gly Asp Leu Val Pro Leu His Asn Ala Cys Ser Tyr Gly His
                245                 250                 255

Tyr Glu Val Thr Glu Leu Leu Val Lys His Gly Ala Cys Val Asn Ala
```

```
                260             265             270
Met Asp Leu Trp Gln Phe Thr Pro Leu His Glu Ala Ala Ser Lys Asn
            275             280             285

Arg Val Glu Val Cys Ser Leu Leu Ser Tyr Gly Ala Asp Pro Thr
            290             295             300

Leu Leu Asn Cys His Asn Lys Ser Ala Ile Asp Leu Ala Pro Thr Pro
305             310             315             320

Gln Leu Lys Glu Arg Leu Ala Tyr Glu Phe Lys Gly His Ser Leu Leu
            325             330             335

Gln Ala Ala Arg Glu Ala Asp Val Thr Arg Ile Lys Lys His Leu Ser
            340             345             350

Leu Glu Met Val Asn Phe Lys His Pro Gln Thr His Glu Thr Ala Leu
            355             360             365

His Cys Ala Ala Ala Ser Pro Tyr Pro Lys Arg Lys Gln Ile Cys Glu
            370             375             380

Leu Leu Leu Arg Lys Gly Ala Asn Ile Asn Glu Lys Thr Lys Glu Phe
385             390             395             400

Leu Thr Pro Leu His Val Ala Ser Glu Lys Ala His Asn Asp Val Val
            405             410             415

Glu Val Val Lys His Glu Ala Lys Val Asn Ala Leu Asp Asn Leu
            420             425             430

Gly Gln Thr Ser Leu His Arg Ala Ala Tyr Cys Gly His Leu Gln Thr
            435             440             445

Cys Arg Leu Leu Leu Ser Tyr Gly Cys Asp Pro Asn Ile Ile Ser Leu
450             455             460

Gln Gly Phe Thr Ala Leu Gln Met Gly Asn Glu Asn Val Gln Gln Leu
465             470             475             480

Leu Gln Glu Gly Ile Ser Leu Gly Asn Ser Glu Ala Asp Arg Gln Leu
            485             490             495

Leu Glu Ala Ala Lys Ala Gly Asp Val Glu Thr Val Lys Lys Leu Cys
            500             505             510

Thr Val Gln Ser Val Asn Cys Arg Asp Ile Glu Gly Arg Gln Ser Thr
            515             520             525

Pro Leu His Phe Ala Ala Gly Tyr Asn Arg Val Ser Val Val Glu Tyr
            530             535             540

Leu Leu Gln His Gly Ala Asp Val His Ala Lys Asp Lys Gly Gly Leu
545             550             555             560

Val Pro Leu His Asn Ala Cys Ser Tyr Gly His Tyr Glu Val Ala Glu
            565             570             575

Leu Leu Val Lys His Gly Ala Val Val Asn Val Ala Asp Leu Trp Lys
            580             585             590

Phe Thr Pro Leu His Glu Ala Ala Lys Gly Lys Tyr Glu Ile Cys
            595             600             605

Lys Leu Leu Leu Gln His Gly Ala Asp Pro Thr Lys Lys Asn Arg Asp
            610             615             620

Gly Asn Thr Pro Leu Asp Leu Val Lys Asp Gly Asp Thr Asp Ile Gln
625             630             635             640

Asp Leu Leu Arg Gly Asp Ala Ala Leu Leu Asp Ala Ala Lys Lys Gly
            645             650             655

Cys Leu Ala Arg Val Lys Lys Leu Ser Ser Pro Asp Asn Val Asn Cys
            660             665             670

Arg Asp Thr Gln Gly Arg His Ser Thr Pro Leu His Leu Ala Ala Gly
            675             680             685
```

```
Tyr Asn Asn Leu Glu Val Ala Glu Tyr Leu Leu Gln His Gly Ala Asp
        690             695                 700

Val Asn Ala Gln Asp Lys Gly Gly Leu Ile Pro Leu His Asn Ala Ala
705             710                 715                     720

Ser Tyr Gly His Val Asp Val Ala Ala Leu Leu Ile Lys Tyr Asn Ala
            725                 730                 735

Cys Val Asn Ala Thr Asp Lys Trp Ala Phe Thr Pro Leu His Glu Ala
                740                 745                 750

Ala Gln Lys Gly Arg Thr Gln Leu Cys Ala Leu Leu Leu Ala His Gly
        755                 760                 765

Ala Asp Pro Thr Leu Lys Asn Gln Glu Gly Gln Thr Pro Leu Asp Leu
770                 775                 780

Val Ser Ala Asp Asp Val Ser Ala Leu Leu Thr Ala Ala Met Pro Pro
785                 790                 795                 800

Ser Ala Leu Pro Ser Cys Tyr Lys Pro Gln Val Leu Asn Gly Val Arg
                805                 810                 815

Ser Pro Gly Ala Thr Ala Asp Ala Leu Ser Ser Gly Pro Ser Ser Pro
                820                 825                 830

Ser Ser Leu Ser Ala Ala Ser Ser Leu Asp Asn Leu Ser Gly Ser Phe
        835                 840                 845

Ser Glu Leu Ser Ser Val Val Ser Ser Ser Gly Thr Glu Gly Ala Ser
850                 855                 860

Ser Leu Glu Lys Lys Glu Val Pro Gly Val Asp Phe Ser Ile Thr Gln
865                 870                 875                 880

Phe Val Arg Asn Leu Gly Leu Glu His Leu Met Asp Ile Phe Glu Arg
                885                 890                 895

Glu Gln Ile Thr Leu Asp Val Leu Val Glu Met Gly His Lys Glu Leu
            900                 905                 910

Lys Glu Ile Gly Ile Asn Ala Tyr Gly His Arg His Lys Leu Ile Lys
                915                 920                 925

Gly Val Glu Arg Leu Ile Ser Gly Gln Gln Gly Leu Asn Pro Tyr Leu
        930                 935                 940

Thr Leu Asn Thr Ser Gly Ser Gly Thr Ile Leu Ile Asp Leu Ser Pro
945                 950                 955                 960

Asp Asp Lys Glu Phe Gln Ser Val Glu Glu Met Gln Ser Thr Val
                965                 970                 975

Arg Glu His Arg Asp Gly Gly His Ala Gly Ile Phe Asn Arg Tyr
                980                 985                 990

Asn Ile Leu Lys Ile Gln Lys Val Cys Asn Lys Lys Leu Trp Glu Arg
            995                 1000                1005

Tyr Thr His Arg Arg Lys Glu Val Ser Glu Glu Asn His Asn His
        1010                1015                1020

Ala Asn Glu Arg Met Leu Phe His Gly Ser Pro Phe Val Asn Ala
        1025                1030                1035

Ile Ile His Lys Gly Phe Asp Glu Arg His Ala Tyr Ile Gly Gly
        1040                1045                1050

Met Phe Gly Ala Gly Ile Tyr Phe Ala Glu Asn Ser Ser Lys Ser
        1055                1060                1065

Asn Gln Tyr Val Tyr Gly Ile Gly Gly Gly Thr Gly Cys Pro Val
        1070                1075                1080

His Lys Asp Arg Ser Cys Tyr Ile Cys His Arg Gln Leu Leu Phe
        1085                1090                1095
```

```
Cys Arg Val Thr Leu Gly Lys Ser Phe Leu Gln Phe Ser Ala Met
    1100                1105                1110

Lys Met Ala His Ser Pro Pro Gly His His Ser Val Thr Gly Arg
    1115                1120                1125

Pro Ser Val Asn Gly Leu Ala Leu Ala Glu Tyr Val Ile Tyr Arg
    1130                1135                1140

Gly Glu Gln Ala Tyr Pro Glu Tyr Leu Ile Thr Tyr Gln Ile Met
    1145                1150                1155

Arg Pro Glu Gly Met Val Asp Gly
    1160                1165

<210> SEQ ID NO 4
<211> LENGTH: 843
<212> TYPE: PRT
<213> ORGANISM: Homo sapiens

<400> SEQUENCE: 4

Met Ser Ser Ala Met Leu Val Thr Cys Leu Pro Asp Pro Ser Ser
1                   5                   10                  15

Phe Arg Glu Asp Ala Pro Arg Pro Val Pro Gly Glu Glu Gly Glu
                20                  25                  30

Thr Pro Pro Cys Gln Pro Gly Val Gly Lys Gly Gln Val Thr Lys Pro
                35                  40                  45

Met Pro Val Ser Ser Asn Thr Arg Arg Asn Glu Asp Gly Leu Gly Glu
    50                  55                  60

Pro Glu Gly Arg Ala Ser Pro Asp Ser Pro Leu Thr Arg Trp Thr Lys
65                  70                  75                  80

Ser Leu His Ser Leu Leu Gly Asp Gln Asp Gly Ala Tyr Leu Phe Arg
                85                  90                  95

Thr Phe Leu Glu Arg Glu Lys Cys Val Asp Thr Leu Asp Phe Trp Phe
                100                 105                 110

Ala Cys Asn Gly Phe Arg Gln Met Asn Leu Lys Asp Thr Lys Thr Leu
                115                 120                 125

Arg Val Ala Lys Ala Ile Tyr Lys Arg Tyr Ile Glu Asn Asn Ser Ile
    130                 135                 140

Val Ser Lys Gln Leu Lys Pro Ala Thr Lys Thr Tyr Ile Arg Asp Gly
145                 150                 155                 160

Ile Lys Lys Gln Gln Ile Asp Ser Ile Met Phe Asp Gln Ala Gln Thr
                165                 170                 175

Glu Ile Gln Ser Val Met Glu Glu Asn Ala Tyr Gln Met Phe Leu Thr
                180                 185                 190

Ser Asp Ile Tyr Leu Glu Tyr Val Arg Ser Gly Gly Glu Asn Thr Ala
                195                 200                 205

Tyr Met Ser Asn Gly Gly Leu Gly Ser Leu Lys Val Val Cys Gly Tyr
    210                 215                 220

Leu Pro Thr Leu Asn Glu Glu Glu Trp Thr Cys Ala Asp Phe Lys
225                 230                 235                 240

Cys Lys Leu Ser Pro Thr Val Val Gly Leu Ser Ser Lys Thr Leu Arg
                245                 250                 255

Ala Thr Ala Ser Val Arg Ser Thr Glu Thr Val Asp Ser Gly Tyr Arg
                260                 265                 270

Ser Phe Lys Arg Ser Asp Pro Val Asn Pro Tyr His Ile Gly Ser Gly
                275                 280                 285

Tyr Val Phe Ala Pro Ala Thr Ser Ala Asn Asp Ser Glu Ile Ser Ser
    290                 295                 300
```

```
Asp Ala Leu Thr Asp Asp Ser Met Ser Met Thr Asp Ser Ser Val Asp
305                 310                 315                 320

Gly Ile Pro Pro Tyr Arg Val Gly Ser Lys Lys Gln Leu Gln Arg Glu
            325                 330                 335

Met His Arg Ser Val Lys Ala Asn Gly Gln Val Ser Leu Pro His Phe
            340                 345                 350

Pro Arg Thr His Arg Leu Pro Lys Glu Met Thr Pro Val Glu Pro Ala
            355                 360                 365

Thr Phe Ala Ala Glu Leu Ile Ser Arg Leu Glu Lys Leu Lys Leu Glu
370                 375                 380

Leu Glu Ser Arg His Ser Leu Glu Glu Arg Leu Gln Gln Ile Arg Glu
385                 390                 395                 400

Asp Glu Glu Arg Glu Gly Ser Glu Leu Thr Leu Asn Ser Arg Glu Gly
            405                 410                 415

Ala Pro Thr Gln His Pro Leu Ser Leu Leu Pro Ser Gly Ser Tyr Glu
            420                 425                 430

Glu Asp Pro Gln Thr Ile Leu Asp Asp His Leu Ser Arg Val Leu Lys
            435                 440                 445

Thr Pro Gly Cys Gln Ser Pro Gly Val Gly Arg Tyr Ser Pro Arg Ser
450                 455                 460

Arg Ser Pro Asp His His His His His Ser Gln Tyr His Ser Leu
465                 470                 475                 480

Leu Pro Pro Gly Gly Lys Leu Pro Ala Ala Ser Pro Gly Ala
            485                 490                 495

Cys Pro Leu Leu Gly Gly Lys Gly Phe Val Thr Lys Gln Thr Thr Lys
            500                 505                 510

His Val His His His Tyr Ile His His His Ala Val Pro Lys Thr Lys
            515                 520                 525

Glu Glu Ile Glu Ala Glu Ala Thr Gln Arg Val His Cys Phe Cys Pro
530                 535                 540

Gly Gly Ser Glu Tyr Tyr Cys Tyr Ser Lys Cys Lys Ser His Ser Lys
545                 550                 555                 560

Ala Pro Glu Thr Met Pro Ser Glu Gln Phe Gly Gly Ser Arg Gly Ser
            565                 570                 575

Thr Leu Pro Lys Arg Asn Gly Lys Gly Thr Glu Pro Gly Leu Ala Leu
            580                 585                 590

Pro Ala Arg Glu Gly Gly Ala Pro Gly Gly Ala Gly Ala Leu Gln Leu
            595                 600                 605

Pro Arg Glu Glu Gly Asp Arg Ser Gln Asp Val Trp Gln Trp Met Leu
            610                 615                 620

Glu Ser Glu Arg Gln Ser Lys Pro Lys Pro His Ser Ala Gln Ser Thr
625                 630                 635                 640

Lys Lys Ala Tyr Pro Leu Glu Ser Ala Arg Ser Ser Pro Gly Glu Arg
            645                 650                 655

Ala Ser Arg His His Leu Trp Gly Gly Asn Ser Gly His Pro Arg Thr
            660                 665                 670

Thr Pro Arg Ala His Leu Phe Thr Gln Asp Pro Ala Met Pro Pro Leu
            675                 680                 685

Thr Pro Pro Asn Thr Leu Ala Gln Leu Glu Glu Ala Cys Arg Arg Leu
            690                 695                 700

Ala Glu Val Ser Lys Pro Pro Lys Gln Arg Cys Cys Val Ala Ser Gln
705                 710                 715                 720
```

```
Gln Arg Asp Arg Asn His Ser Ala Thr Val Gln Thr Gly Ala Thr Pro
                725                 730                 735

Phe Ser Asn Pro Ser Leu Ala Pro Glu Asp His Lys Glu Pro Lys Lys
            740                 745                 750

Leu Ala Gly Val His Ala Leu Gln Ala Ser Glu Leu Val Val Thr Tyr
        755                 760                 765

Phe Phe Cys Gly Glu Glu Ile Pro Tyr Arg Arg Met Leu Lys Ala Gln
    770                 775                 780

Ser Leu Thr Leu Gly His Phe Lys Glu Gln Leu Ser Lys Lys Gly Asn
785                 790                 795                 800

Tyr Arg Tyr Tyr Phe Lys Lys Ala Ser Asp Glu Phe Ala Cys Gly Ala
                805                 810                 815

Val Phe Glu Glu Ile Trp Glu Asp Glu Thr Val Leu Pro Met Tyr Glu
            820                 825                 830

Gly Arg Ile Leu Gly Lys Val Glu Arg Ile Asp
        835                 840
```

<210> SEQ ID NO 5
<211> LENGTH: 466
<212> TYPE: PRT
<213> ORGANISM: Artificial Sequence
<220> FEATURE:
<223> OTHER INFORMATION: synthetic construct

<400> SEQUENCE: 5

```
Met Asp Arg Lys Phe Val Phe Leu Val Ser Ile Leu Ser Ile Val Val
1               5                   10                  15

Ala Ser Val Thr Gly Glu Thr Thr Arg Ala Pro Thr Pro Thr Pro Thr
                20                  25                  30

Pro Thr Pro Thr Pro Thr Pro Thr Pro Thr Pro Thr Pro Thr Pro Thr
            35                  40                  45

Pro Thr Pro Thr Pro Thr Pro Thr Pro Thr Pro Thr Pro Thr Pro Thr
        50                  55                  60

Pro Thr Pro Thr Pro Thr Pro Thr Pro Thr Pro Thr Pro Thr Pro Thr
65                  70                  75                  80

Pro Thr Pro Thr Pro Thr Pro Thr Pro Thr Pro Thr Pro Thr Pro Thr
                85                  90                  95

Pro Thr Pro Thr Pro Thr Pro Thr Pro Thr Pro Thr Pro Thr Pro Thr
            100                 105                 110

Pro Thr Pro Thr Pro Thr Pro Thr Pro Thr Pro Thr Pro Thr Pro Thr
        115                 120                 125

Pro Thr Pro Thr Pro Thr Pro Thr Pro Thr Pro Thr Pro Thr Pro Thr
    130                 135                 140

Pro Thr Pro Thr Pro Thr Pro Thr Pro Thr Pro Thr Pro Thr Pro Thr
145                 150                 155                 160

Pro Thr Pro Thr Pro Thr Pro Thr Pro Thr Pro Thr Pro Thr Pro Thr
                165                 170                 175

Pro Thr Pro Thr Pro Thr Pro Thr Pro Thr Pro Thr Pro Thr Pro Thr
            180                 185                 190

Pro Thr Pro Thr Pro Thr Pro Thr Pro Thr Pro Thr Pro Thr Pro Thr
        195                 200                 205

Pro Thr Pro Thr Pro Thr Pro Thr Pro Thr Pro Thr Pro Thr Pro Thr
    210                 215                 220

Pro Thr Ser Met Val Ser Lys Gly Glu Glu Leu Phe Thr Gly Val Val
225                 230                 235                 240
```

Pro Ile Leu Val Glu Leu Asp Gly Asp Val Asn Gly His Lys Phe Ser
                245                 250                 255

Val Ser Gly Glu Gly Glu Gly Asp Ala Thr Tyr Gly Lys Leu Thr Leu
            260                 265                 270

Lys Phe Ile Cys Thr Thr Gly Lys Leu Pro Val Pro Trp Pro Thr Leu
        275                 280                 285

Val Thr Thr Leu Thr Tyr Gly Val Gln Cys Phe Ser Arg Tyr Pro Asp
    290                 295                 300

His Met Lys Gln His Asp Phe Phe Lys Ser Ala Met Pro Glu Gly Tyr
305                 310                 315                 320

Val Gln Glu Arg Thr Ile Phe Phe Lys Asp Asp Gly Asn Tyr Lys Thr
                325                 330                 335

Arg Ala Glu Val Lys Phe Glu Gly Asp Thr Leu Val Asn Arg Ile Glu
            340                 345                 350

Leu Lys Gly Ile Asp Phe Lys Glu Asp Gly Asn Ile Leu Gly His Lys
        355                 360                 365

Leu Glu Tyr Asn Tyr Asn Ser His Asn Val Tyr Ile Met Ala Asp Lys
    370                 375                 380

Gln Lys Asn Gly Ile Lys Val Asn Phe Lys Ile Arg His Asn Ile Glu
385                 390                 395                 400

Asp Gly Ser Val Gln Leu Ala Asp His Tyr Gln Gln Asn Thr Pro Ile
                405                 410                 415

Gly Asp Gly Pro Val Leu Leu Pro Asp Asn His Tyr Leu Ser Thr Gln
            420                 425                 430

Ser Ala Leu Ser Lys Asp Pro Asn Glu Lys Arg Asp His Met Val Leu
        435                 440                 445

Leu Glu Phe Val Thr Ala Ala Gly Ile Thr Leu Gly Met Asp Glu Leu
    450                 455                 460

Tyr Lys
465

<210> SEQ ID NO 6
<211> LENGTH: 8
<212> TYPE: PRT
<213> ORGANISM: Artificial Sequence
<220> FEATURE:
<223> OTHER INFORMATION: synthetic construct

<400> SEQUENCE: 6

Asp Tyr Lys Asp Asp Asp Asp Lys
1               5

<210> SEQ ID NO 7
<211> LENGTH: 239
<212> TYPE: PRT
<213> ORGANISM: Artificial Sequence
<220> FEATURE:
<223> OTHER INFORMATION: synthetic construct

<400> SEQUENCE: 7

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

```
Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```